US011613728B2

(12) United States Patent
Dairi et al.

(10) Patent No.: US 11,613,728 B2
(45) Date of Patent: Mar. 28, 2023

(54) MICROORGANISM PRODUCING EICOSAPENTAENOIC ACID AND METHOD FOR PRODUCING EICOSAPENTAENOIC ACID

(71) Applicant: KYOWA HAKKO BIO CO., LTD., Tokyo (JP)

(72) Inventors: Tohru Dairi, Sapporo (JP); Yasuharu Satoh, Sapporo (JP); Shohei Hayashi, Sapporo (JP); Mai Naka, Sapporo (JP); Tetsuro Ujihara, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 60 days.

(21) Appl. No.: 17/266,984

(22) PCT Filed: Aug. 9, 2019

(86) PCT No.: PCT/JP2019/031652
§ 371 (c)(1),
(2) Date: Feb. 8, 2021

(87) PCT Pub. No.: WO2020/032261
PCT Pub. Date: Feb. 13, 2020

(65) Prior Publication Data
US 2021/0309960 A1  Oct. 7, 2021

(30) Foreign Application Priority Data
Aug. 10, 2018 (JP) .............................. JP2018-151234

(51) Int. Cl.
| | |
|---|---|
| *C12N 1/10* | (2006.01) |
| *C12N 15/70* | (2006.01) |
| *C12P 7/64* | (2022.01) |
| *C12R 1/90* | (2006.01) |

(52) U.S. Cl.
CPC ............ *C12N 1/105* (2021.05); *C12N 15/70* (2013.01); *C12P 7/64* (2013.01); *C12R 2001/90* (2021.05)

(58) Field of Classification Search
CPC ............ C12N 1/105; C12N 15/70; C12P 7/64
See application file for complete search history.

(56) References Cited

U.S. PATENT DOCUMENTS

| | | | |
|---|---|---|---|
| 7,897,844 | B2 | 3/2011 | Metz et al. |
| 8,003,772 | B2 | 8/2011 | Weaver et al. |
| 2008/0022422 | A1 | 1/2008 | Weaver et al. |
| 2008/0038793 | A1 | 2/2008 | Metz et al. |
| 2008/0038799 | A1 | 2/2008 | Weaver et al. |
| 2010/0266564 | A1 | 10/2010 | Apt et al. |

FOREIGN PATENT DOCUMENTS

| | | | |
|---|---|---|---|
| EP | 2366772 B1 | 1/2016 | |
| JP | 2013-055893 A | 3/2013 | |
| JP | 2017-184690 A | 10/2017 | |
| WO | 2004/087879 A2 | 10/2004 | |
| WO | WO-2006135866 A2 * | 12/2006 | ............... A23D 9/00 |
| WO | WO 2008/144473 A2 | 11/2008 | |
| WO | WO 2010/108114 A2 | 9/2010 | |
| WO | 2011/146524 A1 | 11/2011 | |

OTHER PUBLICATIONS

Hayashi et al., "Enhanced Production of Polyunsaturated Fatty Acids by Enzyme Engineering of Tandem Acyl Carrier Proteins," *Scientific Reports*, 6: 35441 (2016).
Ujihara et al., "Identification of a Novel Type of Polyunsaturated Fatty Acid Synthase Involved in Arachidonic Acid Biosynthesis," *FEBS Letters*, 588(21): 4032-4036 (2014).
European Patent Office, Extended European Search Report in European Patent Application No. 19848560.9 (dated Apr. 20, 2022).
Agostoni et al., "Effects of Diet on the Lipid and Fatty Acid Status of Full-term Infants at 4 Months," *J. Am. Coll. Nutr.*, 13(6): 658-684 (1994).
Koletzko et al., "Arachidonic Acid and Early Human Growth: Is there a Relation?," *Ann. Nutr. Metab.*, 35(3): 128-131 (1991).
Metz et al., "Production of Polyunsaturated Fatty Acids by Polyketide Synthases in Both Prokaryotes and Eukaryotes," *Science*, 293(5528): 290-293 (2001).
Metz et al., "Biochemical characterization of polyunsaturated fatty acid synthesis in *Schizochytrium*: Release of the products as free fatty acids," *Plant Physiol. Biochem.*, 47(6): 472-478 (2009).
Orikasa et al., "pfaB products determine the molecular species produced in bacterial polyunsaturated fatty acid biosynthesis," *FEMS Microbiol. Lett.*, 295(2): 170-176 (2009).
Shulse et al., "Widespread Occurrence of Secondary Lipid Biosynthesis Potential in Microbial Lineages," *PLoS One*, 6: e20146 (2011).
Wakil et al., "Fatty Acid Synthesis and its Regulation," *Annu. Rev. Biochem.*, 52: 537-579 (1983).
Xie et al., "Functional analysis of the dehydratase domains of a PUFA synthase from *Thraustochytrium* in *Escherichia coli*," *Appl. Microbiol. Biotechnol.*, 102(2): 847-856 (2018).
Japanese Patent Office, International Search Report in International Patent Application No. PCT/JP2019/031652 (dated Oct. 8, 2019).

\* cited by examiner

*Primary Examiner* — Louise W Humphrey
*Assistant Examiner* — Trevor L Kane
(74) *Attorney, Agent, or Firm* — Leydig, Voit & Mayer, Ltd.

(57) ABSTRACT

An object of the present invention is to provide a microorganism that efficiently produces EPA and a method for producing EPA using the microorganism. The present invention relates to a microorganism having an ability to produce docosahexaenoic acid (DHA), wherein the microorganism contains a protein composed of an amino acid sequence in which at least one of the amino acid residues at positions 6, 65, 230, 231, and 275 in the amino acid sequence represented by SEQ ID NO: 2 has been substituted with another amino acid residue (mutated OrfB), and is capable of producing eicosapentaenoic acid (EPA), and the like.

12 Claims, 2 Drawing Sheets
Specification includes a Sequence Listing.

FIG. 2

```
PhoC_KS      -YQGIQGESDREYCDKGNIQNESFDSNGYRLPAETEEGLDESFLWALDTSRKAL
EpaC_KS      -YQGIQGQADREYCDRGNYIRNEFFDPQGYQLLPATFAGLDESFLWALDCSKKAL
DhaC_KS      -YTANKGDTDKFYCVHGGNISDFNFDASGYQLDNDYLAGLDDLNQWGLYYTKQAL
AraC_KS      FYEDKKGAVDRCVSLRGGYIRDEFDPTGYQLSADFLAQDKLYQWSLYVAKTAL
OH4_OrfB_KS  -------EHFKAERSNFADTFCNENYGCVDDS----------VDNEHELLIKLSKKAL
20888_OrfB_KS -------EHYKAERSKYADTFCNETYGTLDENE----------IDNEHELLNLAKQAL
ruler        ..50......60......70......80......90......100.
                                    F65

PhoC_KS      LDAACASSVYSIKLACDYLNTGKADMLAGAVSGADPFFINMGFSIFHAYPDH--
EpaC_KS      LDAACASSVYAIKLACDYLTTGKADMLAGAVSGADPFFINMGFSIFHAYPDH--
DhaC_KS      LDAACASSCYSVKLACDYLHTGKANMMLAGAVSAADPMFVNMGFSIFQAYPAN--
AraC_KS      LDAACATSLYAIKLACDELITCKADMLAGAVCGSDQIFIHMGFSIFHAYAPH--
OH4_OrfB_KS  VDAACATALYVIRLAQDHLVSGAAADVMLAGATCFPEPFFILSGEFSTFQAMPVS-G
20888_OrfB_KS VDAACATALYVIRLAQDHLVSGAADVMLCGATCLPEPFFILSGFSTFQAMPVGTG
ruler        ..200......210......220......230......240......250.
                                                F230      I231
```

MICROORGANISM PRODUCING EICOSAPENTAENOIC ACID AND METHOD FOR PRODUCING EICOSAPENTAENOIC ACID

CROSS-REFERENCE TO RELATED APPLICATIONS

This patent application is the U.S. national phase of International Patent Application No. PCT/JP2019/031652, filed Aug. 9, 2019, which claims the benefit of Japanese Patent Application No. 2018-151234, filed on Aug. 10, 2018, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 218,113 bytes ASCII (Text) file named "752298Sequence-Listing.txt," created Feb. 8, 2021.

TECHNICAL FIELD

The present invention relates to a microorganism that produces eicosapentaenoic acid and a method for producing eicosapentaenoic acid using the microorganism.

BACKGROUND ART

Long-chain fatty acids having a plurality of unsaturated bonds in a molecule such as docosahexaenoic acid (hereinafter, referred to as DHA), eicosapentaenoic acid (hereinafter, referred to as EPA), arachidonic acid (hereinafter, referred to as ARA), and docosapentaenoic acid (hereinafter, referred to as DPA) are referred to as polyunsaturated fatty acids (hereinafter, referred to as PUFAs). PUFAs are known to have various physiological functions such as prevention of arteriosclerosis or hyperlipidemia (NPL 1 and NPL 2).

As the PUFA biosynthetic pathway, the following two types are known: an aerobic pathway and an anaerobic pathway by a polyunsaturated fatty acid polyketide synthase (hereinafter referred to as PUFA-PKS). The aerobic pathway is a pathway in which a PUFA is synthesized by introducing a double bond using a plurality of desaturases into a long-chain fatty acid such as palmitic acid synthesized using a fatty acid synthase or by elongating a carbon chain using a chain elongase, and is a synthetic pathway which is possessed by many organisms and has been known for many years (NPL 3).

On the other hand, the anaerobic pathway by a PUFA-PKS is a pathway for synthesizing a PUFA from malonyl-CoA, and some marine bacteria or eukaryotes of the *Labyrinthulomycetes* are known to have the pathway (NPL 4 and NPL 5).

The PUFA-PKS is a complex enzyme (hereinafter, also referred to as protein complex) composed of a plurality of proteins, and in each protein, a plurality of functional domains involved in the PUFA synthesis are present.

The functional domains present in the PUFA-PKS include a β-ketoacyl-acyl carrier protein synthase domain (hereinafter referred to as KS domain) believed to be involved in the condensation of malonyl-ACP and acyl-ACP, an acyl carrier protein domain (hereinafter, referred to as ACP domain) believed to function as a fatty acid synthesis site by binding to an acyl group via a phosphopantetheinyl group through a thioester bond, a ketoreductase domain (hereinafter referred to as KR domain) believed to reduce a carbonyl group generated by condensation, a DH domain believed to form a double bond by dehydration of a hydroxy group generated by the KR domain, a chain elongation factor domain (hereinafter, referred to as CLF domain) believed to be involved in the elongation of a carbon chain, an enoyl reductase domain (hereinafter referred to as ER domain) believed to reduce an obtained double bond, an acyltransferase domain (hereinafter, referred to as AT domain) and a malonyl-CoA:acyltransferase domain (hereinafter, referred to as MAT domain) believed to be involved in the transfer of an acyl group, and a phosphopantetheine transferase domain (hereinafter referred to as PPT domain) believed to activate an ACP domain, and it is considered that a carbon chain of a fatty acid is elongated by the plurality of domains working in cooperation with one another.

It is known that the PUFA-PKS produces a different type of PUFA depending on its type. For example, a PUFA-PKS derived from *Schizochytrium* sp., *Aurantiochytrium* sp., and *Moritella marina* produces DHA as a main product, a PUFA-PKS derived from *Shewanella oneidensis* and *Photobacterium profundum* produces EPA as a main product, and a PUFA-PKS derived from *Aureispira marina* produces ARA as a main product, and other PUFAs are hardly produced, or even if such other PUFAs are produced, they are produced in a small amount as compared with the main product.

The PUFA-PKS has high product specificity in this manner, however, many studies aiming at the functional analysis of the PUFA-PKS have been conducted so far. In NPLs 4 and 6, studies in which a PUFA-PKS gene is cloned from bacteria of the genus *Shewanella* or eukaryotes of the Stramenopiles and expressed in a heterogeneous organism to produce a PUFA have been conducted.

NPL 7 discloses that a pfaB gene encoding an AT domain is involved in the type of PUFA to be produced based on a study using a pfaB gene that is a structural gene of a PUFA-PKS derived from *Moritella marina* that produces DHA and a pfaB gene that constitutes a PUFA-PKS derived from *Shewanella pneumatophori* that produces EPA.

NPL 8 discloses that when a DH domain of a PUFA-PKS derived from the genus *Thraustochytrium* is introduced into *E. coli*, the production amount of fatty acids increases, and also the proportion of unsaturated fatty acids increases.

As a method for industrially producing EPA, a method of purifying EPA from a fish oil, or the like is known, but the method has a problem that there are a lot of by-products (PTL 2).

CITATION LIST

Patent Literature

PTL 1: WO 2008/144473
PTL 2: JP-A-2013-055893

Non Patent Literature

NPL 1: Annu. Nutr. Metabol., 1991, 35, 128-131
NPL 2: J. Am. Coll. Nutr., 1994, 13, 658-664
NPL 3: Ann. Rev. Biochem., 1983, 52, 537-579
NPL 4: Science, 2001, 293, 290-293
NPL 5: PLoS One, 2011, 6, e20146
NPL 6: Plant Physiol. Biochem., 2009, 47, 472-478
NPL 7: FEMS Microbiol. Lett., 2009, 295, 170-176
NPL 8: Appl. Microbiol. Biotechnol., 2018, 847-856

SUMMARY OF INVENTION

Technical Problem

As described above, as a method for industrially producing EPA, a method of purifying EPA from a fish oil, or the like is used, but the method has a problem that there are a lot of by-products and the production efficiency is low, and therefore, an efficient method for producing EPA has been awaited.

Accordingly, an object of the present invention is to provide a microorganism that efficiently produces EPA and a method for producing EPA using the microorganism.

Solution to Problem

The present inventors found that by expressing OrfB in which a mutation has been introduced into a specific amino acid residue in a microorganism having an ability to produce DHA, a PUFA containing EPA at a high concentration can be produced, and thus completed the present invention.

The present invention relates to the following.

1. A microorganism having an ability to produce DHA, wherein the microorganism contains a protein composed of an amino acid sequence in which at least one of the amino acid residues at positions 6, 65, 230, 231, and 275 in the amino acid sequence represented by SEQ ID NO: 2 has been substituted with another amino acid residue (hereinafter referred to as mutated OrfB), and the microorganism is capable of producing eicosapentaenoic acid (hereinafter referred to as EPA).

2. A microorganism having an ability to produce DHA, wherein the microorganism contains a protein composed of an amino acid sequence in which an amino acid residue corresponding to at least one of the amino acid residues at positions 6, 65, 230, 231, and 275 in SEQ ID NO: 2 has been substituted with another amino acid residue (hereinafter referred to as mutated OrfB homolog) in an amino acid sequence of a homolog protein of a protein composed of the amino acid sequence represented by SEQ ID NO: 2 (hereinafter referred to as OrfB homolog) when the amino acid sequence of the OrfB homolog and the amino acid sequence represented by SEQ ID NO: 2 are aligned, and the microorganism is capable of producing EPA.

3. The microorganism according to the above 1 or 2, wherein the microorganism having an ability to produce DHA is a *Labyrinthulomycetes* microorganism.

4. The microorganism according to the above 3, wherein the *Labyrinthulomycetes* microorganism is a *Labyrinthulomycetes* microorganism belonging to the genus *Aurantiochytrium*, the genus *Thraustochytrium*, the genus *Ulkenia*, the genus *Parietichytrium*, the genus *Labyrinthula*, the genus *Aplanochytrium*, the genus *Oblongichytrium*, or the genus *Schizochytrium*.

5. The microorganism according to the above 1 or 2, wherein the microorganism having an ability to produce DHA is a microorganism in which genes encoding respective domains described in the following (a) to (j) having an activity of synthesizing DHA have been introduced into a microorganism that does not have a DHA metabolic pathway:

(a) a KS domain;
(b) a MAT domain;
(c) an ACP domain;
(d) a KR domain;
(e) a polyketide synthase dehydratase (hereinafter referred to as PS-DH) domain;
(f) a CLF domain;
(g) a AT domain;
(h) a FabA-like β-hydroxyacyl-ACP dehydratase (hereinafter referred to as FabA-DH) domain;
(i) an ER domain; and
(j) a PPT domain.

6. The microorganism according to the above 5, wherein the microorganism that does not have a DHA metabolic pathway is a microorganism belonging to the genus *Escherichia*, the genus *Bacillus*, the genus *Corynebacterium*, the genus *Yarrowia*, the genus *Saccharomyces*, the genus *Candida*, or the genus *Pichia*.

7. A method for producing EPA or an EPA-containing composition, including culturing the microorganism according to any one of the above 1 to 6 in a culture medium so as to produce and accumulate EPA or an EPA-containing composition in a culture, and collecting EPA or the EPA-containing composition from the culture.

8. A method for producing EPA or an EPA-containing composition using the following microorganism (I) or (II) capable of producing EPA:

(I) a microorganism having an ability to produce DHA, wherein the microorganism contains mutated OrfB composed of an amino acid sequence in which at least one of the amino acid residues at positions 6, 65, 230, 231, and 275 in the amino acid sequence represented by SEQ ID NO: 2 has been substituted with another amino acid residue, and the microorganism is capable of producing EPA; or (II) a microorganism having an ability to produce DHA, wherein the microorganism contains a mutated OrfB homolog composed of an amino acid sequence in which at least one of the amino acid residues at positions 6, 65, 230, 231, and 275 in SEQ ID NO: 2 has been substituted with another amino acid residue in an amino acid sequence of an OrfB homolog when the amino acid sequence of the OrfB homolog and the amino acid sequence represented by SEQ ID NO: 2 are aligned, and the microorganism is capable of producing EPA.

Advantageous Effects of Invention

The microorganism of the present invention can efficiently produce EPA by expressing mutated OrfB in which a mutation has been introduced into a specific amino acid residue so as to change the specificity for a substrate in a microorganism having an ability to produce DHA. According to the method for producing EPA of the present invention, EPA can be produced at low cost with high efficiency by expressing mutated OrfB in a microorganism capable of producing DHA at an industrial level, and thus the method can be applied to the production of EPA at an industrial level.

BRIEF DESCRIPTION OF DRAWINGS

FIG. 2 shows an example of the results of alignment of amino acid sequences of OrfB and an OrfB homolog.

DESCRIPTION OF EMBODIMENTS

Figure 1:
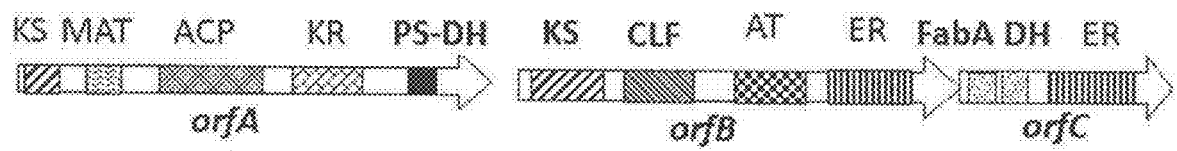
FIG. 1 shows a schematic diagram of the structure of a PUFA-PKS of the genus *Aurantiochytrium* (*Aurantiochytrium* sp.).

In the present invention, the "polyunsaturated fatty acid (PUFA)" refers to a long-chain fatty acid having a carbon chain length of 18 or more and having 2 or more unsaturated bonds. Further, the "domain" as used herein refers to a part composed of a continuous amino acid sequence in a protein, and is a region having a specific biological activity or function in the protein.

In the present invention, the "PUFA-PKS" has the same meaning as a PUFA synthase. The PUFA synthase is a group of enzymes that synthesize a specific long-chain unsaturated fatty acid using malonyl-CoA or the like as a carbon source, and refers to one containing the respective domains of KS, MAT, ACP, KR, PS-DH, CLF, AT, FabA-DH, ER, and PPTase (ACOS Lipid Library: PUFA synthase; Science, 2001, 293, 290-293; PLoS One, 2011, 6, e20146, etc.).

The KS domain is a domain included in a protein constituting a protein complex having a PUFA-PKS activity, and refers to a domain involved in the condensation of malonyl ACP and acyl ACP.

The MAT domain and the AT domain are domains included in a protein constituting a protein complex having a PUFA-PKS activity, and refer to domains involved in the transfer of an acyl group.

The ACP domain is a domain included in a protein constituting a protein complex having a PUFA-PKS activity, and refers to a domain that functions as a fatty acid synthesis site by binding to an acyl group via a phosphopantetheinyl group through a thioester bond, and is essential for a PUFA-PKS activity.

The KR domain is a domain included in a protein constituting a protein complex having a PUFA-PKS activity, and refers to a domain involved in the reduction of a ketone group generated by condensation.

The PS-DH domain and the FabA-DH domain, which are DH domains, are domains included in a protein constituting a protein complex having a PUFA-PKS activity, and refers to domains involved in the dehydration of a hydroxy group generated by the reduction of a ketone group.

The CLF domain is a domain included in a protein constituting a protein complex having a PUFA-PKS activity, and refers to a domain involved in the elongation of a carbon chain.

The ER domain is a domain included in a protein constituting a protein complex having a PUFA-PKS activity.

The PPTase is an enzyme that constitutes a protein complex having a PUFA-PKS activity, and refers to an enzyme involved in the activation of an ACP domain.

In this description, the identity of amino acid sequences or nucleotide sequences can be determined using the algorithm BLAST (Pro. Natl. Acad. Sci. USA, 1993, 90, 5873) or FASTA (Methods Enzymol., 1990, 183, 63) by Karlin and Altschul. Based on the algorithm BLAST, programs called BLASTN and BLASTX have been developed (J. Mol. Biol., 1990, 215, 403). When analyzing a nucleotide sequence by BLASTN based on BLAST, parameters are set to, for example, as follows: score=100 and wordlength=12. Further, when analyzing an amino acid sequence by BLASTX based on BLAST, parameters are set to, for example, as follows: score=50 and wordlength=3. When using BLAST and Gapped BLAST programs, the default parameters of each program are used. Specific methods of these analysis methods are known (see www.ncbi.nlm.nih.gov).

The "exogenous" as used herein refers to a substance that is not endogenous but is derived from a heterogeneous substance, and is used for meaning that a gene based on the present invention is introduced into a host organism when the host organism before transformation does not have a gene to be introduced according to the present invention, when a protein encoded by the gene is not substantially expressed, and when an amino acid sequence of the protein is encoded by a different gene, but the activity of an endogenous protein after transformation is not exerted.

[Microorganism]

The microorganism of the present invention is a microorganism having an ability to produce docosahexaenoic acid (DHA), and is characterized in that the microorganism contains a protein composed of an amino acid sequence in which at least one of the amino acid residues at positions 6, 65, 230, 231, and 275 in the amino acid sequence represented by SEQ ID NO: 2 has been substituted with another amino acid residue (mutated OrfB), and is capable of producing eicosapentaenoic acid (EPA).

As the microorganism having an ability to produce DHA, the following (1) and (2) are exemplified.

(1) a microorganism having a DHA metabolic activity (2) a microorganism having an ability to produce DHA by introducing genes encoding a KS domain, a MAT domain, an ACP domain, a KR domain, a PS-DH domain, a CLF domain, an AT domain, a FabA-DH domain, an ER domain, and a PPT domain that are domains constituting a PUFA-PKS having an activity of biosynthesizing DHA into a host organism using a microorganism that does not have a DHA metabolic activity as the host organism The "host organism" as used herein refers to an original organism to be subjected to genetic modification, transformation, or the like. When the original organism to be subjected to transformation by gene transfer is a microorganism, it is also referred to as a parent strain or a host strain.

As the microorganism (1) having a DHA metabolic activity, a microorganism belonging to the *Labyrinthulomycetes* is exemplified. Examples of the microorganism belonging to the *Labyrinthulomycetes* include microorganisms of the genus *Aurantiochytrium*, the genus *Thraustochytrium*, the genus *Ulkenia*, the genus *Parietichytrium*, the genus *Labyrinthula*, the genus *Aplanochytrium*, the genus *Oblongichytrium*, or the genus *Schizochytrium*. Preferred examples thereof include *Aurantiochytrium limacinum, Thraustochytrium aureum*, and the like, however, the microorganism is not limited thereto as long as the microorganism has a DHA metabolic pathway by nature.

As the microorganism having a DHA metabolic activity, specifically, for example, a microorganism belonging to the genus *Aurantiochytrium* is preferred, and for example, *Aurantiochytrium* sp. OH4 strain (accession number FERM BP-11524) and the like are exemplified, and further, a microorganism that is a mutant thereof and has an ability to produce DHA may be used.

The *Aurantiochytrium* sp. OH4 strain was deposited in the National Institute of Technology and Evaluation (NITE), Patent Microorganisms Depositary Center, located at Central 6, 1-1, Higashi, Tsukuba, Ibaraki, Japan (zip code: 305-8566). The date of receipt (date of deposit) is January 11, Heisei 25 (AD 2013), and the accession number is FERM BP-11524.

The microorganism (2) that does not have a DHA metabolic activity refers to a microorganism that does not have an ability to produce DHA by nature. Examples of the microorganism that does not have a DHA metabolic activity include a bacterium, a microalga, a fungus, a protist, and a protozoan.

Examples of the bacterium include microorganisms belonging to a genus selected from the group consisting of the genus *Escherichia*, the genus *Serratia*, the genus *Bacillus*, the genus *Brevibacterium*, the genus *Corynebacterium*, the genus *Microbacterium*, the genus *Pseudomonas*, and the genus *Aureispira*. Among these, a microorganism selected from the group consisting of *Escherichia coli* XL1-Blue,

*Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* BL21 codon plus (manufactured by Stratagene Corporation), *Serratia ficaria, Serratia fonticola, Serratia liquefaciens, Serratia marcescens, Bacillus subtilis, Bacillus amyloliquefaciens, Brevibacterium immariophilum* ATCC 14068, *Brevibacterium saccharolyticum* ATCC 14066, *Corynebacterium ammoniagenes, Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354, *Pseudomonas* sp. D-0110, and *Aureispira marina* JCM 23201 is preferred.

Examples of the microalga include the class Euglenophyceae (for example, the genus *Euglena* and the genus *Peranema*), the class Chrysophyceae (for example, the genus *Ochromonas*), the class Dinobryaceae (for example, the genus *Dinobryon*, the genus *Platychrysis*, and the genus *Chrysochromulina*), the class Dinophyceae (for example, the genus *Crypthecodinium*, the genus *Gymnodinium*, the genus *Peridinium*, the genus *Ceratium*, the genus *Gyrodinium*, and the genus *Oxyrrhis*), the class Cryptophyceae (for example, the genus *Cryptomonas* and the genus *Rhodomonas*), the class Xanthophyceae (for example, the genus *Olisthodiscus*) (and including a variety of algae to pass into an amoeboid phase as in the case of a zoospore or a gamete of Rhizochloridaceae and *Aphanochaete pascheri, Bumilleria stigeoclonium* and *Vaucheria geminata*), the class Eustigmatophyceae, and the class Prymnesiopyceae (including, for example, the genus *Prymnesium* and the genus *Diacronema*).

Preferred species in such genera are not particularly limited, however, *Nannochloropsis oculata, Crypthecodinium cohnii,* and *Euglena gracilis* are exemplified.

Examples of the fungus include yeast including the genus *Saccharomyces* (for example, *Saccharomyces cerevisiae* and *Saccharomyces carlsbergensis*), or other yeast such as the genus *Yarrowia*, the genus *Candida*, the genus *Pichia*, the genus *Kluyveromyces*, or other fungi, for example, filamentous fungi such as the genus *Aspergillus*, the genus *Neurospora*, and the genus *Penicillium*, and the like.

A cell line that can be utilized as a host cell may be a wild type in the usual sense, or may be an auxotrophic mutant or an antibiotic resistant mutant, or may be transformed so as to have any of various marker genes. For example, a strain exhibiting resistance to an antibiotic such as chloramphenicol, ampicillin, kanamycin, or tetracycline is exemplified.

As the genes encoding respective domains constituting a PUFA-PKS having an activity of biosynthesizing DHA for allowing the microorganism (2) that does not have a DHA metabolic activity to acquire an ability to produce DHA, genes encoding respective domains (a KS domain, a MAT domain, an ACP domain, a KR domain, a PS-DH domain, a CLF domain, an AT domain, a FabA-DH domain, an ER domain, and a PPT domain) constituting a PUFA-PKS having an activity of biosynthesizing DHA possessed by the microorganism (1) having a DHA metabolic activity described above are preferred.

The respective domains constituting a PUFA-PKS are not limited as long as the domains produce DHA in cooperation with one another, however, for example, respective domains included in a known PUFA-PKS are exemplified.

The expression "in cooperation with one another" as used herein means that when a certain protein is allowed to coexist with another protein, the proteins carry out a specific reaction together. In particular, in this description, the expression refers to that when a plurality of domains necessary for a PUFA-PKS activity are allowed to coexist, the domain exhibits the PUFA-PKS activity together with the other domains.

In this description, as the "known PUFA-PKS", preferably a PUFA-PKS originally possessed by a microorganism belonging to a genus selected from the group consisting of the genus *Aurantiochytrium*, the genus *Thraustochytrium*, the genus *Ulkenia*, the genus *Parietichytrium*, the genus *Labyrinthula*, the genus *Aplanochytrium*, the genus *Oblongichytrium*, and the genus *Schizochytrium*, and more preferably a PUFA-PKS originally possessed by a microorganism selected from the group consisting of *Aurantiochytrium limacinum* ATCC MYA-1381, *Schizochytrium* sp. ATCC 20888, and *Thraustochytrium aureum* ATCC 34304 are exemplified.

It can be confirmed that the PUFA-PKS composed of respective domains has a DHA synthetic activity by creating a microorganism transformed with the genes encoding the respective domains, culturing the microorganism in a culture medium so as to produce and accumulate DHA in a culture, and measuring the DHA accumulated in the culture by gas chromatography.

The PUFA-PKS is a protein complex (complex enzyme) composed of a plurality of proteins having the above-mentioned domains, and OrfB is a protein constituting the PUFA-PKS. FIG. 1 shows a schematic diagram of the domain structure constituting the protein complex of the PUFA-PKS in a microorganism belonging to the genus *Aurantiochytrium* (*Aurantiochytrium* sp.). In OrfB, one KS domain, one CLF domain, one AT domain, and one ER domain are included.

As the mutated OrfB, a protein described in the following (a) or (b) is exemplified.

(a) a protein composed of an amino acid sequence in which at least one of the amino acid residues at positions 6, 65, 230, 231, and 275 in the amino acid sequence represented by SEQ ID NO: 2 has been substituted with another amino acid residue (b) a protein composed of an amino acid sequence in which at least one of the amino acid residues corresponding to the amino acid residues at positions 6, 65, 230, 231, and 275 in the amino acid sequence represented by SEQ ID NO: 2 has been substituted with another amino acid residue in the amino acid sequence of the OrfB homolog when the amino acid sequence and the amino acid sequence represented by SEQ ID NO: 2 are aligned With respect to the above protein (a), in the amino acid sequence represented by SEQ ID NO: 2, it is preferred that at least the amino acid residue at position 230 has been substituted with another amino acid residue, it is more preferred that at least one selected from the amino acid residues at positions 6, 65, 231, and 275 has been further substituted with another amino acid residue in addition to the amino acid residue at position 230, and it is particularly preferred that the amino acid residues at positions 6 and 230, the amino acid residues at positions 65 and 230, the amino acid residues at positions 6, 65, and 230, or the amino acid residues at positions 65, 230, 231, and 275 have been substituted with another amino acid residue.

In addition, with respect to the above protein (b), in the amino acid sequence of the OrfB homolog, when the amino acid sequence of the OrfB homolog and the amino acid sequence represented by SEQ ID NO: 2 are aligned, it is preferred that at least an amino acid residue corresponding to the amino acid residue at position 230 in the amino acid sequence represented by SEQ ID NO: 2 has been substituted with another amino acid residue, it is more preferred that at least one selected from amino acid residues corresponding to the amino acid residues at positions 6, 65, 231, and 275 has been further substituted with another amino acid residue in addition to the amino acid residue corresponding to the amino acid residue at position 230, and it is particularly preferred that amino acid residues corresponding to the amino acid residues at positions 6 and 230, the amino acid residues at positions 65 and 230, the amino acid residues at positions 6, 65, and 230, or the amino acid residues at positions 65, 230, 231, and 275 have been substituted with another amino acid residue.

The OrfB homolog refers to a protein, which is composed of an amino acid sequence having a high homology with the amino acid sequence represented by SEQ ID NO: 2, in which a gene encoding the protein is considered to have the same evolutionary origin as a gene encoding the original protein because of similarity in structure and function to OrfB having the amino acid sequence represented by SEQ ID NO: 2, and which is possessed by an organism present in nature.

Specific examples of the OrfB homolog include PhoC derived from *Photobacterium profundum* represented by SEQ ID NO: 27, EpaC derived from *Shewanella oneidensis* represented by SEQ ID NO: 28, DhaC derived from *Moritella marina* represented by SEQ ID NO: 29, AraC derived from *Aureispira marina* represented by SEQ ID NO: 30, OrfB derived from *Schizochytrium* sp. (ATCC 20888) represented by SEQ ID NO: 31, and the like. An example of the results of alignment of the amino acid sequences of OrfB and the OrfB homolog is shown in FIG. 2.

The amino acid sequence alignment can be created using a known alignment program ClustalW [Nucleic Acids Research 22, 4673, (1994)]. ClustalW can be utilized from http://www.ebi.ac.uk/clustalw/ (European Bioinformatics Institute). As a parameter when creating an alignment using ClustalW, for example, default values are used.

As the mutated OrfB, more preferably, a protein in which at least one of the following substitutions of an amino acid residue in the amino acid sequence of the protein described in the above (a) or (b) is exemplified.

(i) a substitution of the amino acid residue at position 6 in the amino acid sequence of SEQ ID NO: 2 or an amino acid residue corresponding to the amino acid residue in the amino acid sequence of the OrfB homolog with serine (ii) a substitution of the amino acid residue at position 65 in the amino acid sequence of SEQ ID NO: 2 or an amino acid residue corresponding to the amino acid residue in the amino acid sequence of the OrfB homolog with leucine (iii) a substitution of the amino acid residue at position 230 in the amino acid sequence of SEQ ID NO: 2 or an amino acid residue corresponding to the amino acid residue in the amino acid sequence of the OrfB homolog with leucine, L-tryptophan, L-asparagine, glycine, L-aspartic acid, or L-alanine (iv) a substitution of the amino acid residue at position 231 in the amino acid sequence of SEQ ID NO: 2 or an amino acid residue corresponding to the amino acid residue in the amino acid sequence of the OrfB homolog with threonine (v) a substitution of the amino acid residue at position 275 in the amino acid sequence of SEQ ID NO: 2 or an amino acid residue corresponding to the amino acid residue in the amino acid sequence of the OrfB homolog with glycine The amino acid residue after the substitution may be a mutually substitutable amino acid. Hereinafter, examples of the mutually substitutable amino acid are shown. Amino acids included in the same group can be mutually substituted.

group A: leucine, isoleucine, norleucine, valine, norvaline, alanine, 2-aminobutanoic acid, methionine, O-methylserine, t-butyl glycine, t-butyl alanine, and cyclohexylalanine group B: aspartic acid, glutamic acid, isoaspartic acid, isoglutamic acid, 2-aminoadipic acid, and 2-aminosuberic acid group C: asparagine and glutamine group D: lysine, arginine, ornithine, 2,4-diaminobutanoic acid, and 2,3-diaminopropionic acid group E: proline, 3-hydroxyproline, and 4-hydroxyproline group F: serine, threonine, and homoserine group G: phenylalanine and tyrosine The amino acid to be substituted, may be either a natural type or an unnatural type. Examples of the natural type amino acid include L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, L-cysteine, and the like.

[Method for Creating Microorganism]

As a method for allowing a microorganism having an ability to produce DHA to express mutated OrfB or a mutated OrfB homolog, for example, the following (I) and (II) are exemplified.

(I) An exogenous gene encoding mutated OrfB or a mutated OrfB homolog is introduced into a microorganism having an ability to produce DHA.

(II) A mutation is introduced into a gene encoding endogenous OrfB or an OrfB homolog in a microorganism having an ability to produce DHA.

With respect to the above (I), the introduction of an exogenous gene encoding mutated OrfB or a mutated OrfB homolog includes a case where the gene is present in a cell of the host organism as an autonomously replicable plasmid, a case where a gene to be substituted in the cell is substituted with a corresponding exogenous gene, and a case where an exogenous gene encoding mutated OrfB or a mutated OrfB homolog is integrated into a region different from the gene encoding OrfB in a chromosomal DNA in the cell. Note that when an exogenous gene is introduced, it is preferred to optimize the sequence with reference to the codon usage frequency of a microorganism to be used as the host.

With respect to the above (II), a mutation can be introduced into a gene encoding endogenous OrfB or an OrfB homolog by introducing a site-directed mutation using a site-directed mutagenesis method described in, for example, Molecular Cloning, A Laboratory Manual, Third Edition, Cold Spring Harbor Laboratory Press (2001) (hereinafter abbreviated as "Molecular Cloning Third Edition"), Current Protocols in Molecular Biology, John Wiley & Sons (1987-1997) (hereinafter abbreviated as "Current Protocols in Molecular Biology"), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985), or the like.

The "gene" as used herein refers to a DNA that may contain a transcriptional regulatory region, a promoter region, and a terminator region, or the like in addition to a protein coding region. When a prokaryote such as a bacterium is used as a parent strain as a host organism, as the DNA, a plasmid in which a distance between the Shine- Dalgarno sequence that is a ribosome binding region and the start codon is adjusted to an appropriate distance (for example, 6 to 18 bases) is preferably used. In the DNA, a transcription termination factor is not always necessary for the expression of the DNA, but it is preferred to place the transcription termination sequence immediately downstream of the structural gene.

As the gene to be introduced into the host organism, for example, by preparing a recombinant gene in which the gene is inserted downstream of the promoter of an appropriate expression vector, the gene can be introduced into a host cell. The expression vector can also contain a promoter, a transcription termination signal, or a selection marker gene for selecting a transformant (for example, a drug resistance gene such as a kanamycin resistance gene, a streptomycin resistance gene, a carboxin resistance gene, a zeocin resistance gene, or a hygromycin resistance gene, a gene that complements an amino acid auxotrophic mutation such as a leucine, histidine, methionine, arginine, tryptophan, or lysine auxotrophic mutation, or the like, a gene that complements a nucleobase auxotrophic mutation such as an uracil or adenine auxotrophic mutation, or the like). In the case of an uracil auxotrophic strain, as the marker gene, for example, an orotidine-5'-phosphate decarboxylase gene (ura3 gene) or an orotidylate pyrophosphorylase gene (ura5 gene) is exemplified.

The promoter is defined as a base sequence of a DNA that initiates RNA synthesis by binding an RNA polymerase to the DNA regardless of whether it is a constitutive promoter or a regulatory promoter. A strong promoter is a promoter that initiates mRNA synthesis at a high frequency and is preferably used. A lac system, a trp system, a TAC or TRC system, major operator and promoter regions of a λ phage, a regulatory region of a fd coat protein, a promoter for a glycolytic enzyme (for example, 3-phosphoglycerate kinase or glyceraldehyde 3-phosphate dehydrogenase), glutamate decarboxylase A, or serine hydroxymethyltransferase, or the like can be used according to the properties of the host cell or the like.

In addition to the promoter and terminator sequences, as other regulatory elements, for example, a selection marker, an amplification signal, a replication origin, and the like are exemplified. As a preferred regulatory sequence, for example, sequences described in "Gene Expression Technology: Methods in Enzymology 185," Academic Press (1990) are exemplified.

The vector is not particularly limited as long as a target gene can be expressed. The types of reagents for constructing the vector, for example, restriction enzymes or ligation enzymes, or the like are also not particularly limited, and commercially available products can be used as appropriate.

The promoter when a *Labyrinthulomycetes* microorganism is used as the host organism is not particularly limited as long as it is a promoter that functions in the cells of the *Labyrinthulomycetes* microorganism, and examples thereof include an actin promoter, a tubulin promoter, an elongation factor Tu promoter, and a glycolytic gene expression promoter.

When a microorganism belonging to the genus *Escherichia* is used as the parent strain, as the expression vector, for example, pColdI (manufactured by Takara Bio, Inc.), pET21a, pCOLADuet-1, pACYCDuet-1, pCDF-1b, pRSF-1b (all manufactured by Novagen, Inc.), PMAL-c2x (manufactured by New England Biolabs, Inc.), pGEX-4T-1 (manufactured by GE Healthcare Biosciences, Inc.), pTrcHis (manufactured by Invitrogen, Inc.), pSE280 (manufactured by Invitrogen, Inc.), pGEMEX-1 (manufactured by Promega, Inc.), PQE-30 (manufactured by Qiagen, Inc.), pET-3 (manufactured by Novagen, Inc.), pTrc99A (manufactured by GE Healthcare Biosciences, Inc.), pKYP10 (JP-A-558-110600), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(+), pBluescript II KS(−) (manufactured by Stratagene Corporation), pTrS30 [prepared from *Escherichia coli* JM109/pTrS30 (Ferm BP-5407)], pTrS32 [prepared from *Escherichia coli* JM109/pTrS32 (Ferm BP-5408)], pTK31 [APPLIED AND ENVIRONMENTAL MICROBIOLOGY, 2007, Vol. 73, No. 20, pp. 6378-6385], pPAC31 (WO 98/12343), pUC19 [Gene, 33, 103 (1985)], pSTV28 (manufactured by Takara Bio, Inc.), pUC118 (manufactured by Takara Bio, Inc.), pPA1 (JP-A-S63-233798), pHSG298 (manufactured by Takara Bio, Inc.), and pUC18 (manufactured by Takara Bio, Inc.) are exemplified.

The promoter when using the above-mentioned expression vector is not particularly limited as long as it is a promoter that functions in cells of a microorganism belonging to the genus *Escherichia*, and for example, a promoter derived from *Escherichia coli*, a phage, or the like such as a trp promoter (Ptrp), a lac promoter (Plac), a PL promoter, a PR promoter, a PSE promoter, or a T7 promoter is exemplified. Further, for example, an artificially designed and modified promoter such as a promoter in which two Ptrps are connected in series, a tac promoter, a trc promoter, a lacT7 promoter, or a letI promoter is exemplified.

When a coryneform bacterium is used as the parent strain, examples of the expression vector include pCG1 (JP-A-S57-134500), pCG2 (JP-A-S58-35197), pCG4 (JP-A-S57-183799), pCG11 (JP-A-S57-134500), pCG116, pCE54, pCB101 (all in JP-A-S58-105999), pCE51, pCE52, pCE53 [all in Molecular and General Genetics, 196, 175 (1984)], and the like.

The promoter when using the above-mentioned expression vector is not particularly limited as long as it is a promoter that functions in cells of a coryneform bacterium, and for example, a P54-6 promoter [Appl. Microbiol. Biotechnol., 53, 674-679 (2000)] is exemplified.

When a yeast strain is used as the parent strain, examples of the expression vector include YEp13 (ATCC 37115), YEp24 (ATCC 37051), YCp51 (ATCC 37419), pHS19, pHS15, and the like.

The promoter when using the above-mentioned expression vector is not particularly limited as long as it is a promoter that functions in cells of a yeast strain, and for example, promoters such as a PHO5 promoter, a PGK promoter, a GAP promoter, an ADH promoter, a gal 1 promoter, a gal 10 promoter, a heat shock polypeptide promoter, an MFα1 promoter, and a CUP1 promoter are exemplified.

As a method of integrating a recombinant gene into the chromosome of a host organism, a homologous recombination method can be used. As the homologous recombination method, for example, a method of introducing a recombinant gene by utilizing a homologous recombination system that can be produced by ligating the gene to a plasmid DNA having a drug resistance gene which cannot be autonomously replicated in a parent strain into which the gene is desired to be introduced is exemplified. As a method utilizing homologous recombination frequently used in *Escherichia coli*, a method of introducing a recombinant gene by utilizing a homologous recombination system of a lambda phage [Proc. Natl. Acad. Sci. USA, 97, 6641-6645 (2000)] is exemplified.

Further, a microorganism in which a target region on the chromosomal DNA of a parent strain has been substituted with a recombinant DNA can be obtained using a selection method utilizing the fact that *E. coli* becomes sensitive to sucrose by *Bacillus subtilis* levansucrase integrated on the chromosome together with the recombinant gene, or a selection method utilizing the fact that *E. coli* becomes sensitive to streptomycin by integrating a wild-type rpsL gene into *E. coli* having a streptomycin-resistant mutant rpsL gene [Mol. Microbiol., 55, 137 (2005), Biosci. Biotechnol. Biochem., 71, 2905 (2007)], or the like.

In addition, as the homologous recombination method, for example, an ATMT method mediated by an *Agrobacterium* [Appl. Environ. Microbiol., (2009), vol. 75, pp. 5529-5535] is exemplified. Further, an improved ATMT method or the like is included, and the method is not limited thereto as long as a transformant that stably carries a target trait can be obtained.

As a method of introducing a gene to be introduced as a plasmid autonomously replicable in a host organism, for example, a method using calcium ions [Proc. Natl. Acad. Sci. USA, 69, 2110 (1972)], a protoplast method (JP-A-S63-248394), an electroporation method [Nucleic Acids Res., 16, 6127 (1988)], and the like are exemplified.

It can be confirmed that a microorganism obtained by the above-mentioned method is a target microorganism by culturing the microorganism and detecting EPA accumulated in the resulting culture by gas chromatography.

In the microorganism of the present invention, for example, the EPA/DHA ratio in the final product (PUFA) to be produced when the microorganism is cultured at 20° C. for 48 hours is preferably 0.1 or more, more preferably 0.2 or more, further more preferably 0.5 or more as measured by gas chromatography-mass spectrometry described later in Examples.

[Method for Producing EPA or EPA-Containing Composition]

The present invention includes a method for producing EPA or an EPA-containing composition (hereinafter referred to as the production method of the present invention), characterized by culturing the microorganism created above in a culture medium so as to produce and accumulate EPA or an EPA-containing composition in a culture, and collecting EPA or the EPA-containing composition from the culture.

As the EPA-containing composition, for example, an EPA-containing oil or fat or an EPA-containing phospholipid, preferably an EPA-containing oil or fat is exemplified. The culture of the microorganism can be obtained by inoculating the microorganism into an appropriate culture medium and culturing the microorganism according to a conventional method.

As the culture medium, any known culture medium containing a carbon source, a nitrogen source, and an inorganic salt, or the like can be used. For example, as the carbon source, in addition to carbohydrates such as glucose, fructose, and galactose, oils and fats such as oleic acid and soybean oil, glycerol, sodium acetate, and the like can be exemplified. These carbon sources can be used, for example, at a concentration of 20 to 300 g per liter of the culture medium. According to a particularly preferred embodiment, the culture can be continuously carried out by feeding the carbon source after the initial carbon source is consumed. By carrying out the culture under such conditions, the amount of the carbon source to be consumed is increased, so that the production amount of the EPA-containing composition can be improved.

Further, examples of the nitrogen source include organic nitrogen such as yeast extract, corn steep liquor, polypeptone, sodium glutamate, and urea, and inorganic nitrogen such as ammonium acetate, ammonium sulfate, ammonium chloride, sodium nitrate, ammonium nitrate, and ammonia. As the inorganic salt, potassium phosphate or the like can be used in combination as appropriate.

The culture medium containing the above-mentioned respective components is preferably used after adjusting the pH within a range of 4.0 to 9.5 by adding an appropriate acid or base, followed by sterilization in an autoclave. The culture temperature is generally from 10 to 45° C., preferably from 20 to 37° C. The culture temperature is preferably controlled to a culture temperature at which an EPA-containing composition can be produced. The pH during culture is generally from 3.5 to 9.5, preferably from 4.5 to 9.5. The particularly preferred pH varies depending on the purpose, and is from 5.0 to 8.0 in order to produce a large amount of an oil or fat.

The culture time can be set to, for example, 2 to 7 days, and the culture can be carried out by aeration and agitation culture or the like. A method of separating the culture solution and the microorganism from the culture can be carried out by a conventional method known to those skilled in the art, for example, by centrifugation, filtration, or the like. The microorganism separated from the above culture is homogenized using, for example, ultrasonic waves, a dyno mill, or the like, followed by solvent extraction with, for example, chloroform, hexane, butanol, or the like, whereby the EPA-containing composition is obtained.

The EPA-containing composition produced by the above-mentioned production method is subjected to, for example, a method such as a low temperature solvent fractionation method [Koretaro Takahashi, Journal of Japan Oil Chemist's Society, 40: 931-941 (1991)] or a method of releasing and removing short-chain fatty acids with a hydrolase such as a lipase [Koretaro Takahashi, Journal of Japan Oil Chemist's Society, 40: 931-941 (1991)] so as to concentrate the EPA-containing composition, whereby the EPA-containing composition having a high EPA content can be obtained.

EPA can be produced by separating and collecting EPA from an EPA-containing composition. For example, after preparing a mixed fatty acid containing EPA from an EPA-containing composition by a hydrolysis method, EPA is separated and collecting by, for example, a urea addition method, a cooling separation method, high performance liquid chromatography, supercritical chromatography, or the like, whereby EPA can be produced.

Further, an EPA alkyl ester can be produced by separating and collecting the EPA alkyl ester from an EPA-containing composition. The EPA alkyl ester is not particularly limited as long as it is an EPA alkyl ester, but preferably an EPA ethyl ester is exemplified.

In order to separate and collect an EPA alkyl ester from an EPA-containing composition, for example, after preparing a mixed fatty acid alkyl ester containing an EPA alkyl ester from the EPA-containing composition by an alcoholysis method, the EPA alkyl ester can be separated and collected by, for example, a urea addition method, a cooling separation method, high performance liquid chromatography, supercritical chromatography, or the like.

EXAMPLES

Hereinafter, Examples will be shown, however, the present invention is not limited to the following Examples.

Example 1

Production of EPA Using *E. Coli* that Produces Mutated OrfB [1]
(1) Creation of Respective Expression Plasmids
[Creation of OrfA Protein Expression Plasmid]

An expression plasmid pET21-orfA having a DNA (a DNA composed of the base sequence represented by SEQ ID NO: 4) encoding OrfA protein derived from *Schizochy-*

*trium* sp. (ATCC 20888) strain was obtained by a method similar to that of Hayashi et al. (Sci. Rep., 2016, 6, 35441).
[Creation of OrfC Protein Expression Plasmid]

PCR was carried out using the genomic DNA of *Aurantiochytrium* sp. OH4 strain extracted by a conventional method as a template and primers represented by SEQ ID NOS: 7 and 8, whereby a DNA fragment containing a DNA (a DNA composed of the base sequence represented by SEQ ID NO: 3) encoding OrfC protein was obtained. The obtained DNA and an *E. coli* vector pCOLADuet-1 (manufactured by Merck Millipore Corporation) were each treated with restriction enzymes NdeI and MfeI, and the resulting restriction enzyme-treated fragments were ligated to each other, whereby an OrfC protein expression plasmid pCOLA-OH4_orfC derived from *Aurantiochytrium* sp. OH4 strain was obtained.

[Creation of HetI Protein Expression Plasmid]

An expression plasmid pSTV-hetI having a DNA (a DNA composed of the base sequence represented by SEQ ID NO: 5) encoding HetI protein derived from *Nostoc* sp. PCC7120 (ATCC 27893) strain was obtained by a method similar to that of Hayashi et al. (Sci. Rep., 2016, 6, 35441).

(2) Construction of DNA Library Encoding Mutated OrfB
[Creation of Wild-Type OrfB Expression Plasmid]

An OrfB expression plasmid pCDF-orfB1 (Sci. Rep., 2016, 6, 35441) derived from *Schizochytrium* sp. (ATCC 20888) strain was treated with AgeI, whereby an AgeI-treated fragment was obtained, and the ends of the AgeI-treated fragment were blunted using Blunting high kit (manufactured by Toyobo Co., Ltd.), and then self-ligated. In this manner, pCDF-orfB1' in which the AgeI recognition sequence downstream of the T7 terminator of pCDF-orfB1 was deleted was obtained.

Subsequently, overlap extension PCR was carried out using the genomic DNA of *Aurantiochytrium* sp. OH4 strain extracted by a conventional method as a template and primers represented by SEQ ID NOS: 9, 10, 11, and 12, whereby a DNA fragment containing a DNA (a DNA composed of the base sequence represented by SEQ ID NO: 1) encoding OrfB was amplified. In the amplified DNA fragment, the base at position 4713 in the cording region has been changed from adenine to thymidine, and the NdeI recognition sequence (the base sequence at positions 4712 to 4717) has been deleted. The obtained DNA fragment and pCDF-orfB1' were each treated with restriction enzymes NdeI and EcoRI, and the resulting restriction enzyme-treated fragments were ligated to each other, whereby pCDF-OH4_orfB was obtained.

Subsequently, overlap extension PCR was carried out using pCDF-OH4_orfB as a template and primers represented by SEQ ID NOS: 9, 12, 13, and 14, whereby a DNA fragment containing a DNA encoding OrfB was amplified. In the DNA fragment, the base at position 2625 in the cording region has been changed from guanine to adenine, and a SphI recognition sequence has been introduced into the base sequence at positions 2623 to 2628. The obtained DNA fragment and pCDF-orfB1' were each treated with restriction enzymes NdeI and EcoRI, and the resulting restriction enzyme-treated fragments were ligated to each other, whereby a plasmid pCDF-OH4_orfBs that expresses wild-type OrfB derived from *Aurantiochytrium* sp. OH4 strain was obtained.

[Construction of DNA Library Encoding Mutated OrfB]

Subsequently, error-prone PCR was carried out with TAKARA TAQ™ Hot Start Version (manufactured by Takara Bio, Inc.) using pCDF-OH4_orfBs as a template and primers represented by SEQ ID NOS: 15 and 16. In the error-prone PCR, in order to induce a mutation, the concentration of MgCl in the PCR reaction solution was set to 5 mM.

The DNA fragment obtained by the error-prone PCR was purified, and then treated with restriction enzymes NdeI and AgeI, and ligated to pCDF-OH4_orfBs having been treated with the same restriction enzymes. In this manner, a DNA library encoding mutated OrfB was constructed.

(3) Evaluation of Productivity of EPA

*E. coli* BLR(DE3)ΔfadE strain in which a gene encoding acyl-CoA dehydrogenase FadE (a protein composed of the amino acid sequence represented by SEQ ID NO: 6) has been deleted was created by a method similar to that of Hayashi et al. (Sci. Rep., 2016, 6, 35441).

*E. coli* BLR(DE3)ΔfadE strain was transformed using pET21-orfA, pCOLA-OH4_orfC, and pSTV-hetI, and pCDF-OH4_orfBs or the DNA library encoding mutated OrfB.

The obtained *E. coli* was inoculated into 2 mL of TERRIFIC BROTH™ medium (manufactured by Becton, Dickinson and Company) containing 100 mg/L ampicillin, 20 mg/L kanamycin, 30 mg/L chloramphenicol, and 20 mg/L streptomycin, and subjected to shaking culture at 30° C. for 16 hours.

1 mL of the obtained culture solution was inoculated into a 200-mL flask equipped with a blade containing 20 mL of newly prepared TERRIFIC BROTH™ medium (manufactured by Becton, Dickinson and Company) containing 100 mg/L ampicillin, 20 mg/L kanamycin, 30 mg/L chloramphenicol, 20 mg/L streptomycin, and 1 mM IPTG, and the *E. coli* was cultured at 230 rpm and 20° C. for 48 hours.

After culture, the culture solution was collected, and a lipid was extracted by a Bligh-Dyer method [Bligh, e. G. and Dyer, W. J. (1959) Can. J. Biochem. Physiol. 37, 911-917], and then, a fatty acid was methylated using a boron trifluoride-methanol solution, and analyzed by gas chromatography-mass spectrometry. The abundance of DHA or EPA in the culture solution was calculated from the area of the peak corresponding to DHA methyl ester or EPA methyl ester in the gas chromatography-mass spectrometry, and further, the abundance ratio of EPA to DHA was also calculated.

As a result, the *E. coli* that produces wild-type OrfB did not produce EPA, whereas among the *E. coli* strains transformed with the DNA library encoding mutated OrfB, a strain that produced EPA was confirmed.

When the base sequence of the DNA encoding the mutated OrfB produced by the *E. coli* that produced EPA was determined, L-phenylalanine at position 230 in the amino acid sequence of OrfB was substituted with L-leucine.

(4) Acquisition of Mutated OrfB with Additional Mutation

In addition, error-prone PCR was carried out in the same manner as described above using the DNA encoding mutated OrfB composed of an amino acid sequence in which L-phenylalanine at position 230 has been substituted with L-leucine as a template, and the resulting fragment was introduced into *E. coli* BLR(DE3)ΔfadE strain in the same manner as described above, and the productivity of EPA was confirmed.

As a result, a strain in which the productivity of EPA was further improved as compared with the *E. coli* that produces mutated OrfB composed of an amino acid sequence in which L-phenylalanine at position 230 has been substituted with L-leucine obtained above was confirmed.

When the base sequence of the DNA encoding the mutated OrfB expressed by the *E. coli* in which the productivity of EPA was further improved was determined, in the amino acid sequence of OrfB, L-asparagine at position 6 was substituted with L-serine, and L-phenylalanine at position 65 was substituted with L-leucine in addition to the substitution of L-phenylalanine at position 230 with L-leucine.

A summary of the results of measuring EPA, DHA, and DPA in the culture solution is shown in Table 1.

TABLE 1

| Mutation site in OrfB protein produced by E. coli | EPA [µg/mL/OD] | DHA [µg/mL/OD] | DPA (ω-6) [µg/mL/OD] | DPA (ω-3) [µg/mL/OD] | EPA/DHA ratio |
|---|---|---|---|---|---|
| Non (wild type) | N.D. | 1.10 ± 0.04 | 0.26 ± 0.01 | N.D. | 0 |
| F230L | 0.10 ± 0.01 | 0.68 ± 0.07 | 0.06 ± 0.00 | 0.06 ± 0.01 | 0.15 |
| N6S/F65L/F230L | 0.38 ± 0.05 | 1.12 ± 0.14 | 0.09 + 0.01 | 0.12 ± 0.02 | 0.34 |

As shown in Table 1, it was found that by using the *E. coli* that produces mutated OrfB in which the amino acid residue at position 230 in the amino acid sequence of OrfB was substituted with L-leucine or mutated OrfB in which the amino acid residue at position 6 was substituted with L-serine, the amino acid residue at position 65 was substituted with L-leucine, and the amino acid residue at position 230 was substituted with L-leucine, EPA can be efficiently produced as compared with the case where the *E. coli* that produces wild-type OrfB was used.

Example 2

Production of EPA Using *E. Coli* that Produces Mutated OrfB [2]

(1) Creation of Respective Expression Plasmids

PCR was carried out using pCDF-OH4_orfB obtained in Example 1 (2) as a template and primers represented by SEQ ID NOS: 9 and 17, whereby a DNA fragment containing a DNA encoding an N-terminal region of the KS domain of OrfB was amplified.

Further, PCR was carried out using pCDF-OH4_orfB as a template and a primer represented by SEQ ID NO: 16 and a primer represented by SEQ ID NO: 18, 19, 20, 21, or 22, whereby a DNA fragment containing a DNA encoding a C-terminal region of the KS domain of mutated OrfB in which the amino acid residue at position 230 in the amino acid sequence of OrfB was substituted with L-tryptophan, L-asparagine, glycine, L-aspartic acid, or L-alanine was amplified.

Overlap extension PCR was carried out using the obtained DNA fragment encoding an N-terminal region or a C-terminal region of the KS domain and primers represented by SEQ ID NOS: 9 and 16, whereby a DNA fragment containing a DNA encoding the full length of the KS domain of mutated OrfB in which the amino acid residue at position 230 in the amino acid sequence of OrfB was substituted with L-tryptophan, L-asparagine, glycine, L-aspartic acid, or L-alanine was obtained.

The DNA fragment and pCDF-OH4_orfBs were each treated with restriction enzymes NdeI and AgeI, and the resulting restriction enzyme-treated fragments were ligated to each other, whereby pCDF-OH4_orfB-F230W, pCDF-OH4_orfB-F230N, pCDF-OH4_orfB-F230G, pCDF-OH4_orfB-F230D, and pCDF-OH4_orfB-F230A were obtained.

Further, by using the *E. coli* obtained in Example 1 (3), a plasmid pCDF-OH4_orfB-F230L having a DNA encoding mutated OrfB in which the amino acid residue at position 230 in the amino acid sequence of OrfB was substituted with L-leucine was obtained.

(2) Production of EPA

*E. coli* BLR(DE3)ΔfadE strain was transformed using pET21-orfA, pCOLA-OH4_orfC, and pSTV-hetI, and the expression plasmid for wild-type OrfB or any of the 6 types of mutated OrfB (pCDF-OH4_orfBs, pCDF-OH4_orfB-F230L, pCDF-OH4_orfB-F230W, pCDF-OH4_orfB-F230N, pCDF-OH4_orfB-F230G, pCDF-OH4_orfB-F230D, or pCDF-OH4_orfB-F230A).

The obtained *E. coli* was inoculated into 2 mL of TERRIFIC BROTH™ medium (manufactured by Becton, Dickinson and Company) containing 100 mg/L ampicillin, 20 mg/L kanamycin, 30 mg/L chloramphenicol, and 20 mg/L streptomycin, and subjected to shaking culture at 30° C. for 16 hours.

1 mL of the obtained culture solution was inoculated into a 200-mL flask equipped with a blade containing 20 mL of newly prepared TERRIFIC BROTH™ medium (manufactured by Becton, Dickinson and Company) containing 100 mg/L ampicillin, 20 mg/L kanamycin, 30 mg/L chloramphenicol, 20 mg/L streptomycin, and 1 mM IPTG, and the *E. coli* was cultured at 230 rpm and 20° C. for 48 hours.

After culture, the culture solution was collected, and a lipid was extracted by a Bligh-Dyer method, and then, a fatty acid was methylated using a boron trifluoride-methanol solution, and analyzed by gas chromatography-mass spectrometry.

The results of measuring EPA, DHA, and DPA in the culture solution are shown in Table 2.

TABLE 2

| Mutation site in OrfB protein produced by E. coli | EPA [µg/mL/OD] | DHA [µg/mL/OD] | DPA (ω-6) [µg/mL/OD] | DPA (ω-3) [µg/mL/OD] | EPA/DHA ratio |
|---|---|---|---|---|---|
| Non (wild type) | N.D. | 0.93 ±0.08 | 0.46 ±0.04 | N.D. | 0 |
| F230L | 0.68 ± 0.10 | 3.6 ± 0.5 | 0.32 ± 0.05 | 0.31 ± 0.05 | 0.19 |
| F230W | N.D. | 0.029 ± 0.002 | N.D. | N.D. | 0 |
| F230N | 0.39 ± 0.04 | 3.36 ± 0.12 | 0.84 ± 0.02 | N.D. | 0.12 |
| F230G | 0.55 ± 0.13 | 3.04 ± 0.5 | 0.78 ± 0.06 | N.D. | 0.18 |

TABLE 2-continued

| Mutation site in OrfB protein produced by E. coli | EPA [µg/mL/OD] | DHA [µg/mL/OD] | DPA (ω-6) [µg/mL/OD] | DPA (ω-3) [µg/mL/OD] | EPA/DHA ratio |
|---|---|---|---|---|---|
| F230D | 0.77 + 0.07 | 4.4 ± 0.3 | 1.01 ± 0.07 | N.D. | 0.18 |
| F230A | 0.31 ± 0.04 | 2.8 ± 0.4 | 0.69 ± 0.1 | N.D. | 0.11 |

As shown in Table 2, it was found that even if using the *E. coli* that produces mutated OrfB in which the amino acid residue at position 230 in the amino acid sequence of OrfB was substituted with L-tryptophan, L-asparagine, glycine, L-aspartic acid, or L-alanine, EPA can be efficiently produced as compared with the case where the *E. coli* that produces wild-type OrfB was used in the same manner as in the case where mutated OrfB in which the amino acid residue at position 230 in the amino acid sequence of OrfB was substituted with L-leucine was used.

Example 3

Production of EPA Using *E. Coli* that Produces Mutated OrfB [3]
(1) Creation of Respective Expression Plasmids
[Creation of pCDF-OH4_orfB-N6S-F230L]

PCR was carried out using pCDF-OH4_orfB-F230L as a template and primers represented by SEQ ID NOS: 23 and 16, whereby a DNA fragment containing a DNA encoding the KS domain of OrfB was obtained. The obtained DNA fragment and pCDF-OH4_orfB-F230L were each treated with restriction enzymes NdeI and AgeI, and the resulting restriction enzyme-treated fragments were ligated to each other, whereby pCDF-OH4_orfB-N6S-F230L was obtained.

The pCDF-OH4_orfB-N6S-F230L has a DNA encoding an amino acid sequence in which in the amino acid sequence of OrfB derived from *Aurantiochytrium* sp. OH4 strain, the amino acid residue at position 6 was substituted with L-serine and the amino acid residue at position 230 was substituted with L-leucine.
[Creation of pCDF-OH4_orfB-F65L-F230L]

Overlap extension PCR was carried out using pCDF-OH4_orfB-F230L as a template and primers represented by SEQ ID NOS: 24, 25, 26, and 16, whereby a DNA fragment containing a DNA encoding the KS domain of OrfB was obtained. The obtained DNA fragment and pCDF-OH4_orfB-F230L were each treated with restriction enzymes NdeI and AgeI, and the resulting restriction enzyme-treated fragments were ligated to each other, whereby pCDF-OH4_orfB-F65L-F230L was obtained.

The pCDF-OH4_orfB-F65L-F230L has a DNA encoding an amino acid sequence in which in the amino acid sequence of OrfB derived from *Aurantiochytrium* sp. OH4 strain, the amino acid residue at position 65 was substituted with L-leucine and the amino acid residue at position 230 was substituted with L-leucine.
[Creation of pCDF-OH4_orfB-N6S-F65L-F230L]

A plasmid was extracted from the *E. coli* that produces OrfB in which L-phenylalanine at position 230 was substituted with L-leucine, L-asparagine at position 6 was substituted with L-serine, and L-phenylalanine at position 65 was substituted with L-leucine obtained in Example 1 (4), whereby pCDF-OH4_orfB-N6S-F65L-F230L was obtained.

The pCDF-OH4_orfB-N6S-F65L-F230L has a DNA encoding an amino acid sequence in which in the amino acid sequence of OrfB derived from *Aurantiochytrium* sp. OH4 strain, the amino acid residue at position 6 was substituted with L-serine, the amino acid residue at position 65 was substituted with L-leucine, and the amino acid residue at position 230 was substituted with L-leucine.
(2) Production of EPA

*E. coli* BLR(DE3)ΔfadE strain was transformed using pET21-orfA, pCOLA-OH4_orfC, and pSTV-hetI, and the expression plasmid for wild-type OrfB or any of the 4 types of mutated OrfB (pCDF-OH4_orfBs, pCDF-OH4_orfB-F230L, pCDF-OH4_orfB-N6S-F230L, pCDF-OH4_orfB-F65L-F230L, or pCDF-OH4_orfB-N6S-F65L-F230).

The obtained *E. coli* was inoculated into 2 mL of TERRIFIC BROTH™ medium (manufactured by Becton, Dickinson and Company) containing 100 mg/L ampicillin, 20 mg/L kanamycin, 30 mg/L chloramphenicol, and 20 mg/L streptomycin, and subjected to shaking culture at 30° C. for 16 hours.

1 mL of the obtained culture solution was inoculated into a 200-mL flask equipped with a blade containing 20 mL of newly prepared TERRIFIC BROTH™ medium (manufactured by Becton, Dickinson and Company) containing 100 mg/L ampicillin, 20 mg/L kanamycin, 30 mg/L chloramphenicol, 20 mg/L streptomycin, and 1 mM IPTG, and the *E. coli* was cultured at 230 rpm and 20° C. for 48 hours.

After culture, the culture solution was collected, and a lipid was extracted by a Bligh-Dyer method, and then, a fatty acid was methylated using a boron trifluoride-methanol solution, and analyzed by gas chromatography-mass spectrometry.

The results of measuring EPA, DHA, and DPA in the culture solution are shown in Table 3.

TABLE 3

| Mutation site in OrfB protein produced by E. coli | EPA [µg/mL/OD] | DHA [µg/mL/OD] | DPA (ω-6) [µg/mL/OD] | EPA/DHA ratio |
|---|---|---|---|---|
| Non (wild type) | N.D. | 3.66 ± 0.08 | 1.57 ± 0.04 | 0 |
| F230L | 1.04 ± 0.16 | 5.65 ± 0.89 | 0.53 ± 0.10 | 0.18 |
| N6S/F230L | 1.16 ± 0.14 | 5.36 ± 0.75 | 0.54 ± 0.15 | 0.22 |
| F65L/F230L | 1.59 ± 0.07 | 5.94 ± 0.12 | 0.48 ± 0.03 | 0.27 |
| N6S/F65L/F230L | 1.91 ± 0.18 | 6.36 ± 0.42 | 0.56 ± 0.03 | 0.30 |

As shown in Table 3, it was found that when using the *E. coli* that produces mutated OrfB in which in the amino acid sequence of OrfB, the amino acid residue at position 6 and/or the amino acid residue at position 65 were/was substituted with L-serine and L-leucine, respectively, in addition to the amino acid residue at position 230, EPA can be more efficiently produced as compared with the case where the *E. coli* that produces mutated OrfB in which the amino acid residue at position 230 in the amino acid sequence of OrfB was substituted with L-leucine was used.

Example 4

Production of EPA Using *E. Coli* that Produces Mutated OrfB [4]

Error-prone PCR was carried out in the same manner as in Example 1 (2) using the DNA encoding mutated OrfB composed of an amino acid sequence in which L-phenylalanine at position 230 has been substituted with L-leucine and L-phenylalanine at position 65 has been substituted with L-leucine obtained in Example 3 as a template, and the resulting fragment was introduced into *E. coli* BLR(DE3) ΔfadE strain in the same manner as in Example 1 (3), and the productivity of EPA was confirmed.

As a result, a strain in which the productivity of EPA was further improved as compared with the *E. coli* that produces mutated OrfB composed of an amino acid sequence in which L-phenylalanine at position 230 has been substituted with L-leucine and L-phenylalanine at position 65 has been substituted with L-leucine was confirmed.

When the base sequence of the DNA encoding the mutated OrfB expressed by the *E. coli* in which the productivity of EPA was improved was determined, in the amino acid sequence of OrfB, L-isoleucine at position 231 was substituted with L-threonine and L-aspartic acid at position 275 was substituted with L-glycine in addition to the substitution of L-phenylalanine at position 230 with L-leucine and the substitution of L-phenylalanine at position 65 with L-leucine.

A summary of the results of measuring EPA, DHA, and DPA in the culture solution is shown in Table 4.

TABLE 4

| Mutation site in OrfB protein produced by *E. coli* | EPA [μg/mL/OD] | DHA [μg/mL/OD] | DPA (ω-6) [μg/mL/OD] | DPA (ω-3) [μg/mL/OD] | EPA/DHA ratio |
| --- | --- | --- | --- | --- | --- |
| Non (wild type) | N.D. | 1.67 ± 0.39 | 1.77 ± 0.17 | N.D. | 0 |
| F65L/F230L | 1.09 + 0.07 | 4.07 ± 0.21 | 0.36 ± 0.03 | 0.31 ± 0.02 | 0.27 |
| F65L/F230L/ I231T/D275G | 1.92 ± 0.25 | 1.79 ± 0.21 | 0.04 ± 0.01 | 0.21 ± 0.02 | 1.07 |

As shown in Table 4, it was found that by using the *E. coli* that produces mutated OrfB in which in the amino acid sequence of OrfB, the amino acid residue at position 231 was substituted with L-threonine and the amino acid residue at position 275 was substituted with glycine in addition to the amino acid residue at position 230 and the amino acid residue at position 65, EPA can be more efficiently produced as compared with the case where the *E. coli* that produces mutated OrfB in which in the amino acid sequence of OrfB, the amino acid residue at position 230 and the amino acid residue at position 65 were each substituted with L-leucine was used.

The present invention has been described in detail with reference to the specific aspects, but it is obvious for those skilled in the art that various changes and modifications can be made without departing from the spirit and scope of the invention. The present application is based on a Japanese Patent Application (Patent Application No. 2018-151234) filed on Aug. 10, 2018, which is incorporated by reference in its entirety. Also, all references cited herein are incorporated in their entirety.

The invention claimed is:

1. A microorganism having an ability to produce docosahexaenoic acid (DHA), wherein the microorganism contains a mutated OrfB protein composed of an amino acid sequence represented by SEQ ID NO: 2 except for at least one amino acid substitution selected from the group consisting of: N6S, F65L, F230L/N/G/D/A, I231T, and D275G, and wherein the mutated OrfB gives the microorganism ability to produce eicosapentaenoic acid (EPA).

2. A microorganism containing a mutated OrfB protein composed of an amino acid sequence represented by SEQ ID NO: 2 except that at least one amino acid at position 6, 65, 230, 231 or 275 has been substituted with another amino acid.

3. The microorganism according to claim 1, wherein the microorganism having an ability to produce DHA is a Labyrinthulomycetes microorganism.

4. The microorganism according to claim 3, wherein the Labyrinthulomycetes microorganism is a Labyrinthulomycetes microorganism belonging to the genus Aurantiochytrium, the genus Thraustochytrium, the genus Ulkenia, the genus Parietichytrium, the genus Labyrinthula, the genus Aplanochytrium, the genus Oblongichytrium, or the genus Schizochytrium.

5. The microorganism according to claim 1, wherein the microorganism having an ability to produce DHA is a microorganism in which genes encoding respective domains described in the following (a) to (j) having an activity of synthesizing DHA have been introduced into a microorganism that does not have a DHA metabolic pathway:
(a) a β-ketoacyl-ACP synthase (hereinafter referred to as KS) domain;
(b) a malonyl-CoA:ACP acyltransferase (hereinafter referred to as MAT) domain;
(c) an acyl carrier protein (ACP) domain;
(d) a ketoreductase (hereinafter referred to as KR) domain;
(e) a polyketide synthase dehydratase (hereinafter referred to as PS-DH) domain;
(f) a chain elongation factor (hereinafter, referred to as CLF) domain;
(g) an acyltransferase (hereinafter referred to as AT) domain;
(h) a FabA-like β-hydroxyacyl-ACP dehydratase (hereinafter referred to as FabA-DH) domain;
(i) an enoyl-ACP reductase (hereinafter referred to as ER) domain; and
(j) a phosphopantetheine transferase (hereinafter referred to as PPT) domain.

6. The microorganism according to claim 5, wherein the microorganism that does not have a DHA metabolic pathway is a microorganism belonging to the genus Escherichia, the genus Bacillus, the genus Corynebacterium, the genus Yarrowia, the genus Saccharomyces, the genus Candida, or the genus Pichia.

7. A method for producing EPA or an EPA-containing composition, comprising:
culturing the microorganism according to claim 1 in a culture medium so as to produce and accumulate EPA or an EPA-containing composition in a culture, and
collecting EPA or the EPA-containing composition from the culture.

8. The microorganism according to claim 2, wherein the microorganism is a Labyrinthulomycetes microorganism.

9. The microorganism according to claim 8, wherein the Labyrinthulomycetes microorganism is a Labyrinthulomycetes microorganism belonging to the genus Aurantiochytrium, the genus Thraustochytrium, the genus Ulkenia, the genus Parietichytrium, the genus Labyrinthula, the genus Aplanochytrium, the genus Oblongichytrium, or the genus Schizochytrium.

10. The microorganism according to claim 2, wherein the microorganism does not naturally have a DHA metabolic pathway and has been modified to be able to synthesize DHA by introducing genes encoding domains (a) to (j):
(a) a β-ketoacyl-ACP synthase (hereinafter referred to as KS) domain;
(b) a malonyl-CoA:ACP acyltransferase (hereinafter referred to as MAT) domain;
(c) an acyl carrier protein (ACP) domain;
(d) a ketoreductase (hereinafter referred to as KR) domain;
(e) a polyketide synthase dehydratase (hereinafter referred to as PS-DH) domain;
(f) a chain elongation factor (hereinafter, referred to as CLF) domain;
(g) an acyltransferase (hereinafter referred to as AT) domain;
(h) a FabA-like β-hydroxyacyl-ACP dehydratase (hereinafter referred to as FabA-DH) domain;
(i) an enoyl-ACP reductase (hereinafter referred to as ER) domain; and
(j) a phosphopantetheine transferase (hereinafter referred to as PPT) domain.

11. The microorganism according to claim 10, wherein the microorganism that does not have a DHA metabolic pathway is a microorganism belonging to the genus Escherichia, the genus Bacillus, the genus Corynebacterium, the genus Yarrowia, the genus Saccharomyces, the genus Candida, or the genus Pichia.

12. A method comprising culturing the microorganism according to claim 2 in a culture medium.

* * * * *

SEQUENCE LISTING

```
<160> NUMBER OF SEQ ID NOS: 31

<210> SEQ ID NO 1
<211> LENGTH: 6105
<212> TYPE: DNA
<213> ORGANISM: Aurantiochytrium sp. OH4
<220> FEATURE:
<221> NAME/KEY: CDS
<222> LOCATION: (1)..(6105)

<400> SEQUENCE: 1 atg gcc tct cgc aag aat gtg agc gct gct cac gaa atg cac gac gag      48
Met Ala Ser Arg Lys Asn Val Ser Ala Ala His Glu Met His Asp Glu
1               5                   10                  15 aag cgc att gcc gtg gtg ggc atg gcc gtg caa tac gcg ggc tgc aaa      96
Lys Arg Ile Ala Val Val Gly Met Ala Val Gln Tyr Ala Gly Cys Lys
            20                  25                  30 gac aag gaa gag ttc tgg aaa gta gtc atg ggc ggt gag gct gca tgg      144
Asp Lys Glu Glu Phe Trp Lys Val Val Met Gly Gly Glu Ala Ala Trp
        35                  40                  45
```

| | | |
|---|---|---|
| act aag att agc gat aaa cgc ctc gga tcc aac aag cga gcc gag cac<br>Thr Lys Ile Ser Asp Lys Arg Leu Gly Ser Asn Lys Arg Ala Glu His<br>    50                        55                      60 | | 192 |
| ttc aaa gca gag cgt agc aaa ttt gca gat acc ttt tgc aac gag aac<br>Phe Lys Ala Glu Arg Ser Lys Phe Ala Asp Thr Phe Cys Asn Glu Asn<br>65                     70                     75                     80 | | 240 |
| tac ggc tgc gtc gat gac tcc gtc gat aac gaa cac gag ctt ctc ctc<br>Tyr Gly Cys Val Asp Asp Ser Val Asp Asn Glu His Glu Leu Leu Leu<br>                     85                     90                        95 | | 288 |
| aag ctc tcc aag aag gct ctc tcc gag aca tcg gtc tcc gac tct aca<br>Lys Leu Ser Lys Lys Ala Leu Ser Glu Thr Ser Val Ser Asp Ser Thr<br>            100                 105                110 | | 336 |
| agg tgc ggt att gtg agc gga tgc ctg tcc ttt ccc atg gac aac ctc<br>Arg Cys Gly Ile Val Ser Gly Cys Leu Ser Phe Pro Met Asp Asn Leu<br>              115                 120                125 | | 384 |
| cag ggc gaa ctc ctc aat gtg tac caa aac cac gtc gaa aag aaa ctc<br>Gln Gly Glu Leu Leu Asn Val Tyr Gln Asn His Val Glu Lys Lys Leu<br>      130                 135                140 | | 432 |
| ggc gct cgc gtc ttc aag gat gcc tcc aag tgg tcc gag cgt gag cag<br>Gly Ala Arg Val Phe Lys Asp Ala Ser Lys Trp Ser Glu Arg Glu Gln<br>145                   150                 155                160 | | 480 |
| tcg cag aac ccc gag gct ggt gac cgc cgc atc ttt atg gac ccg gca<br>Ser Gln Asn Pro Glu Ala Gly Asp Arg Arg Ile Phe Met Asp Pro Ala<br>                 165                 170                175 | | 528 |
| tcc ttc gta gca gaa gag ctt aac ctc ggt cct ctt cac tac tct gtc<br>Ser Phe Val Ala Glu Glu Leu Asn Leu Gly Pro Leu His Tyr Ser Val<br>            180                 185                190 | | 576 |
| gat gct gcc tgt gcc acc gcc ctt tac gtc ctt cgc ctc gcc cag gac<br>Asp Ala Ala Cys Ala Thr Ala Leu Tyr Val Leu Arg Leu Ala Gln Asp<br>                 195                 200                205 | | 624 |
| cac ctc gtt tcc ggt gct gct gat gtc atg ctc gct ggt gca act tgc<br>His Leu Val Ser Gly Ala Ala Asp Val Met Leu Ala Gly Ala Thr Cys<br>      210               215                220 | | 672 |
| ttc ccg gag ccc ttt ttc att ctc tcc gga ttc tcc act ttc cag gcc<br>Phe Pro Glu Pro Phe Phe Ile Leu Ser Gly Phe Ser Thr Phe Gln Ala<br>225                   230                 235                240 | | 720 |
| atg cct gta tcg gga gac ggc atc tcg tac ccg ctt cac aag gac agt<br>Met Pro Val Ser Gly Asp Gly Ile Ser Tyr Pro Leu His Lys Asp Ser<br>                 245                 250                255 | | 768 |
| cag ggt ctc acc cct ggt gaa ggt ggt gcc att atg gtt ctc aag cgc<br>Gln Gly Leu Thr Pro Gly Glu Gly Gly Ala Ile Met Val Leu Lys Arg<br>            260                 265                270 | | 816 |
| ctt gac gac gct att cgc gat gga gac cac att tac ggt act ctg ctc<br>Leu Asp Asp Ala Ile Arg Asp Gly Asp His Ile Tyr Gly Thr Leu Leu<br>          275                 280                285 | | 864 |
| ggt gct acc atc agc aat gct ggc tgt ggt ctt ccc ctc aag cca cac<br>Gly Ala Thr Ile Ser Asn Ala Gly Cys Gly Leu Pro Leu Lys Pro His<br>      290               295                300 | | 912 |
| ttg ccc agc gag aag tcc tgc ctc att gat acc tac aag cgc gtc aac<br>Leu Pro Ser Glu Lys Ser Cys Leu Ile Asp Thr Tyr Lys Arg Val Asn<br>305                   310                 315                320 | | 960 |
| gtg cac ccg cac aag atc cag tac gtc gag tgc cac gca acg ggt act<br>Val His Pro His Lys Ile Gln Tyr Val Glu Cys His Ala Thr Gly Thr<br>                 325                 330                335 | | 1008 |
| ccc cag gga gac cgc gtt gag att gat gcc gtc aag gct tgc ttc gag<br>Pro Gln Gly Asp Arg Val Glu Ile Asp Ala Val Lys Ala Cys Phe Glu<br>            340                 345                350 | | 1056 |
| ggc aag gtg cct cgc ttt gga agc tcc aag ggt aac ttt ggc cac aca<br>Gly Lys Val Pro Arg Phe Gly Ser Ser Lys Gly Asn Phe Gly His Thr<br>          355                 360                365 | | 1104 |

|                                                                                               |      |
|-----------------------------------------------------------------------------------------------|------|
| ctc gtt gca gct ggt ttc gca ggc atg tgc aag gta ctc ctt gcc atg<br>Leu Val Ala Ala Gly Phe Ala Gly Met Cys Lys Val Leu Leu Ala Met<br>370              375                  380 | 1152 |
| aag cat ggt gtg atc ccg ccc act cct ggt gtc gat gga tct tcc caa<br>Lys His Gly Val Ile Pro Pro Thr Pro Gly Val Asp Gly Ser Ser Gln<br>385              390                  395                  400 | 1200 |
| atg gac ccg ctt gtg gtc tct gag ccc atc cca tgg ccc gac act gag<br>Met Asp Pro Leu Val Val Ser Glu Pro Ile Pro Trp Pro Asp Thr Glu<br>                      405                  410                  415 | 1248 |
| ggc gag ccc aag cgc gct ggt ctc tcc gct ttc ggc ttt ggt ggc acc<br>Gly Glu Pro Lys Arg Ala Gly Leu Ser Ala Phe Gly Phe Gly Gly Thr<br>                 420                  425                  430 | 1296 |
| aac gcc cac gca gtc ttt gag gag ttt gac cgc tcc aag gct gcc tgt<br>Asn Ala His Ala Val Phe Glu Glu Phe Asp Arg Ser Lys Ala Ala Cys<br>             435                  440                  445 | 1344 |
| gcc acc cac gat agc atc agt tcc ctc agc tca cgt tgt ggc ggg gag<br>Ala Thr His Asp Ser Ile Ser Ser Leu Ser Ser Arg Cys Gly Gly Glu<br>             450                  455                  460 | 1392 |
| ggc aac atg cgc att gct att acc ggt atg gat gcc acc ttc ggc tcc<br>Gly Asn Met Arg Ile Ala Ile Thr Gly Met Asp Ala Thr Phe Gly Ser<br>465                  470                  475                  480 | 1440 |
| ctc aag ggc ctg gac gcc ttt gag cgt gcc atc tac aat ggc caa cat<br>Leu Lys Gly Leu Asp Ala Phe Glu Arg Ala Ile Tyr Asn Gly Gln His<br>                      485                  490                  495 | 1488 |
| ggt gct gtg cca ttg cct gag aag cgc tgg cgt ttc ctt ggt aaa gac<br>Gly Ala Val Pro Leu Pro Glu Lys Arg Trp Arg Phe Leu Gly Lys Asp<br>                 500                  505                  510 | 1536 |
| aag gac ttt ttg gac ctg tgc ggc gtc aag gag gtg ccc cac gga tgc<br>Lys Asp Phe Leu Asp Leu Cys Gly Val Lys Glu Val Pro His Gly Cys<br>             515                  520                  525 | 1584 |
| tac att gag gac gtc gag gtg gac ttt agc cgc ctg cgc acg ccc atg<br>Tyr Ile Glu Asp Val Glu Val Asp Phe Ser Arg Leu Arg Thr Pro Met<br>             530                  535                  540 | 1632 |
| acg cca gac gac atg ttg cgc ccc atg cag cta ctt gct gtc aca acc<br>Thr Pro Asp Asp Met Leu Arg Pro Met Gln Leu Leu Ala Val Thr Thr<br>545                  550                  555                  560 | 1680 |
| atc gac cgt gcc att ctc aac tct ggc ctc aag aag gga ggt aag gtc<br>Ile Asp Arg Ala Ile Leu Asn Ser Gly Leu Lys Lys Gly Gly Lys Val<br>                      565                  570                  575 | 1728 |
| gct gtc ttc gtc ggc ctt ggc act gac ctt gag ctc tac cgt cac cgc<br>Ala Val Phe Val Gly Leu Gly Thr Asp Leu Glu Leu Tyr Arg His Arg<br>                 580                  585                  590 | 1776 |
| gcc cgc gtt gcc ctc aag gag cgt gct cgt ccc gaa gcc gct gca gcc<br>Ala Arg Val Ala Leu Lys Glu Arg Ala Arg Pro Glu Ala Ala Ala Ala<br>             595                  600                  605 | 1824 |
| ctc aat gat atg atg tcc tac atc aac gat tgc ggt acc gct acc tcg<br>Leu Asn Asp Met Met Ser Tyr Ile Asn Asp Cys Gly Thr Ala Thr Ser<br>             610                  615                  620 | 1872 |
| tac aca tcc tac atc ggc aac ctc gtg gcc acc cgc gtg tct tca caa<br>Tyr Thr Ser Tyr Ile Gly Asn Leu Val Ala Thr Arg Val Ser Ser Gln<br>625                  630                  635                  640 | 1920 |
| tgg ggt ttc gag ggt cct tct ttc acc atc aca gag ggc aac aac tcc<br>Trp Gly Phe Glu Gly Pro Ser Phe Thr Ile Thr Glu Gly Asn Asn Ser<br>                      645                  650                  655 | 1968 |
| gtc tac cgt tgc gca gag ttg ggc aag tac ttg ctc gag act ggc gag<br>Val Tyr Arg Cys Ala Glu Leu Gly Lys Tyr Leu Leu Glu Thr Gly Glu<br>                 660                  665                  670 | 2016 |
| gtc gag gcc gta gtg atc gcc ggt gtg gat ctt tgc gcc agc gct gag<br>Val Glu Ala Val Val Ile Ala Gly Val Asp Leu Cys Ala Ser Ala Glu<br>             675                  680                  685 | 2064 |

```
                                                        -continued aat ctc tac gtg aag tcg cgt cgt ttc aag gtc tcg gag cag gag agc     2112
Asn Leu Tyr Val Lys Ser Arg Arg Phe Lys Val Ser Glu Gln Glu Ser
        690             695                 700 ccg cgg gcc agc ttc gac tcc ggc gct gac ggc tac ttt gtt ggt gag     2160
Pro Arg Ala Ser Phe Asp Ser Gly Ala Asp Gly Tyr Phe Val Gly Glu
705             710                 715                 720 gga tgt ggt gcc ctc gtc ctc aag cgc gag agc gac tgc acc aag gac     2208
Gly Cys Gly Ala Leu Val Leu Lys Arg Glu Ser Asp Cys Thr Lys Asp
                725                 730                 735 gaa cgc att tac gcc tgc atg gac gct atc gtg ccc ggc aac atg ccg     2256
Glu Arg Ile Tyr Ala Cys Met Asp Ala Ile Val Pro Gly Asn Met Pro
            740                 745                 750 gca gcc tgc atg gag gag gct ctc gcc cag gct cgc gtc aac ccc aag     2304
Ala Ala Cys Met Glu Glu Ala Leu Ala Gln Ala Arg Val Asn Pro Lys
        755                 760                 765 gac gtt gag atg ctc gag ctc tcc gct gac tct gcc cgc cac ctc aag     2352
Asp Val Glu Met Leu Glu Leu Ser Ala Asp Ser Ala Arg His Leu Lys
770             775                 780 aac ccc tcc gtt ctg cct aag gaa ctc act gct gag gag gaa atc cgc     2400
Asn Pro Ser Val Leu Pro Lys Glu Leu Thr Ala Glu Glu Glu Ile Arg
785             790                 795                 800 ggc att gag gcc att ctc agc cag cgc tct agc aac gaa gct gtg gag     2448
Gly Ile Glu Ala Ile Leu Ser Gln Arg Ser Ser Asn Glu Ala Val Glu
                805                 810                 815 ccc cac aac gtc gct gtc agc agc gtc aag tcc act gtc ggt gac acc     2496
Pro His Asn Val Ala Val Ser Ser Val Lys Ser Thr Val Gly Asp Thr
            820                 825                 830 ggc tac gcc tca gga gct gcc agt ctc atc aag acg gct ctc tgt ctg     2544
Gly Tyr Ala Ser Gly Ala Ala Ser Leu Ile Lys Thr Ala Leu Cys Leu
        835                 840                 845 tac aac cgc tac ttg ccc tca aac ggc gcc tcc tgg gag gag cct gca     2592
Tyr Asn Arg Tyr Leu Pro Ser Asn Gly Ala Ser Trp Glu Glu Pro Ala
850             855                 860 cct gag aca cag tgg ggc aag tct ctg tac gcg tgc cag tcc tcg cgg     2640
Pro Glu Thr Gln Trp Gly Lys Ser Leu Tyr Ala Cys Gln Ser Ser Arg
865             870                 875                 880 gcc tgg ttg aag aac cct gga gct cgc cgc cac gca gct gtc tca ggt     2688
Ala Trp Leu Lys Asn Pro Gly Ala Arg Arg His Ala Ala Val Ser Gly
                885                 890                 895 gtt tcc gag acc cgt tca tgc tac acg gtg ctg ctc tct gat gtg gag     2736
Val Ser Glu Thr Arg Ser Cys Tyr Thr Val Leu Leu Ser Asp Val Glu
            900                 905                 910 ggc cac cac gag acc aag agc cgc att tcg ctc gat gac gat gcc gtc     2784
Gly His His Glu Thr Lys Ser Arg Ile Ser Leu Asp Asp Asp Ala Val
        915                 920                 925 aaa ctc ctc gta atc cgc gga gac tcc cac gac gct atc acg cag cgt     2832
Lys Leu Leu Val Ile Arg Gly Asp Ser His Asp Ala Ile Thr Gln Arg
930             935                 940 gtt gac aag ctc cgc gag cgc ctc gcc cag cct agc gct aat gta cgt     2880
Val Asp Lys Leu Arg Glu Arg Leu Ala Gln Pro Ser Ala Asn Val Arg
945             950                 955                 960 ctt gct ttt atg gag ttg ctc ggc gag agc att gcc cag gag acc aag     2928
Leu Ala Phe Met Glu Leu Leu Gly Glu Ser Ile Ala Gln Glu Thr Lys
                965                 970                 975 acc ccg ttg ccg gcc ttc gct ctg tgc ctg gtg acc tct cct agt aag     2976
Thr Pro Leu Pro Ala Phe Ala Leu Cys Leu Val Thr Ser Pro Ser Lys
            980                 985                 990 ctc cag aag gag ctt gaa ctc gcc  tcc aag ggc atc ccg  cgg agt ctt    3024
Leu Gln Lys Glu Leu Glu Leu Ala  Ser Lys Gly Ile Pro  Arg Ser Leu
        995                 1000                1005
```

-continued

| | | | | | | | | | | | |
|---|---|---|---|---|---|---|---|---|---|---|---|
| aag | atg | ggc | cgc | gac | tgg | aca | tca | ccc | tcg | ggc | agc | cac | ttt | gca | 3069 |
| Lys | Met | Gly | Arg | Asp | Trp | Thr | Ser | Pro | Ser | Gly | Ser | His | Phe | Ala | |
| | 1010 | | | | | 1015 | | | | | 1020 | | | | |
| ccc | aag | cca | ctg | tca | agc | gat | cgc | gtt | gcg | ttt | atg | tac | ggc | gaa | 3114 |
| Pro | Lys | Pro | Leu | Ser | Ser | Asp | Arg | Val | Ala | Phe | Met | Tyr | Gly | Glu | |
| | 1025 | | | | | 1030 | | | | | 1035 | | | | |
| ggc | cga | agc | cct | tac | tat | ggt | atc | ggc | ctt | gac | att | cac | cgc | atc | 3159 |
| Gly | Arg | Ser | Pro | Tyr | Tyr | Gly | Ile | Gly | Leu | Asp | Ile | His | Arg | Ile | |
| | 1040 | | | | | 1045 | | | | | 1050 | | | | |
| tgg | ccc | gaa | ctt | cac | gag | ttt | gta | aac | gcc | aag | acc | aac | aag | ctt | 3204 |
| Trp | Pro | Glu | Leu | His | Glu | Phe | Val | Asn | Ala | Lys | Thr | Asn | Lys | Leu | |
| | 1055 | | | | | 1060 | | | | | 1065 | | | | |
| tgg | gat | caa | ggc | gac | aga | tgg | ttg | atc | ccg | cgc | gcc | tcg | acg | aag | 3249 |
| Trp | Asp | Gln | Gly | Asp | Arg | Trp | Leu | Ile | Pro | Arg | Ala | Ser | Thr | Lys | |
| | 1070 | | | | | 1075 | | | | | 1080 | | | | |
| gag | gag | ctt | aag | gcg | cag | gaa | gat | gag | ttc | agc | cgc | aac | cag | gtg | 3294 |
| Glu | Glu | Leu | Lys | Ala | Gln | Glu | Asp | Glu | Phe | Ser | Arg | Asn | Gln | Val | |
| | 1085 | | | | | 1090 | | | | | 1095 | | | | |
| gag | atg | ttc | cga | ctc | ggt | att | ctc | atg | tcc | atg | tgc | ttc | acc | cac | 3339 |
| Glu | Met | Phe | Arg | Leu | Gly | Ile | Leu | Met | Ser | Met | Cys | Phe | Thr | His | |
| | 1100 | | | | | 1105 | | | | | 1110 | | | | |
| atc | gct | cgt | gac | gtg | ctt | ggc | atc | cag | ccc | aag | gct | gct | ttc | gga | 3384 |
| Ile | Ala | Arg | Asp | Val | Leu | Gly | Ile | Gln | Pro | Lys | Ala | Ala | Phe | Gly | |
| | 1115 | | | | | 1120 | | | | | 1125 | | | | |
| ctg | agc | ctt | gga | gag | att | tcc | atg | gtt | ttt | gcc | ttt | tct | gag | aag | 3429 |
| Leu | Ser | Leu | Gly | Glu | Ile | Ser | Met | Val | Phe | Ala | Phe | Ser | Glu | Lys | |
| | 1130 | | | | | 1135 | | | | | 1140 | | | | |
| aac | ggc | ctt | gtc | tct | gag | gag | ctg | aca | act | aaa | ctc | cgc | aac | tcg | 3474 |
| Asn | Gly | Leu | Val | Ser | Glu | Glu | Leu | Thr | Thr | Lys | Leu | Arg | Asn | Ser | |
| | 1145 | | | | | 1150 | | | | | 1155 | | | | |
| gag | gtc | tgg | cgt | aag | gcc | ctc | gct | gtt | gag | ttt | gac | gcc | ctc | cgc | 3519 |
| Glu | Val | Trp | Arg | Lys | Ala | Leu | Ala | Val | Glu | Phe | Asp | Ala | Leu | Arg | |
| | 1160 | | | | | 1165 | | | | | 1170 | | | | |
| aag | gcc | tgg | aat | att | ccc | caa | gat | acc | cct | gtc | agc | gag | ttc | tgg | 3564 |
| Lys | Ala | Trp | Asn | Ile | Pro | Gln | Asp | Thr | Pro | Val | Ser | Glu | Phe | Trp | |
| | 1175 | | | | | 1180 | | | | | 1185 | | | | |
| caa | gga | tac | gtg | gta | cgt | gga | acc | cgc | gag | gcc | gtt | gaa | gcg | gcc | 3609 |
| Gln | Gly | Tyr | Val | Val | Arg | Gly | Thr | Arg | Glu | Ala | Val | Glu | Ala | Ala | |
| | 1190 | | | | | 1195 | | | | | 1200 | | | | |
| atc | ggc | ccc | aac | aat | aag | tac | gtg | cac | ttg | acc | att | gtc | aac | gat | 3654 |
| Ile | Gly | Pro | Asn | Asn | Lys | Tyr | Val | His | Leu | Thr | Ile | Val | Asn | Asp | |
| | 1205 | | | | | 1210 | | | | | 1215 | | | | |
| gcc | aac | agt | gct | ctc | atc | agt | ggc | aag | cct | gaa | gat | tgc | aag | gct | 3699 |
| Ala | Asn | Ser | Ala | Leu | Ile | Ser | Gly | Lys | Pro | Glu | Asp | Cys | Lys | Ala | |
| | 1220 | | | | | 1225 | | | | | 1230 | | | | |
| gcc | att | gct | cgc | ctg | agc | agc | aac | ctc | cct | gct | ttg | ccc | gtg | gac | 3744 |
| Ala | Ile | Ala | Arg | Leu | Ser | Ser | Asn | Leu | Pro | Ala | Leu | Pro | Val | Asp | |
| | 1235 | | | | | 1240 | | | | | 1245 | | | | |
| ctt | ggt | atg | tgt | ggc | cac | tgc | ccc | gtg | gtc | gag | ccg | tac | ggc | aag | 3789 |
| Leu | Gly | Met | Cys | Gly | His | Cys | Pro | Val | Val | Glu | Pro | Tyr | Gly | Lys | |
| | 1250 | | | | | 1255 | | | | | 1260 | | | | |
| cag | atc | gct | gag | atc | cat | agc | gtc | ctc | gag | att | ccc | gag | gtt | gcc | 3834 |
| Gln | Ile | Ala | Glu | Ile | His | Ser | Val | Leu | Glu | Ile | Pro | Glu | Val | Ala | |
| | 1265 | | | | | 1270 | | | | | 1275 | | | | |
| ggc | ctt | gac | ctg | tac | acg | agc | gtc | aac | cag | aag | aag | ctt | gtt | aac | 3879 |
| Gly | Leu | Asp | Leu | Tyr | Thr | Ser | Val | Asn | Gln | Lys | Lys | Leu | Val | Asn | |
| | 1280 | | | | | 1285 | | | | | 1290 | | | | |
| aag | tcc | act | gga | gcc | agc | gac | gag | tac | gca | ccc | agc | ttt | ggt | gaa | 3924 |
| Lys | Ser | Thr | Gly | Ala | Ser | Asp | Glu | Tyr | Ala | Pro | Ser | Phe | Gly | Glu | |
| | 1295 | | | | | 1300 | | | | | 1305 | | | | |

-continued

| | | | | | | | | | | | | | | |
|---|---|---|---|---|---|---|---|---|---|---|---|---|---|---|
| tac | gca | gca | cag | ctg | tac | act | gtt | cag | gca | gac | ttt | cct | aag | atc | 3969 |
| Tyr | Ala | Ala | Gln | Leu | Tyr | Thr | Val | Gln | Ala | Asp | Phe | Pro | Lys | Ile |
| | 1310 | | | | 1315 | | | | 1320 | | | | | |
| gcc | aag | acc | gtt | agc | gac | aag | aac | ttt | gac | gtc | ttt | gtt | gag | act | 4014 |
| Ala | Lys | Thr | Val | Ser | Asp | Lys | Asn | Phe | Asp | Val | Phe | Val | Glu | Thr |
| 1325 | | | | | 1330 | | | | | 1335 | | | | |
| ggt | ccc | aac | gct | cac | cgt | agc | gcc | gca | att | cgc | gcc | acc | ctt | gga | 4059 |
| Gly | Pro | Asn | Ala | His | Arg | Ser | Ala | Ala | Ile | Arg | Ala | Thr | Leu | Gly |
| 1340 | | | | 1345 | | | | | 1350 | | | | | |
| aat | agc | aag | cct | ttt | gtc | acc | gga | tcc | atg | gac | cgc | cag | aac | gag | 4104 |
| Asn | Ser | Lys | Pro | Phe | Val | Thr | Gly | Ser | Met | Asp | Arg | Gln | Asn | Glu |
| 1355 | | | | | 1360 | | | | | 1365 | | | | |
| aat | gct | tgg | aca | acc | atg | gtc | aag | ctg | gtt | gcc | tct | ctc | caa | gcc | 4149 |
| Asn | Ala | Trp | Thr | Thr | Met | Val | Lys | Leu | Val | Ala | Ser | Leu | Gln | Ala |
| | 1370 | | | | 1375 | | | | 1380 | | | | | |
| cac | cgc | gtg | cct | ggc | gtg | aag | gtc | tcc | cct | ctg | tac | cac | ccc | gag | 4194 |
| His | Arg | Val | Pro | Gly | Val | Lys | Val | Ser | Pro | Leu | Tyr | His | Pro | Glu |
| 1385 | | | | | 1390 | | | | | 1395 | | | | |
| act | gtt | gag | gag | gct | acg | cag | agt | tac | aac | gat | atg | gtg | gct | ggc | 4239 |
| Thr | Val | Glu | Glu | Ala | Thr | Gln | Ser | Tyr | Asn | Asp | Met | Val | Ala | Gly |
| | 1400 | | | | 1405 | | | | | 1410 | | | | |
| aag | aag | cct | act | aag | aac | aag | ttc | ttg | cgt | aag | att | gtg | gtc | aat | 4284 |
| Lys | Lys | Pro | Thr | Lys | Asn | Lys | Phe | Leu | Arg | Lys | Ile | Val | Val | Asn |
| 1415 | | | | | 1420 | | | | | 1425 | | | | |
| ggt | cgc | tat | gac | ccc | aaa | aag | cag | ctc | gtg | ccg | ccc | cag | gtg | cta | 4329 |
| Gly | Arg | Tyr | Asp | Pro | Lys | Lys | Gln | Leu | Val | Pro | Pro | Gln | Val | Leu |
| | 1430 | | | | 1435 | | | | | 1440 | | | | |
| gct | aag | ctt | cct | cct | gcg | gac | ccc | aag | atc | gag | gct | ctt | atc | cag | 4374 |
| Ala | Lys | Leu | Pro | Pro | Ala | Asp | Pro | Lys | Ile | Glu | Ala | Leu | Ile | Gln |
| 1445 | | | | | 1450 | | | | | 1455 | | | | |
| gct | cgc | aag | atg | cag | cct | att | gcc | ccc | aag | ttc | atg | gag | cgt | ctc | 4419 |
| Ala | Arg | Lys | Met | Gln | Pro | Ile | Ala | Pro | Lys | Phe | Met | Glu | Arg | Leu |
| | 1460 | | | | 1465 | | | | | 1470 | | | | |
| gac | att | cag | gag | caa | gac | gcc | aca | cgc | gac | cct | att | ctc | aac | aag | 4464 |
| Asp | Ile | Gln | Glu | Gln | Asp | Ala | Thr | Arg | Asp | Pro | Ile | Leu | Asn | Lys |
| 1475 | | | | | 1480 | | | | | 1485 | | | | |
| gat | aac | aaa | cct | tcc | gct | gct | cct | gcc | ctt | gtc | cct | gct | gct | ccg | 4509 |
| Asp | Asn | Lys | Pro | Ser | Ala | Ala | Pro | Ala | Leu | Val | Pro | Ala | Ala | Pro |
| | 1490 | | | | 1495 | | | | | 1500 | | | | |
| gcc | cct | gct | ccg | gcc | cgc | agc | gcc | tcc | gga | gct | gtt | gtg | gct | tcc | 4554 |
| Ala | Pro | Ala | Pro | Ala | Arg | Ser | Ala | Ser | Gly | Ala | Val | Val | Ala | Ser |
| 1505 | | | | | 1510 | | | | | 1515 | | | | |
| tct | gag | gct | ctc | cgt | gcc | aaa | ctt | ttg | gag | ctc | aac | agc | act | ttg | 4599 |
| Ser | Glu | Ala | Leu | Arg | Ala | Lys | Leu | Leu | Glu | Leu | Asn | Ser | Thr | Leu |
| | 1520 | | | | 1525 | | | | | 1530 | | | | |
| atg | ctt | ggt | gtc | aac | gcc | aac | ggt | gat | ctc | gtt | gaa | gca | agc | cca | 4644 |
| Met | Leu | Gly | Val | Asn | Ala | Asn | Gly | Asp | Leu | Val | Glu | Ala | Ser | Pro |
| 1535 | | | | | 1540 | | | | | 1545 | | | | |
| agt | gaa | gca | tct | att | gtt | gtg | ccc | aag | tgc | gat | atc | aag | gat | ctt | 4689 |
| Ser | Glu | Ala | Ser | Ile | Val | Val | Pro | Lys | Cys | Asp | Ile | Lys | Asp | Leu |
| | 1550 | | | | 1555 | | | | | 1560 | | | | |
| ggc | agc | cgt | gcc | ttc | atg | gag | aca | tat | ggt | gta | tcc | gcc | ccc | atg | 4734 |
| Gly | Ser | Arg | Ala | Phe | Met | Glu | Thr | Tyr | Gly | Val | Ser | Ala | Pro | Met |
| 1565 | | | | | 1570 | | | | | 1575 | | | | |
| tac | acc | ggc | gcc | atg | gca | aag | ggc | att | gca | tcc | gct | gag | atg | gtt | 4779 |
| Tyr | Thr | Gly | Ala | Met | Ala | Lys | Gly | Ile | Ala | Ser | Ala | Glu | Met | Val |
| | 1580 | | | | 1585 | | | | | 1590 | | | | |
| atc | gct | gcc | gga | aag | cgc | ggc | atc | ctt | ggt | tct | ctc | ggt | gct | ggt | 4824 |
| Ile | Ala | Ala | Gly | Lys | Arg | Gly | Ile | Leu | Gly | Ser | Leu | Gly | Ala | Gly |
| 1595 | | | | | 1600 | | | | | 1605 | | | | |

```
                                        -continued ggt ctt  cct atc gcc acc gta cgc aag gct ctc gaa gct atc cag         4869
Gly Leu  Pro Ile Ala Thr Val Arg Lys Ala Leu Glu Ala Ile Gln
    1610             1615                 1620 gct gaa  ctg ccc aag ggc cct tac gct gtc aac ctc atc cac tct         4914
Ala Glu  Leu Pro Lys Gly Pro Tyr Ala Val Asn Leu Ile His Ser
    1625             1630                 1635 ccc ttc  gac agc aac ctc gag aag ggt aac gtc gac ctc ttc ctc         4959
Pro Phe  Asp Ser Asn Leu Glu Lys Gly Asn Val Asp Leu Phe Leu
    1640             1645                 1650 gag aag  ggc gtc act gtc gtt gaa gcc tcc gcc ttt atg acc ttg         5004
Glu Lys  Gly Val Thr Val Val Glu Ala Ser Ala Phe Met Thr Leu
    1655             1660                 1665 acc ccg  cag ctc gtg cgc tac cgt gct gca ggt ctc tct cgc gct         5049
Thr Pro  Gln Leu Val Arg Tyr Arg Ala Ala Gly Leu Ser Arg Ala
    1670             1675                 1680 gct gat  ggc tcc acg gtt att aag aac cgc gtc atc ggt aag gtt         5094
Ala Asp  Gly Ser Thr Val Ile Lys Asn Arg Val Ile Gly Lys Val
    1685             1690                 1695 tct cgc  aca gag ctt gcc gca atg ttt atc cgt ccc gcg ccc gag         5139
Ser Arg  Thr Glu Leu Ala Ala Met Phe Ile Arg Pro Ala Pro Glu
    1700             1705                 1710 aat ctc  ctc gag aag ctg ctg aag tcc ggc gag atc acc caa gag         5184
Asn Leu  Leu Glu Lys Leu Leu Lys Ser Gly Glu Ile Thr Gln Glu
    1715             1720                 1725 cag gct  gct ctc gca cgc aca gtg cct gtg gca gac gac att gcc         5229
Gln Ala  Ala Leu Ala Arg Thr Val Pro Val Ala Asp Asp Ile Ala
    1730             1735                 1740 gtt gag  gcg gac tcc ggt ggc cac acc gat aac cgc ccc atc cac         5274
Val Glu  Ala Asp Ser Gly Gly His Thr Asp Asn Arg Pro Ile His
    1745             1750                 1755 gtc atc  ctc cct ctc att gtc aac ctc cgt gat cgt ctg cac aag         5319
Val Ile  Leu Pro Leu Ile Val Asn Leu Arg Asp Arg Leu His Lys
    1760             1765                 1770 gag tgc  ggc tac cct gcc cac ctt cgc gtt cgc gtt ggt gct ggt         5364
Glu Cys  Gly Tyr Pro Ala His Leu Arg Val Arg Val Gly Ala Gly
    1775             1780                 1785 ggt ggc  att gga tgc cct cag gcc gcc att gcc acc ttc aac atg         5409
Gly Gly  Ile Gly Cys Pro Gln Ala Ala Ile Ala Thr Phe Asn Met
    1790             1795                 1800 ggc gcg  gcc ttc atc gtc act ggt acc gta aac cag atg agt aag         5454
Gly Ala  Ala Phe Ile Val Thr Gly Thr Val Asn Gln Met Ser Lys
    1805             1810                 1815 caa gct  gga acc tgt gac acc gtt cgc aag cag ctc tca caa gcc         5499
Gln Ala  Gly Thr Cys Asp Thr Val Arg Lys Gln Leu Ser Gln Ala
    1820             1825                 1830 acc tac  tcc gac atc tgc atg gcc cca gca gct gac atg ttt gag         5544
Thr Tyr  Ser Asp Ile Cys Met Ala Pro Ala Ala Asp Met Phe Glu
    1835             1840                 1845 gaa ggt  gtc aag ctc cag gtg ctc aag aag gga act atg ttc ccc         5589
Glu Gly  Val Lys Leu Gln Val Leu Lys Lys Gly Thr Met Phe Pro
    1850             1855                 1860 tcg cgt  gcc aac aag ctc tat gag ctc ttc gtc aag tat gac tcc         5634
Ser Arg  Ala Asn Lys Leu Tyr Glu Leu Phe Val Lys Tyr Asp Ser
    1865             1870                 1875 ttt gag  tcc atg gct cct gga gag ctg gaa cgt gtg gag aag cgc         5679
Phe Glu  Ser Met Ala Pro Gly Glu Leu Glu Arg Val Glu Lys Arg
    1880             1885                 1890 att ttc  aag aag tct ctg tca gag gtt tgg gaa gag acc aag gac         5724
Ile Phe  Lys Lys Ser Leu Ser Glu Val Trp Glu Glu Thr Lys Asp
    1895             1900                 1905
```

-continued

```
ttc tac atc aac agg ttg cag aac ccg gag aag att gag cgc gcg      5769
Phe Tyr Ile Asn Arg Leu Gln Asn Pro Glu Lys Ile Glu Arg Ala
1910                1915                1920 gag cgt gac ccc aag ctt aag atg tcc ttg tgc ttc cgc tgg tac      5814
Glu Arg Asp Pro Lys Leu Lys Met Ser Leu Cys Phe Arg Trp Tyr
    1925                1930                1935 ctt ggt ttg gcg agc ttc tgg gca aac gct ggc atc ccg gac cgt      5859
Leu Gly Leu Ala Ser Phe Trp Ala Asn Ala Gly Ile Pro Asp Arg
1940                1945                1950 gcc atg gac tac cag gtt tgg tgt ggc cca gcg att gga tct ttc      5904
Ala Met Asp Tyr Gln Val Trp Cys Gly Pro Ala Ile Gly Ser Phe
    1955                1960                1965 aac gac ttc atc aag ggt acc tac ctt gac ccc gcc gtt gcc aac      5949
Asn Asp Phe Ile Lys Gly Thr Tyr Leu Asp Pro Ala Val Ala Asn
1970                1975                1980 gag tac ccc gat gtt gtg caa atc aac ttg cag atc ctc cgt ggt      5994
Glu Tyr Pro Asp Val Val Gln Ile Asn Leu Gln Ile Leu Arg Gly
    1985                1990                1995 gcc tgc ttc ttg cgc cgc ctc gaa gct gtc cgt aat gcc ccg ctg      6039
Ala Cys Phe Leu Arg Arg Leu Glu Ala Val Arg Asn Ala Pro Leu
2000                2005                2010 aag gct aac gcc aag cag gtt gct gcc gag att gat gac atc tac      6084
Lys Ala Asn Ala Lys Gln Val Ala Ala Glu Ile Asp Asp Ile Tyr
    2015                2020                2025 gtg ccc act gag cgc ctg taa                                      6105
Val Pro Thr Glu Arg Leu
    2030

<210> SEQ ID NO 2
<211> LENGTH: 2034
<212> TYPE: PRT
<213> ORGANISM: Aurantiochytrium sp. OH4

<400> SEQUENCE: 2

Met Ala Ser Arg Lys Asn Val Ser Ala Ala His Glu Met His Asp Glu
1               5                   10                  15

Lys Arg Ile Ala Val Val Gly Met Ala Val Gln Tyr Ala Gly Cys Lys
            20                  25                  30

Asp Lys Glu Glu Phe Trp Lys Val Val Met Gly Gly Glu Ala Ala Trp
        35                  40                  45

Thr Lys Ile Ser Asp Lys Arg Leu Gly Ser Asn Lys Arg Ala Glu His
    50                  55                  60

Phe Lys Ala Glu Arg Ser Lys Phe Ala Asp Thr Phe Cys Asn Glu Asn
65                  70                  75                  80

Tyr Gly Cys Val Asp Asp Ser Val Asp Asn Glu His Glu Leu Leu Leu
                85                  90                  95

Lys Leu Ser Lys Lys Ala Leu Ser Glu Thr Ser Val Ser Asp Ser Thr
            100                 105                 110

Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
    130                 135                 140

Gly Ala Arg Val Phe Lys Asp Ala Ser Lys Trp Ser Glu Arg Glu Gln
145                 150                 155                 160

Ser Gln Asn Pro Glu Ala Gly Asp Arg Arg Ile Phe Met Asp Pro Ala
                165                 170                 175

Ser Phe Val Ala Glu Glu Leu Asn Leu Gly Pro Leu His Tyr Ser Val
            180                 185                 190
```

```
Asp Ala Ala Cys Ala Thr Ala Leu Tyr Val Leu Arg Leu Ala Gln Asp
            195                 200                 205

His Leu Val Ser Gly Ala Ala Asp Val Met Leu Ala Gly Ala Thr Cys
210                 215                 220

Phe Pro Glu Pro Phe Ile Leu Ser Gly Phe Ser Thr Phe Gln Ala
225                 230                 235                 240

Met Pro Val Ser Gly Asp Gly Ile Ser Tyr Pro Leu His Lys Asp Ser
                245                 250                 255

Gln Gly Leu Thr Pro Gly Glu Gly Ala Ile Met Val Leu Lys Arg
                260                 265                 270

Leu Asp Asp Ala Ile Arg Asp Gly Asp His Ile Tyr Gly Thr Leu Leu
                275                 280                 285

Gly Ala Thr Ile Ser Asn Ala Gly Cys Gly Leu Pro Leu Lys Pro His
            290                 295                 300

Leu Pro Ser Glu Lys Ser Cys Leu Ile Asp Thr Tyr Lys Arg Val Asn
305                 310                 315                 320

Val His Pro His Lys Ile Gln Tyr Val Glu Cys His Ala Thr Gly Thr
                325                 330                 335

Pro Gln Gly Asp Arg Val Glu Ile Asp Ala Val Lys Ala Cys Phe Glu
                340                 345                 350

Gly Lys Val Pro Arg Phe Gly Ser Lys Gly Asn Phe Gly His Thr
            355                 360                 365

Leu Val Ala Ala Gly Phe Ala Gly Met Cys Lys Val Leu Leu Ala Met
            370                 375                 380

Lys His Gly Val Ile Pro Pro Thr Pro Gly Val Asp Gly Ser Ser Gln
385                 390                 395                 400

Met Asp Pro Leu Val Val Ser Glu Pro Ile Pro Trp Pro Asp Thr Glu
                405                 410                 415

Gly Glu Pro Lys Arg Ala Gly Leu Ser Ala Phe Gly Phe Gly Gly Thr
                420                 425                 430

Asn Ala His Ala Val Phe Glu Glu Phe Asp Arg Ser Lys Ala Ala Cys
            435                 440                 445

Ala Thr His Asp Ser Ile Ser Ser Leu Ser Ser Arg Cys Gly Gly Glu
            450                 455                 460

Gly Asn Met Arg Ile Ala Ile Thr Gly Met Asp Ala Thr Phe Gly Ser
465                 470                 475                 480

Leu Lys Gly Leu Asp Ala Phe Glu Arg Ala Ile Tyr Asn Gly Gln His
                485                 490                 495

Gly Ala Val Pro Leu Pro Glu Lys Arg Trp Arg Phe Leu Gly Lys Asp
            500                 505                 510

Lys Asp Phe Leu Asp Leu Cys Gly Val Lys Glu Val Pro His Gly Cys
            515                 520                 525

Tyr Ile Glu Asp Val Glu Val Asp Phe Ser Arg Leu Arg Thr Pro Met
            530                 535                 540

Thr Pro Asp Asp Met Leu Arg Pro Met Gln Leu Leu Ala Val Thr Thr
545                 550                 555                 560

Ile Asp Arg Ala Ile Leu Asn Ser Gly Leu Lys Lys Gly Gly Lys Val
                565                 570                 575

Ala Val Phe Val Gly Leu Gly Thr Asp Leu Glu Leu Tyr Arg His Arg
            580                 585                 590

Ala Arg Val Ala Leu Lys Glu Arg Ala Arg Pro Glu Ala Ala Ala Ala
            595                 600                 605
```

-continued

| | | | | | | | | | | | |
|---|---|---|---|---|---|---|---|---|---|---|---|
|Leu|Asn|Asp|Met|Met|Ser|Tyr|Ile|Asn|Asp|Cys|Gly|Thr|Ala|Thr|Ser|
|610| | | | |615| | | | |620| | | | | |

Tyr Thr Ser Tyr Ile Gly Asn Leu Val Ala Thr Arg Val Ser Ser Gln
625                630                635                640

Trp Gly Phe Glu Gly Pro Ser Phe Thr Ile Thr Glu Gly Asn Asn Ser
               645                650                655

Val Tyr Arg Cys Ala Glu Leu Gly Lys Tyr Leu Leu Glu Thr Gly Glu
          660                665                670

Val Glu Ala Val Val Ile Ala Gly Val Asp Leu Cys Ala Ser Ala Glu
     675                680                685

Asn Leu Tyr Val Lys Ser Arg Arg Phe Lys Val Ser Glu Gln Glu Ser
690                695                700

Pro Arg Ala Ser Phe Asp Ser Gly Ala Asp Gly Tyr Phe Val Gly Glu
705                710                715                720

Gly Cys Gly Ala Leu Val Leu Lys Arg Glu Ser Asp Cys Thr Lys Asp
               725                730                735

Glu Arg Ile Tyr Ala Cys Met Asp Ala Ile Val Pro Gly Asn Met Pro
          740                745                750

Ala Ala Cys Met Glu Glu Ala Leu Ala Gln Ala Arg Val Asn Pro Lys
     755                760                765

Asp Val Glu Met Leu Glu Leu Ser Ala Asp Ser Ala Arg His Leu Lys
770                775                780

Asn Pro Ser Val Leu Pro Lys Glu Leu Thr Ala Glu Glu Ile Arg
785                790                795                800

Gly Ile Glu Ala Ile Leu Ser Gln Arg Ser Ser Asn Glu Ala Val Glu
               805                810                815

Pro His Asn Val Ala Val Ser Ser Val Lys Ser Thr Val Gly Asp Thr
          820                825                830

Gly Tyr Ala Ser Gly Ala Ala Ser Leu Ile Lys Thr Ala Leu Cys Leu
     835                840                845

Tyr Asn Arg Tyr Leu Pro Ser Asn Gly Ala Ser Trp Glu Glu Pro Ala
850                855                860

Pro Glu Thr Gln Trp Gly Lys Ser Leu Tyr Ala Cys Gln Ser Ser Arg
865                870                875                880

Ala Trp Leu Lys Asn Pro Gly Ala Arg Arg His Ala Ala Val Ser Gly
               885                890                895

Val Ser Glu Thr Arg Ser Cys Tyr Thr Val Leu Leu Ser Asp Val Glu
          900                905                910

Gly His His Glu Thr Lys Ser Arg Ile Ser Leu Asp Asp Ala Val
     915                920                925

Lys Leu Leu Val Ile Arg Gly Asp Ser His Asp Ala Ile Thr Gln Arg
930                935                940

Val Asp Lys Leu Arg Glu Arg Leu Ala Gln Pro Ser Ala Asn Val Arg
945                950                955                960

Leu Ala Phe Met Glu Leu Leu Gly Glu Ser Ile Ala Gln Glu Thr Lys
               965                970                975

Thr Pro Leu Pro Ala Phe Ala Leu Cys Leu Val Thr Ser Pro Ser Lys
          980                985                990

Leu Gln Lys Glu Leu Glu Leu Ala Ser Lys Gly Ile Pro Arg Ser Leu
     995                1000               1005

Lys Met Gly Arg Asp Trp Thr Ser Pro Ser Gly Ser His Phe Ala
     1010               1015               1020

Pro Lys Pro Leu Ser Ser Asp Arg Val Ala Phe Met Tyr Gly Glu

|   |   |   | 1025 |   |   |   | 1030 |   |   |   | 1035 |   |   |
|---|---|---|---|---|---|---|---|---|---|---|---|---|---|

Gly Arg Ser Pro Tyr Tyr Gly Ile Gly Leu Asp Ile His Arg Ile
   1040                     1045                    1050

Trp Pro Glu Leu His Glu Phe Val Asn Ala Lys Thr Asn Lys Leu
   1055                     1060                    1065

Trp Asp Gln Gly Asp Arg Trp Leu Ile Pro Arg Ala Ser Thr Lys
   1070                     1075                    1080

Glu Glu Leu Lys Ala Gln Glu Asp Glu Phe Ser Arg Asn Gln Val
   1085                     1090                    1095

Glu Met Phe Arg Leu Gly Ile Leu Met Ser Met Cys Phe Thr His
   1100                     1105                    1110

Ile Ala Arg Asp Val Leu Gly Ile Gln Pro Lys Ala Ala Phe Gly
   1115                     1120                    1125

Leu Ser Leu Gly Glu Ile Ser Met Val Phe Ala Phe Ser Glu Lys
   1130                     1135                    1140

Asn Gly Leu Val Ser Glu Glu Leu Thr Thr Lys Leu Arg Asn Ser
   1145                     1150                    1155

Glu Val Trp Arg Lys Ala Leu Ala Val Glu Phe Asp Ala Leu Arg
   1160                     1165                    1170

Lys Ala Trp Asn Ile Pro Gln Asp Thr Pro Val Ser Glu Phe Trp
   1175                     1180                    1185

Gln Gly Tyr Val Val Arg Gly Thr Arg Glu Ala Val Glu Ala Ala
   1190                     1195                    1200

Ile Gly Pro Asn Asn Lys Tyr Val His Leu Thr Ile Val Asn Asp
   1205                     1210                    1215

Ala Asn Ser Ala Leu Ile Ser Gly Lys Pro Glu Asp Cys Lys Ala
   1220                     1225                    1230

Ala Ile Ala Arg Leu Ser Ser Asn Leu Pro Ala Leu Pro Val Asp
   1235                     1240                    1245

Leu Gly Met Cys Gly His Cys Pro Val Val Glu Pro Tyr Gly Lys
   1250                     1255                    1260

Gln Ile Ala Glu Ile His Ser Val Leu Glu Ile Pro Glu Val Ala
   1265                     1270                    1275

Gly Leu Asp Leu Tyr Thr Ser Val Asn Gln Lys Lys Leu Val Asn
   1280                     1285                    1290

Lys Ser Thr Gly Ala Ser Asp Glu Tyr Ala Pro Ser Phe Gly Glu
   1295                     1300                    1305

Tyr Ala Ala Gln Leu Tyr Thr Val Gln Ala Asp Phe Pro Lys Ile
   1310                     1315                    1320

Ala Lys Thr Val Ser Asp Lys Asn Phe Asp Val Phe Val Glu Thr
   1325                     1330                    1335

Gly Pro Asn Ala His Arg Ser Ala Ala Ile Arg Ala Thr Leu Gly
   1340                     1345                    1350

Asn Ser Lys Pro Phe Val Thr Gly Ser Met Asp Arg Gln Asn Glu
   1355                     1360                    1365

Asn Ala Trp Thr Thr Met Val Lys Leu Val Ala Ser Leu Gln Ala
   1370                     1375                    1380

His Arg Val Pro Gly Val Lys Val Ser Pro Leu Tyr His Pro Glu
   1385                     1390                    1395

Thr Val Glu Glu Ala Thr Gln Ser Tyr Asn Asp Met Val Ala Gly
   1400                     1405                    1410

Lys Lys Pro Thr Lys Asn Lys Phe Leu Arg Lys Ile Val Val Asn
   1415                     1420                    1425

-continued

```
Gly Arg Tyr Asp Pro Lys Lys Gln Leu Val Pro Pro Gln Val Leu
1430                1435                1440

Ala Lys Leu Pro Pro Ala Asp Pro Lys Ile Glu Ala Leu Ile Gln
1445                1450                1455

Ala Arg Lys Met Gln Pro Ile Ala Pro Lys Phe Met Glu Arg Leu
1460                1465                1470

Asp Ile Gln Glu Gln Asp Ala Thr Arg Asp Pro Ile Leu Asn Lys
1475                1480                1485

Asp Asn Lys Pro Ser Ala Ala Pro Ala Leu Val Pro Ala Ala Pro
1490                1495                1500

Ala Pro Ala Pro Ala Arg Ser Ala Ser Gly Ala Val Val Ala Ser
1505                1510                1515

Ser Glu Ala Leu Arg Ala Lys Leu Leu Glu Leu Asn Ser Thr Leu
1520                1525                1530

Met Leu Gly Val Asn Ala Asn Gly Asp Leu Val Glu Ala Ser Pro
1535                1540                1545

Ser Glu Ala Ser Ile Val Val Pro Lys Cys Asp Ile Lys Asp Leu
1550                1555                1560

Gly Ser Arg Ala Phe Met Glu Thr Tyr Gly Val Ser Ala Pro Met
1565                1570                1575

Tyr Thr Gly Ala Met Ala Lys Gly Ile Ala Ser Ala Glu Met Val
1580                1585                1590

Ile Ala Ala Gly Lys Arg Gly Ile Leu Gly Ser Leu Gly Ala Gly
1595                1600                1605

Gly Leu Pro Ile Ala Thr Val Arg Lys Ala Leu Glu Ala Ile Gln
1610                1615                1620

Ala Glu Leu Pro Lys Gly Pro Tyr Ala Val Asn Leu Ile His Ser
1625                1630                1635

Pro Phe Asp Ser Asn Leu Glu Lys Gly Asn Val Asp Leu Phe Leu
1640                1645                1650

Glu Lys Gly Val Thr Val Val Glu Ala Ser Ala Phe Met Thr Leu
1655                1660                1665

Thr Pro Gln Leu Val Arg Tyr Arg Ala Ala Gly Leu Ser Arg Ala
1670                1675                1680

Ala Asp Gly Ser Thr Val Ile Lys Asn Arg Val Ile Gly Lys Val
1685                1690                1695

Ser Arg Thr Glu Leu Ala Ala Met Phe Ile Arg Pro Ala Pro Glu
1700                1705                1710

Asn Leu Leu Glu Lys Leu Leu Lys Ser Gly Glu Ile Thr Gln Glu
1715                1720                1725

Gln Ala Ala Leu Ala Arg Thr Val Pro Val Ala Asp Asp Ile Ala
1730                1735                1740

Val Glu Ala Asp Ser Gly Gly His Thr Asp Asn Arg Pro Ile His
1745                1750                1755

Val Ile Leu Pro Leu Ile Val Asn Leu Arg Asp Arg Leu His Lys
1760                1765                1770

Glu Cys Gly Tyr Pro Ala His Leu Arg Val Arg Val Gly Ala Gly
1775                1780                1785

Gly Gly Ile Gly Cys Pro Gln Ala Ala Ile Ala Thr Phe Asn Met
1790                1795                1800

Gly Ala Ala Phe Ile Val Thr Gly Thr Val Asn Gln Met Ser Lys
1805                1810                1815
```

-continued

```
Gln Ala Gly Thr Cys Asp Thr Val Arg Lys Gln Leu Ser Gln Ala
    1820                1825                1830

Thr Tyr Ser Asp Ile Cys Met Ala Pro Ala Ala Asp Met Phe Glu
    1835                1840                1845

Glu Gly Val Lys Leu Gln Val Leu Lys Lys Gly Thr Met Phe Pro
    1850                1855                1860

Ser Arg Ala Asn Lys Leu Tyr Glu Leu Phe Val Lys Tyr Asp Ser
    1865                1870                1875

Phe Glu Ser Met Ala Pro Gly Glu Leu Glu Arg Val Glu Lys Arg
    1880                1885                1890

Ile Phe Lys Lys Ser Leu Ser Glu Val Trp Glu Thr Lys Asp
    1895                1900                1905

Phe Tyr Ile Asn Arg Leu Gln Asn Pro Glu Lys Ile Glu Arg Ala
    1910                1915                1920

Glu Arg Asp Pro Lys Leu Lys Met Ser Leu Cys Phe Arg Trp Tyr
    1925                1930                1935

Leu Gly Leu Ala Ser Phe Trp Ala Asn Ala Gly Ile Pro Asp Arg
    1940                1945                1950

Ala Met Asp Tyr Gln Val Trp Cys Gly Pro Ala Ile Gly Ser Phe
    1955                1960                1965

Asn Asp Phe Ile Lys Gly Thr Tyr Leu Asp Pro Ala Val Ala Asn
    1970                1975                1980

Glu Tyr Pro Asp Val Val Gln Ile Asn Leu Gln Ile Leu Arg Gly
    1985                1990                1995

Ala Cys Phe Leu Arg Arg Leu Glu Ala Val Arg Asn Ala Pro Leu
    2000                2005                2010

Lys Ala Asn Ala Lys Gln Val Ala Ala Glu Ile Asp Asp Ile Tyr
    2015                2020                2025

Val Pro Thr Glu Arg Leu
    2030

<210> SEQ ID NO 3
<211> LENGTH: 4302
<212> TYPE: DNA
<213> ORGANISM: Aurantiochytrium sp. OH4
<220> FEATURE:
<221> NAME/KEY: CDS
<222> LOCATION: (1)..(4302)

<400> SEQUENCE: 3 atg gcc act cgc gtg aag acc aac aag aaa cca tgc tgg gag atg acc      48
Met Ala Thr Arg Val Lys Thr Asn Lys Lys Pro Cys Trp Glu Met Thr
1               5                   10                  15 aag gag gag ctc acc agc ggc aag aac gtc gtt ttc gac tat gac gag      96
Lys Glu Glu Leu Thr Ser Gly Lys Asn Val Val Phe Asp Tyr Asp Glu
                20                  25                  30 ctc ctt gag ttc gcc gag ggt gac atc agc aag gtc ttc ggc ccc gaa     144
Leu Leu Glu Phe Ala Glu Gly Asp Ile Ser Lys Val Phe Gly Pro Glu
            35                  40                  45 ttc agc cag atc gac cag tac aag cgt cgc gtt cgt ctc ccc gcc cgc     192
Phe Ser Gln Ile Asp Gln Tyr Lys Arg Arg Val Arg Leu Pro Ala Arg
        50                  55                  60 gag tac ctc ctc gtc acc cgc gtc acc ctc atg gac gcc gag gtc aac     240
Glu Tyr Leu Leu Val Thr Arg Val Thr Leu Met Asp Ala Glu Val Asn
    65                  70                  75                  80 aac tac cgc gtc ggt gcc cgc atg gtc act gag tac gac ctc ccc gtc     288
Asn Tyr Arg Val Gly Ala Arg Met Val Thr Glu Tyr Asp Leu Pro Val
                85                  90                  95
```

```
aac ggt gag ctc tct gag ggt ggt gac tgc ccc tgg gcc gtg ctc gtc        336
Asn Gly Glu Leu Ser Glu Gly Gly Asp Cys Pro Trp Ala Val Leu Val
            100                 105                 110 gag agt ggc cag tgt gat ctc atg ctc atc tcc tac atg ggt att gac        384
Glu Ser Gly Gln Cys Asp Leu Met Leu Ile Ser Tyr Met Gly Ile Asp
            115                 120                 125 ttc cag aac aag agc gac cgc gtc tac cgt ctg ctc aac acc acc ctc        432
Phe Gln Asn Lys Ser Asp Arg Val Tyr Arg Leu Leu Asn Thr Thr Leu
        130                 135                 140 acc ttc tac ggt gtt gcc cag gag ggc gag acc ctg gag tac gat atc        480
Thr Phe Tyr Gly Val Ala Gln Glu Gly Glu Thr Leu Glu Tyr Asp Ile
145                 150                 155                 160 cgc gtg acc ggc ttc gcc aag cgt ctc gac ggt gac atc tcc atg ttc        528
Arg Val Thr Gly Phe Ala Lys Arg Leu Asp Gly Asp Ile Ser Met Phe
                165                 170                 175 ttc ttc gag tac gac tgc tac gtc aac ggc cgt ctc ctc atc gag atg        576
Phe Phe Glu Tyr Asp Cys Tyr Val Asn Gly Arg Leu Leu Ile Glu Met
            180                 185                 190 cgc gac ggc tgt gcc ggt ttc ttc acc aac gag gag ctc gcc gcc ggc        624
Arg Asp Gly Cys Ala Gly Phe Phe Thr Asn Glu Glu Leu Ala Ala Gly
        195                 200                 205 aag ggt gtc gtc ttt acc cgc gct gat ctc ctc gcc cgc gag aag acc        672
Lys Gly Val Val Phe Thr Arg Ala Asp Leu Leu Ala Arg Glu Lys Thr
    210                 215                 220 aag aag cag gac atc acc ccg tac gcc att gcc ccg cgt ctt aac aag        720
Lys Lys Gln Asp Ile Thr Pro Tyr Ala Ile Ala Pro Arg Leu Asn Lys
225                 230                 235                 240 acc gtt ctc aac gag act gag atg cag tcc ctc gtg gac aag aac tgg        768
Thr Val Leu Asn Glu Thr Glu Met Gln Ser Leu Val Asp Lys Asn Trp
                245                 250                 255 acc aag gtt ttc ggc ccc gag aac ggc atg gac cag atc aac tac aaa        816
Thr Lys Val Phe Gly Pro Glu Asn Gly Met Asp Gln Ile Asn Tyr Lys
            260                 265                 270 ctc tgc gcc cgt aag atg ctc atg att gac cgc gtc acc aag att gac        864
Leu Cys Ala Arg Lys Met Leu Met Ile Asp Arg Val Thr Lys Ile Asp
        275                 280                 285 tac acc ggt ggc ccc tac ggc ctt ggt ctc ctc gtt ggt gag aag atc        912
Tyr Thr Gly Gly Pro Tyr Gly Leu Gly Leu Leu Val Gly Glu Lys Ile
    290                 295                 300 ctc gag cgc gac cac tgg tac ttc ccg tgc cac ttc gtc gga gac cag        960
Leu Glu Arg Asp His Trp Tyr Phe Pro Cys His Phe Val Gly Asp Gln
305                 310                 315                 320 gtc atg gct gga tcc ctc gtg tct gac ggc tgc agc cag ctc ctc aag       1008
Val Met Ala Gly Ser Leu Val Ser Asp Gly Cys Ser Gln Leu Leu Lys
                325                 330                 335 atg tac atg ctc tgg ctc ggc ctc cac ctt aag acc ggt ccc ttc gac       1056
Met Tyr Met Leu Trp Leu Gly Leu His Leu Lys Thr Gly Pro Phe Asp
            340                 345                 350 ttc cgc ccc gtc aac ggc cac ccc aac aag gtc cgc tgc cgt ggc cag       1104
Phe Arg Pro Val Asn Gly His Pro Asn Lys Val Arg Cys Arg Gly Gln
        355                 360                 365 atc tcc ccg cac aag ggt aag ctc gtc tac gtc atg gag atc aag gag       1152
Ile Ser Pro His Lys Gly Lys Leu Val Tyr Val Met Glu Ile Lys Glu
    370                 375                 380 atg gga tac gac gag gct ggt gac ccg tac gcc att gcc gat gtc aac       1200
Met Gly Tyr Asp Glu Ala Gly Asp Pro Tyr Ala Ile Ala Asp Val Asn
385                 390                 395                 400 att ctc gac att gac ttc gag aag ggc cag act ttc gac ctt gcc aac       1248
Ile Leu Asp Ile Asp Phe Glu Lys Gly Gln Thr Phe Asp Leu Ala Asn
```

```
                405                      410                      415
ctc cac gag tac ggc aag ggc gac ctc aac aag aag atc gtc gtc gac       1296
Leu His Glu Tyr Gly Lys Gly Asp Leu Asn Lys Lys Ile Val Val Asp
                420                      425                  430 ttc aag ggt att gcc ctc aag ctc cag aag cgc tct ggc cct gcc gtt       1344
Phe Lys Gly Ile Ala Leu Lys Leu Gln Lys Arg Ser Gly Pro Ala Val
            435                      440                  445 gtc gct ccc gag aag ccc ctc gct ctc aac aag gac ctt tgc gcc ccg       1392
Val Ala Pro Glu Lys Pro Leu Ala Leu Asn Lys Asp Leu Cys Ala Pro
        450                      455                  460 gct gtt gag gcc atc cct gag cac atc ctc aag ggc gat gct ctt gcc       1440
Ala Val Glu Ala Ile Pro Glu His Ile Leu Lys Gly Asp Ala Leu Ala
465                      470                  475                  480 cct aac cag atg acc tgg cac ccg atg tcc aag atc gct ggc aac ccc       1488
Pro Asn Gln Met Thr Trp His Pro Met Ser Lys Ile Ala Gly Asn Pro
                    485                  490                  495 acg ccc tcg ttc tct ccc tcg gcc tac cct ccc cgt ccc atc acc ttc       1536
Thr Pro Ser Phe Ser Pro Ser Ala Tyr Pro Pro Arg Pro Ile Thr Phe
                500                  505                  510 acc ccg ttc ccc ggc aac aag aac gac aac aac cac gtg ccc ggc gag       1584
Thr Pro Phe Pro Gly Asn Lys Asn Asp Asn Asn His Val Pro Gly Glu
            515                  520                  525 atg ccg ctc tcg tgg tac aac atg gct gag ttc atg gcc ggc aag gtc       1632
Met Pro Leu Ser Trp Tyr Asn Met Ala Glu Phe Met Ala Gly Lys Val
        530                  535                  540 agc ctc tgc ctc ggc cct gag ttc gcc aag ttc gat gac tcc aac acc       1680
Ser Leu Cys Leu Gly Pro Glu Phe Ala Lys Phe Asp Asp Ser Asn Thr
545                  550                  555                  560 agc cgc agc cct gca tgg gat ctt gct ctt gtg act cgt gtg gtc tcc       1728
Ser Arg Ser Pro Ala Trp Asp Leu Ala Leu Val Thr Arg Val Val Ser
                565                  570                  575 gtt tct gac atg gag tgg gtc cag tgg aag aac gtg gac tgc aac ccg       1776
Val Ser Asp Met Glu Trp Val Gln Trp Lys Asn Val Asp Cys Asn Pro
            580                  585                  590 tcc aag gga acc atg gtt ggc gag ttc gac tgc ccc atc gac gcc tgg       1824
Ser Lys Gly Thr Met Val Gly Glu Phe Asp Cys Pro Ile Asp Ala Trp
        595                  600                  605 ttc ttc cag gga tct tgt aac gac ggc cac atg ccg tac tcc atc ctc       1872
Phe Phe Gln Gly Ser Cys Asn Asp Gly His Met Pro Tyr Ser Ile Leu
    610                  615                  620 atg gag atc gcc ctc cag acc tct ggt gtc ctc acc tct gtg ctc aag       1920
Met Glu Ile Ala Leu Gln Thr Ser Gly Val Leu Thr Ser Val Leu Lys
625                  630                  635                  640 gcc ccg ctc acc atg gag aag aag gac att ctc ttc cgc aac ctt gac       1968
Ala Pro Leu Thr Met Glu Lys Lys Asp Ile Leu Phe Arg Asn Leu Asp
                645                  650                  655 gcc aac gcc gag atg gtt cgc tct gat att gac ctc cgc ggc aag acc       2016
Ala Asn Ala Glu Met Val Arg Ser Asp Ile Asp Leu Arg Gly Lys Thr
            660                  665                  670 atc cac aac ctc acc aag tgt acc ggc tac agc atg ctc gga gac atg       2064
Ile His Asn Leu Thr Lys Cys Thr Gly Tyr Ser Met Leu Gly Asp Met
        675                  680                  685 ggt gtc cac cgc ttc agc ttc gag ctc tct gtt gat ggt gta gtc ttc       2112
Gly Val His Arg Phe Ser Phe Glu Leu Ser Val Asp Gly Val Val Phe
    690                  695                  700 tac aag ggt acc acc tcc ttc ggc tgg ttc gtc cct gag gtc ttc atc       2160
Tyr Lys Gly Thr Thr Ser Phe Gly Trp Phe Val Pro Glu Val Phe Ile
705                  710                  715                  720 tcc cag act ggt ctc gac aac ggt cgc cgc acc cag ccc tgg cac att       2208
```

-continued

```
                Ser Gln Thr Gly Leu Asp Asn Gly Arg Arg Thr Gln Pro Trp His Ile
                                725                 730                 735 gag tcc aag gtg cct tcc gcc cag gtc ctc acc tac gac gtt acc ccc           2256
Glu Ser Lys Val Pro Ser Ala Gln Val Leu Thr Tyr Asp Val Thr Pro
            740                 745                 750 aac ggt gcc ggt cgc acc cag ctc tac gcc aac gct ccc aag ggt gct           2304
Asn Gly Ala Gly Arg Thr Gln Leu Tyr Ala Asn Ala Pro Lys Gly Ala
        755                 760                 765 cag ctc agt cgc cgc tgg aac cag tgc cag tac ctt gac acc atc gac           2352
Gln Leu Ser Arg Arg Trp Asn Gln Cys Gln Tyr Leu Asp Thr Ile Asp
    770                 775                 780 ctt gtg gtc gcc ggt ggc tcc gcc ggt ctt ggc tac ggt cat ggc cgc           2400
Leu Val Val Ala Gly Gly Ser Ala Gly Leu Gly Tyr Gly His Gly Arg
785                 790                 795                 800 aag cag gtg aac ccc aag gac tgg ttc ttc tcg tgc cac ttc tgg ttc           2448
Lys Gln Val Asn Pro Lys Asp Trp Phe Phe Ser Cys His Phe Trp Phe
                805                 810                 815 gac tcc gtc atg ccc ggc tcg ctc ggt gtg gag tct atg ttc cag ctc           2496
Asp Ser Val Met Pro Gly Ser Leu Gly Val Glu Ser Met Phe Gln Leu
            820                 825                 830 gtc gag tcc atc gct gtc aag cag gac ctc gcc ggc aag tac ggc atc           2544
Val Glu Ser Ile Ala Val Lys Gln Asp Leu Ala Gly Lys Tyr Gly Ile
        835                 840                 845 acc aac ccg acc ttc gct cat gct ccg ggc aag atc tcc tgg aag tac           2592
Thr Asn Pro Thr Phe Ala His Ala Pro Gly Lys Ile Ser Trp Lys Tyr
    850                 855                 860 cgt ggt cag ctc acc ccc acc tcc aag ttc atg gac tcc gag gcc cac           2640
Arg Gly Gln Leu Thr Pro Thr Ser Lys Phe Met Asp Ser Glu Ala His
865                 870                 875                 880 att gtc tcc atc gag gcc cac gac ggc gtc gtc gac atc gtt gcc aat           2688
Ile Val Ser Ile Glu Ala His Asp Gly Val Val Asp Ile Val Ala Asn
                885                 890                 895 ggt aac ctc tgg gct gat ggc ctc cgc gtc tac aac gtc agc aac atc           2736
Gly Asn Leu Trp Ala Asp Gly Leu Arg Val Tyr Asn Val Ser Asn Ile
            900                 905                 910 cgt gtt cgc att acc atc acc ctc aag cag ctc aag gct gag ctt ctt           2784
Arg Val Arg Ile Thr Ile Thr Leu Lys Gln Leu Lys Ala Glu Leu Leu
        915                 920                 925 gac gtt gag aag cct ctc tac atc tcc tcc agc aac ggc cag gtc aag           2832
Asp Val Glu Lys Pro Leu Tyr Ile Ser Ser Ser Asn Gly Gln Val Lys
    930                 935                 940 aag cac gcc gat gtg gct ggt ggc cag gcc acc att gtg cag gct tgc           2880
Lys His Ala Asp Val Ala Gly Gly Gln Ala Thr Ile Val Gln Ala Cys
945                 950                 955                 960 agc ctc agt gac ctc ggt gat gaa ggc ttc atg aag acc tac ggt gtt           2928
Ser Leu Ser Asp Leu Gly Asp Glu Gly Phe Met Lys Thr Tyr Gly Val
                965                 970                 975 gtg gct cct ctc tac acc ggt gcc atg gcc aag ggt att gcc tct gct           2976
Val Ala Pro Leu Tyr Thr Gly Ala Met Ala Lys Gly Ile Ala Ser Ala
            980                 985                 990 gac ctt gtg att gcc act ggt aag  cgt aag atc ctc ggt  tcc ttc ggt          3024
Asp Leu Val Ile Ala Thr Gly Lys  Arg Lys Ile Leu Gly  Ser Phe Gly
        995                 1000                1005 gct ggt  ggt ctc ccc atg cac  att gtc cgt gcc gct  gtt gag aag             3069
Ala Gly  Gly Leu Pro Met His  Ile Val Arg Ala Ala  Val Glu Lys
        1010                1015                1020 atc cag gct gag ctc ccg aac  ggc ccc ttc gcc gtc  aac ctc atc             3114
Ile Gln Ala Glu Leu Pro Asn  Gly Pro Phe Ala Val  Asn Leu Ile
        1025                1030                1035
```

```
cac tcc ccc ttc gat agc aac ctt gag aag ggc aac gtt gac ctc      3159
His Ser Pro Phe Asp Ser Asn Leu Glu Lys Gly Asn Val Asp Leu
    1040                1045                1050 ttc ctc gag aag ggc gtc act gtc gtc gag gcc tcc gcc ttc atg      3204
Phe Leu Glu Lys Gly Val Thr Val Val Glu Ala Ser Ala Phe Met
    1055                1060                1065 acc ttg acc ccg caa gtc gtc cgc tac cgt gct gct ggt ctt tcc      3249
Thr Leu Thr Pro Gln Val Val Arg Tyr Arg Ala Ala Gly Leu Ser
    1070                1075                1080 cgt aac gct gat ggc tcc att aac atc aag aac cgc atc atc ggt      3294
Arg Asn Ala Asp Gly Ser Ile Asn Ile Lys Asn Arg Ile Ile Gly
    1085                1090                1095 aag gtc tcc cgt acc gag ctc gct gag atg ttc atc cgc cct gcc      3339
Lys Val Ser Arg Thr Glu Leu Ala Glu Met Phe Ile Arg Pro Ala
    1100                1105                1110 ccg cag aac ctc ctc gac aag ctc atc cag tct ggt gag att acc      3384
Pro Gln Asn Leu Leu Asp Lys Leu Ile Gln Ser Gly Glu Ile Thr
    1115                1120                1125 aag gag cag gct gag ctt gcc aag ctc gtc ccc gtc gcc gac gat      3429
Lys Glu Gln Ala Glu Leu Ala Lys Leu Val Pro Val Ala Asp Asp
    1130                1135                1140 atc gcc gtc gag gcc gac tct ggt ggc cac acc gac aac cgc ccc      3474
Ile Ala Val Glu Ala Asp Ser Gly Gly His Thr Asp Asn Arg Pro
    1145                1150                1155 atc cac gtc atc ctc ccc ctt atc atc aac ctc cgc aac cgc ctc      3519
Ile His Val Ile Leu Pro Leu Ile Ile Asn Leu Arg Asn Arg Leu
    1160                1165                1170 cac aag gag tgc ggc tac ccc gct cac ctc cgc gtg cgc gtt gga      3564
His Lys Glu Cys Gly Tyr Pro Ala His Leu Arg Val Arg Val Gly
    1175                1180                1185 gct ggt ggt ggt gtt gga tgc ccc cag gcc gct gcc gct gct ctc      3609
Ala Gly Gly Gly Val Gly Cys Pro Gln Ala Ala Ala Ala Ala Leu
    1190                1195                1200 gct atg ggt gct gcc ttc ctt gtt acc ggc act gtc aac cag gtc      3654
Ala Met Gly Ala Ala Phe Leu Val Thr Gly Thr Val Asn Gln Val
    1205                1210                1215 gcc aag cag tcc ggc acc tgc gac aat gtc cgc aag cag ctc tgc      3699
Ala Lys Gln Ser Gly Thr Cys Asp Asn Val Arg Lys Gln Leu Cys
    1220                1225                1230 atg gcc acc tac tct gac gtc tgc atg gct ccc gct gct gac atg      3744
Met Ala Thr Tyr Ser Asp Val Cys Met Ala Pro Ala Ala Asp Met
    1235                1240                1245 ttc gag gag ggc gtc aag ctc cag gtc ctc aag aag gga acc atg      3789
Phe Glu Glu Gly Val Lys Leu Gln Val Leu Lys Lys Gly Thr Met
    1250                1255                1260 ttc ccg tcc agg gct aac aag ctc tac gag ctc ttc tgc aag tac      3834
Phe Pro Ser Arg Ala Asn Lys Leu Tyr Glu Leu Phe Cys Lys Tyr
    1265                1270                1275 gac tcc ttc gag tcc atg cct gcc gca gag ctc gag cgt gtt gag      3879
Asp Ser Phe Glu Ser Met Pro Ala Ala Glu Leu Glu Arg Val Glu
    1280                1285                1290 aag cgc atc ttc cag tgc cct ctt gct gat gtc tgg gct gag acc      3924
Lys Arg Ile Phe Gln Cys Pro Leu Ala Asp Val Trp Ala Glu Thr
    1295                1300                1305 tcc gac ttc tac atc aac cgc ctc cac aac ccg gag aag atc acc      3969
Ser Asp Phe Tyr Ile Asn Arg Leu His Asn Pro Glu Lys Ile Thr
    1310                1315                1320 cgt gcc gag cgt gac ccc aag ctc aag atg tct ctc tgc ttc cgc      4014
Arg Ala Glu Arg Asp Pro Lys Leu Lys Met Ser Leu Cys Phe Arg
    1325                1330                1335
```

-continued

```
tgg tac ctt ggt ctt gcc tct cgc tgg gcc aac acc ggt gag gct         4059
Trp Tyr Leu Gly Leu Ala Ser Arg Trp Ala Asn Thr Gly Glu Ala
    1340                1345                1350 gga cgc gtc atg gac tac cag gtc tgg tgt ggc cct gcc att gga         4104
Gly Arg Val Met Asp Tyr Gln Val Trp Cys Gly Pro Ala Ile Gly
1355                1360                1365 gcc ttc aac gac ttc atc aag ggc tcc tac ctt gac ccg gcc gtc         4149
Ala Phe Asn Asp Phe Ile Lys Gly Ser Tyr Leu Asp Pro Ala Val
        1370                1375                1380 tct ggt gag tac ccg gac gtc gtg cag atc aac ttg cag atc ctt         4194
Ser Gly Glu Tyr Pro Asp Val Val Gln Ile Asn Leu Gln Ile Leu
    1385                1390                1395 cgc ggt gcc tgc tac ctc cgc cgt ctc aat gcc atc cgc aac gac         4239
Arg Gly Ala Cys Tyr Leu Arg Arg Leu Asn Ala Ile Arg Asn Asp
1400                1405                1410 ccg cgt gtc agc att gag gtc gag gat gct gag ttc gtc tac gag         4284
Pro Arg Val Ser Ile Glu Val Glu Asp Ala Glu Phe Val Tyr Glu
        1415                1420                1425 ccc acc aac gcc ctc taa                                              4302
Pro Thr Asn Ala Leu
    1430

<210> SEQ ID NO 4
<211> LENGTH: 8733
<212> TYPE: DNA
<213> ORGANISM: Shizochytrium sp.
<220> FEATURE:
<221> NAME/KEY: CDS
<222> LOCATION: (1)..(8733)

<400> SEQUENCE: 4 atg gcg gcc cgt ctg cag gag caa aag gga ggc gag atg gat acc cgc      48
Met Ala Ala Arg Leu Gln Glu Gln Lys Gly Gly Glu Met Asp Thr Arg
1               5                   10                  15 att gcc atc atc ggc atg tcg gcc atc ctc ccc tgc ggc acg acc gtg      96
Ile Ala Ile Ile Gly Met Ser Ala Ile Leu Pro Cys Gly Thr Thr Val
            20                  25                  30 cgc gag tcg tgg gag acc atc cgc gcc ggc atc gac tgc ctg tcg gat     144
Arg Glu Ser Trp Glu Thr Ile Arg Ala Gly Ile Asp Cys Leu Ser Asp
        35                  40                  45 ctc ccc gag gac cgc gtc gac gtg acg gcg tac ttt gac ccc gtc aag     192
Leu Pro Glu Asp Arg Val Asp Val Thr Ala Tyr Phe Asp Pro Val Lys
    50                  55                  60 acc acc aag gac aag atc tac tgc aag cgc ggt ggc ttc att ccc gag     240
Thr Thr Lys Asp Lys Ile Tyr Cys Lys Arg Gly Gly Phe Ile Pro Glu
65                  70                  75                  80 tac gac ttt gac gcc cgc gag ttc gga ctc aac atg ttc cag atg gag     288
Tyr Asp Phe Asp Ala Arg Glu Phe Gly Leu Asn Met Phe Gln Met Glu
                85                  90                  95 gac tcg gac gca aac cag acc atc tcg ctt ctc aag gtc aag gag gcc     336
Asp Ser Asp Ala Asn Gln Thr Ile Ser Leu Leu Lys Val Lys Glu Ala
            100                 105                 110 ctc cag gac gcc ggc atc gac gcc ctc ggc aag gaa aag aag aac atc     384
Leu Gln Asp Ala Gly Ile Asp Ala Leu Gly Lys Glu Lys Lys Asn Ile
        115                 120                 125 ggc tgc gtg ctc ggc att ggc ggc ggc caa aag tcc agc cac gag ttc     432
Gly Cys Val Leu Gly Ile Gly Gly Gly Gln Lys Ser Ser His Glu Phe
    130                 135                 140 tac tcg cgc ctt aat tat gtt gtc gtg gag aag gtc ctc cgc aag atg     480
Tyr Ser Arg Leu Asn Tyr Val Val Val Glu Lys Val Leu Arg Lys Met
145                 150                 155                 160
```

```
ggc atg ccc gag gag gac gtc aag gtc gcc gtc gaa aag tac aag gcc      528
Gly Met Pro Glu Glu Asp Val Lys Val Ala Val Glu Lys Tyr Lys Ala
            165                 170                 175 aac ttc ccc gag tgg cgc ctc gac tcc ttc cct ggc ttc ctc ggc aac      576
Asn Phe Pro Glu Trp Arg Leu Asp Ser Phe Pro Gly Phe Leu Gly Asn
            180                 185                 190 gtc acc gcc ggt cgc tgc acc aac acc ttc aac ctc gac ggc atg aac      624
Val Thr Ala Gly Arg Cys Thr Asn Thr Phe Asn Leu Asp Gly Met Asn
            195                 200                 205 tgc gtt gtc gac gcc gca tgc gcc tcg tcc ctc atc gcc gtc aag gtc      672
Cys Val Val Asp Ala Ala Cys Ala Ser Ser Leu Ile Ala Val Lys Val
210                 215                 220 gcc atc gac gag ctg ctc tac ggt gac tgc gac atg atg gtc acc ggt      720
Ala Ile Asp Glu Leu Leu Tyr Gly Asp Cys Asp Met Met Val Thr Gly
225                 230                 235                 240 gcc acc tgc acg gat aac tcc atc ggc atg tac atg gcc ttc tcc aag      768
Ala Thr Cys Thr Asp Asn Ser Ile Gly Met Tyr Met Ala Phe Ser Lys
            245                 250                 255 acc ccc gtg ttc tcc acg gac ccc agc gtg cgc gcc tac gac gaa aag      816
Thr Pro Val Phe Ser Thr Asp Pro Ser Val Arg Ala Tyr Asp Glu Lys
            260                 265                 270 aca aag ggc atg ctc atc ggc gag ggc tcc gcc atg ctc gtc ctc aag      864
Thr Lys Gly Met Leu Ile Gly Glu Gly Ser Ala Met Leu Val Leu Lys
            275                 280                 285 cgc tac gcc gac gcc gtc cgc gac ggc gat gag atc cac gct gtt att      912
Arg Tyr Ala Asp Ala Val Arg Asp Gly Asp Glu Ile His Ala Val Ile
            290                 295                 300 cgc ggc tgc gcc tcc tcc agt gat ggc aag gcc gcc ggc atc tac acg      960
Arg Gly Cys Ala Ser Ser Ser Asp Gly Lys Ala Ala Gly Ile Tyr Thr
305                 310                 315                 320 ccc acc att tcg ggc cag gag gag gcc ctc cgc cgc gcc tac aac cgc     1008
Pro Thr Ile Ser Gly Gln Glu Glu Ala Leu Arg Arg Ala Tyr Asn Arg
            325                 330                 335 gcc tgt gtc gac ccg gcc acc gtc act ctc gtc gag ggt cac ggc acc     1056
Ala Cys Val Asp Pro Ala Thr Val Thr Leu Val Glu Gly His Gly Thr
            340                 345                 350 ggt act ccc gtt ggc gac cgc atc gag ctc acc gcc ttg cgc aac ctc     1104
Gly Thr Pro Val Gly Asp Arg Ile Glu Leu Thr Ala Leu Arg Asn Leu
            355                 360                 365 ttt gac aag gcc tac ggc gag ggc aac acc gaa aag gtc gct gtg ggc     1152
Phe Asp Lys Ala Tyr Gly Glu Gly Asn Thr Glu Lys Val Ala Val Gly
            370                 375                 380 agc atc aag tcc agc atc ggc cat ctc aag gcc gtc gcc ggt ctc gcc     1200
Ser Ile Lys Ser Ser Ile Gly His Leu Lys Ala Val Ala Gly Leu Ala
385                 390                 395                 400 ggt atg atc aag gtc atc atg gcg ctc aag cac aag act ctc ccg ggc     1248
Gly Met Ile Lys Val Ile Met Ala Leu Lys His Lys Thr Leu Pro Gly
            405                 410                 415 acc atc aac gtc gac aac cca ccc aac ctc tac gac aac acg ccc atc     1296
Thr Ile Asn Val Asp Asn Pro Pro Asn Leu Tyr Asp Asn Thr Pro Ile
            420                 425                 430 aac gag tcc tcg ctc tac att aac acc atg aac cgc ccc tgg ttc ccg     1344
Asn Glu Ser Ser Leu Tyr Ile Asn Thr Met Asn Arg Pro Trp Phe Pro
            435                 440                 445 ccc cct ggt gtg ccc cgc cgc gcc ggc att tcg agc ttt ggc ttt ggt     1392
Pro Pro Gly Val Pro Arg Arg Ala Gly Ile Ser Ser Phe Gly Phe Gly
450                 455                 460 ggc gcc aac tac cac gcc gtc ctc gag gag gcc gag ccc gag cac acg     1440
Gly Ala Asn Tyr His Ala Val Leu Glu Glu Ala Glu Pro Glu His Thr
```

```
                                         -continued
465              470              475              480
acc gcg tac cgc ctc aac aag cgc ccg cag ccc gtg ctc atg atg gcc      1488
Thr Ala Tyr Arg Leu Asn Lys Arg Pro Gln Pro Val Leu Met Met Ala
                485              490              495 gcc acg ccc gcg gcc ctc cag tcg ctc tgc gag gcc cag ctc aag gag      1536
Ala Thr Pro Ala Ala Leu Gln Ser Leu Cys Glu Ala Gln Leu Lys Glu
            500              505              510 ttc gag gcc gcc atc aag gag aac gag acc gtc aag aac acc gcc tac      1584
Phe Glu Ala Ala Ile Lys Glu Asn Glu Thr Val Lys Asn Thr Ala Tyr
        515              520              525 atc aag tgc gtc aag ttc ggc gag cag ttc aaa ttc cct ggc tcc atc      1632
Ile Lys Cys Val Lys Phe Gly Glu Gln Phe Lys Phe Pro Gly Ser Ile
    530              535              540 ccg gcc aca aac gcg cgc ctc ggc ttc ctc gtc aag gat gct gag gat      1680
Pro Ala Thr Asn Ala Arg Leu Gly Phe Leu Val Lys Asp Ala Glu Asp
545              550              555              560 gcc tgc tcc acc ctc cgt gcc atc tgc gcc caa ttc gcc aag gat gtc      1728
Ala Cys Ser Thr Leu Arg Ala Ile Cys Ala Gln Phe Ala Lys Asp Val
                565              570              575 acc aag gag gcc tgg cgc ctc ccc cgc gag ggc gtc agc ttc cgc gcc      1776
Thr Lys Glu Ala Trp Arg Leu Pro Arg Glu Gly Val Ser Phe Arg Ala
            580              585              590 aag ggc atc gcc acc aac ggc gct gtc gcc gcg ctc ttc tcc ggc cag      1824
Lys Gly Ile Ala Thr Asn Gly Ala Val Ala Ala Leu Phe Ser Gly Gln
        595              600              605 ggc gcg cag tac acg cac atg ttt agc gag gtg gcc atg aac tgg ccc      1872
Gly Ala Gln Tyr Thr His Met Phe Ser Glu Val Ala Met Asn Trp Pro
    610              615              620 cag ttc cgc cag agc att gcc gcc atg gac gcc gcc cag tcc aag gtc      1920
Gln Phe Arg Gln Ser Ile Ala Ala Met Asp Ala Ala Gln Ser Lys Val
625              630              635              640 gct gga agc gac aag gac ttt gag cgc gtc tcc cag gtc ctc tac ccg      1968
Ala Gly Ser Asp Lys Asp Phe Glu Arg Val Ser Gln Val Leu Tyr Pro
                645              650              655 cgc aag ccg tac gag cgt gag ccc gag cag gac cac aag aag atc tcc      2016
Arg Lys Pro Tyr Glu Arg Glu Pro Glu Gln Asp His Lys Lys Ile Ser
            660              665              670 ctc acc gcc tac tcg cag ccc tcg acc ctg gcc tgc gct ctc ggt gcc      2064
Leu Thr Ala Tyr Ser Gln Pro Ser Thr Leu Ala Cys Ala Leu Gly Ala
        675              680              685 ttt gag atc ttc aag gag gcc ggc ttc acc ccg gac ttt gcc gcc ggc      2112
Phe Glu Ile Phe Lys Glu Ala Gly Phe Thr Pro Asp Phe Ala Ala Gly
    690              695              700 cat tcg ctc ggt gag ttc gcc gcc ctc tac gcc gcg ggc tgc gtc gac      2160
His Ser Leu Gly Glu Phe Ala Ala Leu Tyr Ala Ala Gly Cys Val Asp
705              710              715              720 cgc gac gag ctc ttt gag ctt gtc tgc cgc cgc gcc cgc atc atg ggc      2208
Arg Asp Glu Leu Phe Glu Leu Val Cys Arg Arg Ala Arg Ile Met Gly
                725              730              735 ggc aag gac gca ccg gcc acc ccc aag ggc tgc atg gcc gcc gtc att      2256
Gly Lys Asp Ala Pro Ala Thr Pro Lys Gly Cys Met Ala Ala Val Ile
            740              745              750 ggc ccc aac gcc gag aac atc aag gtc cag gcc gcc aac gtc tgg ctc      2304
Gly Pro Asn Ala Glu Asn Ile Lys Val Gln Ala Ala Asn Val Trp Leu
        755              760              765 ggc aac tcc aac tcg cct tcg cag acc gtc atc acc ggc tcc gtc gaa      2352
Gly Asn Ser Asn Ser Pro Ser Gln Thr Val Ile Thr Gly Ser Val Glu
    770              775              780 ggt atc cag gcc gag agc gcc cgc ctc cag aag gag ggc ttc cgc gtc      2400
```

-continued

| | | |
|---|---|---|
| Gly Ile Gln Ala Glu Ser Ala Arg Leu Gln Lys Glu Gly Phe Arg Val<br>785               790               795              800 | | |
| gtg cct ctt gcc tgc gag agc gcc ttc cac tcg ccc cag atg gag aac<br>Val Pro Leu Ala Cys Glu Ser Ala Phe His Ser Pro Gln Met Glu Asn<br>                      805                     810               815 | 2448 |
| gcc tcg tcg gcc ttc aag gac gtc atc tcc aag gtc tcc ttc cgc acc<br>Ala Ser Ser Ala Phe Lys Asp Val Ile Ser Lys Val Ser Phe Arg Thr<br>                820                 825               830 | 2496 |
| ccc aag gcc gag acc aag ctc ttc agc aac gtc tct ggc gag acc tac<br>Pro Lys Ala Glu Thr Lys Leu Phe Ser Asn Val Ser Gly Glu Thr Tyr<br>        835                 840               845 | 2544 |
| ccc acg gac gcc cgc gag atg ctt acg cag cac atg acc agc agc gtc<br>Pro Thr Asp Ala Arg Glu Met Leu Thr Gln His Met Thr Ser Ser Val<br>850               855               860 | 2592 |
| aag ttc ctc acc cag gtc cgc aac atg cac cag gcc ggt gcg cgc atc<br>Lys Phe Leu Thr Gln Val Arg Asn Met His Gln Ala Gly Ala Arg Ile<br>865               870               875              880 | 2640 |
| ttt gtc gag ttc gga ccc aag cag gtg ctc tcc aag ctt gtc tcc gag<br>Phe Val Glu Phe Gly Pro Lys Gln Val Leu Ser Lys Leu Val Ser Glu<br>                        885                     890               895 | 2688 |
| acc ctc aag gat gac ccc tcg gtt gtc acc gtc tct gtc aac ccg gcc<br>Thr Leu Lys Asp Asp Pro Ser Val Val Thr Val Ser Val Asn Pro Ala<br>        900                 905               910 | 2736 |
| tcg ggc acg gat tcg gac atc cag ctc cgc gac gcg gcc gtc cag ctc<br>Ser Gly Thr Asp Ser Asp Ile Gln Leu Arg Asp Ala Ala Val Gln Leu<br>915               920               925 | 2784 |
| gtt gtc gct ggc gtc aac ctt cag ggc ttt gac aag tgg gac gcc ccc<br>Val Val Ala Gly Val Asn Leu Gln Gly Phe Asp Lys Trp Asp Ala Pro<br>930               935               940 | 2832 |
| gat gcc acc cgc atg cag gcc atc aag aag aag cgc act acc ctc cgc<br>Asp Ala Thr Arg Met Gln Ala Ile Lys Lys Lys Arg Thr Thr Leu Arg<br>945               950               955              960 | 2880 |
| ctt tcg gcc gcc acc tac gtc tcg gac aag acc aag aag gtc cgc gac<br>Leu Ser Ala Ala Thr Tyr Val Ser Asp Lys Thr Lys Lys Val Arg Asp<br>                965               970               975 | 2928 |
| gcc gcc atg aac gat ggc cgc tgc gtc acc tac ctc aag ggc gcc gca<br>Ala Ala Met Asn Asp Gly Arg Cys Val Thr Tyr Leu Lys Gly Ala Ala<br>        980               985               990 | 2976 |
| ccg ctc atc aag gcc ccg gag ccc gtt gtc gac gag gcc gcc aag cgc<br>Pro Leu Ile Lys Ala Pro Glu Pro Val Val Asp Glu Ala Ala Lys Arg<br>995               1000            1005 | 3024 |
| gag gcc gag cgt ctc cag aag gag ctt cag gat gcc cag cgc cag<br>Glu Ala Glu Arg Leu Gln Lys Glu Leu Gln Asp Ala Gln Arg Gln<br>     1010               1015             1020 | 3069 |
| ctc gac gac gcc aag cgc gcc gcc gcc gag gcc aac tcc aag ctc<br>Leu Asp Asp Ala Lys Arg Ala Ala Ala Glu Ala Asn Ser Lys Leu<br>1025             1030             1035 | 3114 |
| gcc gct gcc aag gag gag gcc aag acc gcc gct gct tcg gcc aag<br>Ala Ala Ala Lys Glu Glu Ala Lys Thr Ala Ala Ala Ser Ala Lys<br>    1040              1045            1050 | 3159 |
| ccc gca gtt gac act gct gtt gtc gaa aag cat cgt gcc atc ctc<br>Pro Ala Val Asp Thr Ala Val Val Glu Lys His Arg Ala Ile Leu<br>1055             1060             1065 | 3204 |
| aag tcc atg ctc gcg gag ctc gat ggc tac gga tcg gtc gac gct<br>Lys Ser Met Leu Ala Glu Leu Asp Gly Tyr Gly Ser Val Asp Ala<br>    1070              1075            1080 | 3249 |
| tct tcc ctc cag cag cag cag cag cag cag acg gcc ccc gcc ccg<br>Ser Ser Leu Gln Gln Gln Gln Gln Gln Gln Thr Ala Pro Ala Pro<br>1085             1090             1095 | 3294 |

| | | | | | | | | | | | | | | |
|---|---|---|---|---|---|---|---|---|---|---|---|---|---|---|
| gtc | aag | gct | gct | gcg | cct | gcc | gcc | ccc | gtt | gcc | tcg | gcc | cct | gcc | 3339 |
| Val | Lys | Ala | Ala | Ala | Pro | Ala | Ala | Pro | Val | Ala | Ser | Ala | Pro | Ala | |
| | 1100 | | | | 1105 | | | | | 1110 | | | | | |

| ccg | gct | gtc | tcg | aac | gag | ctt | ctt | gag | aag | gcc | gag | act | gtc | gtc | 3384 |
| Pro | Ala | Val | Ser | Asn | Glu | Leu | Leu | Glu | Lys | Ala | Glu | Thr | Val | Val | |
| 1115 | | | | | 1120 | | | | | 1125 | | | | | |

| atg | gag | gtc | ctc | gcc | gcc | aag | acc | ggc | tac | gag | acc | gac | atg | atc | 3429 |
| Met | Glu | Val | Leu | Ala | Ala | Lys | Thr | Gly | Tyr | Glu | Thr | Asp | Met | Ile | |
| | 1130 | | | | 1135 | | | | | 1140 | | | | | |

| gag | gct | gac | atg | gag | ctc | gag | acc | gag | ctc | ggc | att | gac | tcc | atc | 3474 |
| Glu | Ala | Asp | Met | Glu | Leu | Glu | Thr | Glu | Leu | Gly | Ile | Asp | Ser | Ile | |
| 1145 | | | | | 1150 | | | | | 1155 | | | | | |

| aag | cgt | gtc | gag | atc | ctc | tcc | gag | gtc | cag | gcc | atg | ctc | aat | gtc | 3519 |
| Lys | Arg | Val | Glu | Ile | Leu | Ser | Glu | Val | Gln | Ala | Met | Leu | Asn | Val | |
| | 1160 | | | | 1165 | | | | | 1170 | | | | | |

| gag | gcc | aag | gat | gtc | gat | gcc | ctc | agc | cgc | act | cgc | act | gtt | ggt | 3564 |
| Glu | Ala | Lys | Asp | Val | Asp | Ala | Leu | Ser | Arg | Thr | Arg | Thr | Val | Gly | |
| 1175 | | | | | 1180 | | | | | 1185 | | | | | |

| gag | gtt | gtc | aac | gcc | atg | aag | gcc | gag | atc | gct | ggc | agc | tct | gcc | 3609 |
| Glu | Val | Val | Asn | Ala | Met | Lys | Ala | Glu | Ile | Ala | Gly | Ser | Ser | Ala | |
| | 1190 | | | | 1195 | | | | | 1200 | | | | | |

| ccg | gcg | cct | gct | gcc | gct | gct | ccg | gct | ccg | gcc | aag | gct | gcc | cct | 3654 |
| Pro | Ala | Pro | Ala | Ala | Ala | Ala | Pro | Ala | Pro | Ala | Lys | Ala | Ala | Pro | |
| 1205 | | | | | 1210 | | | | | 1215 | | | | | |

| gcc | gcc | gct | gcg | cct | gct | gtc | tcg | aac | gag | ctt | ctc | gag | aag | gcc | 3699 |
| Ala | Ala | Ala | Ala | Pro | Ala | Val | Ser | Asn | Glu | Leu | Leu | Glu | Lys | Ala | |
| | 1220 | | | | 1225 | | | | | 1230 | | | | | |

| gag | acc | gtc | gtc | atg | gag | gtc | ctc | gcc | gcc | aag | act | ggc | tac | gag | 3744 |
| Glu | Thr | Val | Val | Met | Glu | Val | Leu | Ala | Ala | Lys | Thr | Gly | Tyr | Glu | |
| 1235 | | | | | 1240 | | | | | 1245 | | | | | |

| act | gac | atg | atc | gag | tcc | gac | atg | gag | ctc | gag | act | gag | ctc | ggc | 3789 |
| Thr | Asp | Met | Ile | Glu | Ser | Asp | Met | Glu | Leu | Glu | Thr | Glu | Leu | Gly | |
| | 1250 | | | | 1255 | | | | | 1260 | | | | | |

| att | gac | tcc | atc | aag | cgt | gtc | gag | atc | ctc | tcc | gag | gtt | cag | gcc | 3834 |
| Ile | Asp | Ser | Ile | Lys | Arg | Val | Glu | Ile | Leu | Ser | Glu | Val | Gln | Ala | |
| 1265 | | | | | 1270 | | | | | 1275 | | | | | |

| atg | ctc | aac | gtc | gag | gcc | aag | gac | gtc | gac | gct | ctc | agc | cgc | act | 3879 |
| Met | Leu | Asn | Val | Glu | Ala | Lys | Asp | Val | Asp | Ala | Leu | Ser | Arg | Thr | |
| | 1280 | | | | 1285 | | | | | 1290 | | | | | |

| cgc | act | gtg | ggt | gag | gtc | gtc | aac | gcc | atg | aag | gct | gag | atc | gct | 3924 |
| Arg | Thr | Val | Gly | Glu | Val | Val | Asn | Ala | Met | Lys | Ala | Glu | Ile | Ala | |
| 1295 | | | | | 1300 | | | | | 1305 | | | | | |

| ggt | ggc | tct | gcc | ccg | gcg | cct | gcc | gcc | gct | gcc | cca | ggt | ccg | gct | 3969 |
| Gly | Gly | Ser | Ala | Pro | Ala | Pro | Ala | Ala | Ala | Ala | Pro | Gly | Pro | Ala | |
| | 1310 | | | | 1315 | | | | | 1320 | | | | | |

| gct | gcc | gcc | cct | gcg | cct | gcc | gcc | gcc | cct | gct | gtc | tcg | aac | 4014 |
| Ala | Ala | Ala | Pro | Ala | Pro | Ala | Ala | Ala | Pro | Ala | Val | Ser | Asn | |
| 1325 | | | | | 1330 | | | | | 1335 | | | | | |

| gag | ctt | ctt | gag | aag | gcc | gag | acc | gtc | gtc | atg | gag | gtc | ctc | gcc | 4059 |
| Glu | Leu | Leu | Glu | Lys | Ala | Glu | Thr | Val | Val | Met | Glu | Val | Leu | Ala | |
| | 1340 | | | | 1345 | | | | | 1350 | | | | | |

| gcc | aag | act | ggc | tac | gag | act | gac | atg | atc | gag | tcc | gac | atg | gag | 4104 |
| Ala | Lys | Thr | Gly | Tyr | Glu | Thr | Asp | Met | Ile | Glu | Ser | Asp | Met | Glu | |
| 1355 | | | | | 1360 | | | | | 1365 | | | | | |

| ctc | gag | acc | gag | ctc | ggc | att | gac | tcc | atc | aag | cgt | gtc | gag | att | 4149 |
| Leu | Glu | Thr | Glu | Leu | Gly | Ile | Asp | Ser | Ile | Lys | Arg | Val | Glu | Ile | |
| | 1370 | | | | 1375 | | | | | 1380 | | | | | |

| ctc | tcc | gag | gtc | cag | gcc | atg | ctc | aac | gtc | gag | gcc | aag | gac | gtc | 4194 |
| Leu | Ser | Glu | Val | Gln | Ala | Met | Leu | Asn | Val | Glu | Ala | Lys | Asp | Val | |
| 1385 | | | | | 1390 | | | | | 1395 | | | | | |

-continued

| | | | | | | | | | | | | |
|---|---|---|---|---|---|---|---|---|---|---|---|---|
| gac | gct | ctc | agc | cgc | acc | cgc | act | gtt | ggc | gag | gtc | gtc | gat | gcc | 4239 |
| Asp | Ala | Leu | Ser | Arg | Thr | Arg | Thr | Val | Gly | Glu | Val | Val | Asp | Ala | |
| | 1400 | | | | 1405 | | | | | 1410 | | | | | |
| atg | aag | gcc | gag | atc | gct | ggt | ggc | tct | gcc | ccg | gcg | cct | gcc | gcc | 4284 |
| Met | Lys | Ala | Glu | Ile | Ala | Gly | Gly | Ser | Ala | Pro | Ala | Pro | Ala | Ala | |
| 1415 | | | | | 1420 | | | | | 1425 | | | | | |
| gct | gct | cct | gct | ccg | gct | gct | gcc | gcc | cct | gcg | cct | gcc | gcc | cct | 4329 |
| Ala | Ala | Pro | Ala | Pro | Ala | Ala | Ala | Ala | Pro | Ala | Pro | Ala | Ala | Pro | |
| | 1430 | | | | | 1435 | | | | | 1440 | | | | |
| gcg | cct | gct | gtc | tcg | agc | gag | ctt | ctc | gag | aag | gcc | gag | act | gtc | 4374 |
| Ala | Pro | Ala | Val | Ser | Ser | Glu | Leu | Leu | Glu | Lys | Ala | Glu | Thr | Val | |
| 1445 | | | | | 1450 | | | | | 1455 | | | | | |
| gtc | atg | gag | gtc | ctc | gcc | gcc | aag | act | ggc | tac | gag | act | gac | atg | 4419 |
| Val | Met | Glu | Val | Leu | Ala | Ala | Lys | Thr | Gly | Tyr | Glu | Thr | Asp | Met | |
| | 1460 | | | | | 1465 | | | | | 1470 | | | | |
| atc | gag | tcc | gac | atg | gag | ctc | gag | acc | gag | ctc | ggc | att | gac | tcc | 4464 |
| Ile | Glu | Ser | Asp | Met | Glu | Leu | Glu | Thr | Glu | Leu | Gly | Ile | Asp | Ser | |
| 1475 | | | | | 1480 | | | | | 1485 | | | | | |
| atc | aag | cgt | gtc | gag | att | ctc | tcc | gag | gtc | cag | gcc | atg | ctc | aac | 4509 |
| Ile | Lys | Arg | Val | Glu | Ile | Leu | Ser | Glu | Val | Gln | Ala | Met | Leu | Asn | |
| | 1490 | | | | | 1495 | | | | | 1500 | | | | |
| gtc | gag | gcc | aag | gac | gtc | gac | gct | ctc | agc | cgc | acc | cgc | act | gtt | 4554 |
| Val | Glu | Ala | Lys | Asp | Val | Asp | Ala | Leu | Ser | Arg | Thr | Arg | Thr | Val | |
| 1505 | | | | | 1510 | | | | | 1515 | | | | | |
| ggc | gag | gtc | gtc | gat | gcc | atg | aag | gcc | gag | atc | gct | ggt | ggc | tct | 4599 |
| Gly | Glu | Val | Val | Asp | Ala | Met | Lys | Ala | Glu | Ile | Ala | Gly | Gly | Ser | |
| | 1520 | | | | | 1525 | | | | | 1530 | | | | |
| gcc | ccg | gcg | cct | gcc | gcc | gct | gct | cct | gct | ccg | gct | gct | gcc | gcc | 4644 |
| Ala | Pro | Ala | Pro | Ala | Ala | Ala | Ala | Pro | Ala | Pro | Ala | Ala | Ala | Ala | |
| 1535 | | | | | 1540 | | | | | 1545 | | | | | |
| cct | gcg | cct | gcc | gcc | cct | gcg | cct | gcc | gcc | cct | gcg | cct | gct | gtc | 4689 |
| Pro | Ala | Pro | Ala | Ala | Pro | Ala | Pro | Ala | Ala | Pro | Ala | Pro | Ala | Val | |
| | 1550 | | | | | 1555 | | | | | 1560 | | | | |
| tcg | agc | gag | ctt | ctc | gag | aag | gcc | gag | act | gtc | gtc | atg | gag | gtc | 4734 |
| Ser | Ser | Glu | Leu | Leu | Glu | Lys | Ala | Glu | Thr | Val | Val | Met | Glu | Val | |
| 1565 | | | | | 1570 | | | | | 1575 | | | | | |
| ctc | gcc | gcc | aag | act | ggc | tac | gag | act | gac | atg | att | gag | tcc | gac | 4779 |
| Leu | Ala | Ala | Lys | Thr | Gly | Tyr | Glu | Thr | Asp | Met | Ile | Glu | Ser | Asp | |
| | 1580 | | | | | 1585 | | | | | 1590 | | | | |
| atg | gag | ctc | gag | acc | gag | ctc | ggc | att | gac | tcc | atc | aag | cgt | gtc | 4824 |
| Met | Glu | Leu | Glu | Thr | Glu | Leu | Gly | Ile | Asp | Ser | Ile | Lys | Arg | Val | |
| 1595 | | | | | 1600 | | | | | 1605 | | | | | |
| gag | att | ctc | tcc | gag | gtt | cag | gcc | atg | ctc | aac | gtc | gag | gcc | aag | 4869 |
| Glu | Ile | Leu | Ser | Glu | Val | Gln | Ala | Met | Leu | Asn | Val | Glu | Ala | Lys | |
| | 1610 | | | | | 1615 | | | | | 1620 | | | | |
| gac | gtc | gac | gct | ctc | agc | cgc | act | cgc | act | gtt | ggt | gag | gtc | gtc | 4914 |
| Asp | Val | Asp | Ala | Leu | Ser | Arg | Thr | Arg | Thr | Val | Gly | Glu | Val | Val | |
| 1625 | | | | | 1630 | | | | | 1635 | | | | | |
| gat | gcc | atg | aag | gct | gag | atc | gct | ggc | agc | tcc | gcc | tcg | gcg | cct | 4959 |
| Asp | Ala | Met | Lys | Ala | Glu | Ile | Ala | Gly | Ser | Ser | Ala | Ser | Ala | Pro | |
| | 1640 | | | | | 1645 | | | | | 1650 | | | | |
| gcc | gcc | gct | gct | cct | gct | ccg | gct | gct | gcc | gct | cct | gcg | ccc | gct | 5004 |
| Ala | Ala | Ala | Ala | Pro | Ala | Pro | Ala | Ala | Ala | Ala | Pro | Ala | Pro | Ala | |
| 1655 | | | | | 1660 | | | | | 1665 | | | | | |
| gcc | gcc | gcc | cct | gct | gtc | tcg | aac | gag | ctt | ctc | gag | aaa | gcc | gag | 5049 |
| Ala | Ala | Ala | Pro | Ala | Val | Ser | Asn | Glu | Leu | Leu | Glu | Lys | Ala | Glu | |
| | 1670 | | | | | 1675 | | | | | 1680 | | | | |
| act | gtc | gtc | atg | gag | gtc | ctc | gcc | gcc | aag | act | ggc | tac | gag | act | 5094 |
| Thr | Val | Val | Met | Glu | Val | Leu | Ala | Ala | Lys | Thr | Gly | Tyr | Glu | Thr | |

-continued

```
              1685                1690                1695
gac atg atc gag tcc gac atg gag ctc gag act gag ctc ggc att        5139
Asp Met Ile Glu Ser Asp Met Glu Leu Glu Thr Glu Leu Gly Ile
    1700                1705                1710 gac tcc atc aag cgt gtc gag atc ctc tcc gag gtt cag gcc atg        5184
Asp Ser Ile Lys Arg Val Glu Ile Leu Ser Glu Val Gln Ala Met
    1715                1720                1725 ctc aac gtc gag gcc aag gac gtc gat gcc ctc agc cgc acc cgc        5229
Leu Asn Val Glu Ala Lys Asp Val Asp Ala Leu Ser Arg Thr Arg
    1730                1735                1740 act gtt ggc gag gtt gtc gat gcc atg aag gcc gag atc gct ggt        5274
Thr Val Gly Glu Val Val Asp Ala Met Lys Ala Glu Ile Ala Gly
    1745                1750                1755 ggc tct gcc ccg gcg cct gcc gcc gct gcc cct gct ccg gct gcc        5319
Gly Ser Ala Pro Ala Pro Ala Ala Ala Pro Ala Pro Ala Ala
    1760                1765                1770 gcc gcc cct gct gtc tcg aac gag ctt ctc gag aag gcc gag act        5364
Ala Ala Pro Ala Val Ser Asn Glu Leu Leu Glu Lys Ala Glu Thr
    1775                1780                1785 gtc gtc atg gag gtc ctc gcc gcc aag act ggc tac gag acc gac        5409
Val Val Met Glu Val Leu Ala Ala Lys Thr Gly Tyr Glu Thr Asp
    1790                1795                1800 atg atc gag tcc gac atg gag ctc gag acc gag ctc ggc att gac        5454
Met Ile Glu Ser Asp Met Glu Leu Glu Thr Glu Leu Gly Ile Asp
    1805                1810                1815 tcc atc aag cgt gtc gag att ctc tcc gag gtt cag gcc atg ctc        5499
Ser Ile Lys Arg Val Glu Ile Leu Ser Glu Val Gln Ala Met Leu
    1820                1825                1830 aac gtc gag gcc aag gac gtc gat gct ctc agc cgc act cgc act        5544
Asn Val Glu Ala Lys Asp Val Asp Ala Leu Ser Arg Thr Arg Thr
    1835                1840                1845 gtt ggc gag gtc gtc gat gcc atg aag gct gag atc gcc ggc agc        5589
Val Gly Glu Val Val Asp Ala Met Lys Ala Glu Ile Ala Gly Ser
    1850                1855                1860 tcc gcc ccg gcg cct gcc gcc gct gct cct gct ccg gct gct gcc        5634
Ser Ala Pro Ala Pro Ala Ala Ala Ala Pro Ala Pro Ala Ala Ala
    1865                1870                1875 gct cct gcg ccc gct gcc gct gcc cct gct gtc tcg agc gag ctt        5679
Ala Pro Ala Pro Ala Ala Ala Pro Ala Val Ser Ser Glu Leu
    1880                1885                1890 ctc gag aag gcc gag acc gtc gtc atg gag gtc ctc gcc gcc aag        5724
Leu Glu Lys Ala Glu Thr Val Val Met Glu Val Leu Ala Ala Lys
    1895                1900                1905 act ggc tac gag act gac atg att gag tcc gac atg gag ctc gag        5769
Thr Gly Tyr Glu Thr Asp Met Ile Glu Ser Asp Met Glu Leu Glu
    1910                1915                1920 act gag ctc ggc att gac tcc atc aag cgt gtc gag atc ctc tcc        5814
Thr Glu Leu Gly Ile Asp Ser Ile Lys Arg Val Glu Ile Leu Ser
    1925                1930                1935 gag gtt cag gcc atg ctc aac gtc gag gcc aag gac gtc gat gcc        5859
Glu Val Gln Ala Met Leu Asn Val Glu Ala Lys Asp Val Asp Ala
    1940                1945                1950 ctc agc cgc acc cgc act gtt ggc gag gtt gtc gat gcc atg aag        5904
Leu Ser Arg Thr Arg Thr Val Gly Glu Val Val Asp Ala Met Lys
    1955                1960                1965 gcc gag atc gct ggt ggc tct gcc ccg gcg cct gcc gcc gct gcc        5949
Ala Glu Ile Ala Gly Gly Ser Ala Pro Ala Pro Ala Ala Ala
    1970                1975                1980 cct gct ccg gct gcc gcc gcc cct gct gtc tcg aac gag ctt ctt        5994
```

|     |     |     |     |     |     |     |     |     |     |     |     |     |     |     |     |
|---|---|---|---|---|---|---|---|---|---|---|---|---|---|---|---|
| Pro | Ala | Pro | Ala | Ala | Ala | Ala | Pro | Ala | Val | Ser | Asn | Glu | Leu | Leu | |
| 1985 | | | | 1990 | | | | | 1995 | | | | | | |

| gag | aag | gcc | gag | acc | gtc | gtc | atg | gag | gtc | ctc | gcc | gcc | aag | act | 6039 |
|---|---|---|---|---|---|---|---|---|---|---|---|---|---|---|---|
| Glu | Lys | Ala | Glu | Thr | Val | Val | Met | Glu | Val | Leu | Ala | Ala | Lys | Thr | |
| 2000 | | | | | 2005 | | | | | 2010 | | | | | |

| ggc | tac | gag | acc | gac | atg | atc | gag | tcc | gac | atg | gag | ctc | gag | acc | 6084 |
|---|---|---|---|---|---|---|---|---|---|---|---|---|---|---|---|
| Gly | Tyr | Glu | Thr | Asp | Met | Ile | Glu | Ser | Asp | Met | Glu | Leu | Glu | Thr | |
| 2015 | | | | | 2020 | | | | | 2025 | | | | | |

| gag | ctc | ggc | att | gac | tcc | atc | aag | cgt | gtc | gag | att | ctc | tcc | gag | 6129 |
|---|---|---|---|---|---|---|---|---|---|---|---|---|---|---|---|
| Glu | Leu | Gly | Ile | Asp | Ser | Ile | Lys | Arg | Val | Glu | Ile | Leu | Ser | Glu | |
| 2030 | | | | | 2035 | | | | | 2040 | | | | | |

| gtt | cag | gcc | atg | ctc | aac | gtc | gag | gcc | aag | gac | gtc | gac | gct | ctc | 6174 |
|---|---|---|---|---|---|---|---|---|---|---|---|---|---|---|---|
| Val | Gln | Ala | Met | Leu | Asn | Val | Glu | Ala | Lys | Asp | Val | Asp | Ala | Leu | |
| 2045 | | | | | 2050 | | | | | 2055 | | | | | |

| agc | cgc | act | cgc | act | gtt | ggc | gag | gtc | gtc | gat | gcc | atg | aag | gct | 6219 |
|---|---|---|---|---|---|---|---|---|---|---|---|---|---|---|---|
| Ser | Arg | Thr | Arg | Thr | Val | Gly | Glu | Val | Val | Asp | Ala | Met | Lys | Ala | |
| 2060 | | | | | 2065 | | | | | 2070 | | | | | |

| gag | atc | gct | ggt | ggc | tct | gcc | ccg | gcg | cct | gcc | gcc | gct | gct | cct | 6264 |
|---|---|---|---|---|---|---|---|---|---|---|---|---|---|---|---|
| Glu | Ile | Ala | Gly | Gly | Ser | Ala | Pro | Ala | Pro | Ala | Ala | Ala | Ala | Pro | |
| 2075 | | | | | 2080 | | | | | 2085 | | | | | |

| gcc | tcg | gct | ggc | gcc | gcg | cct | gcg | gtc | aag | att | gac | tcg | gtc | cac | 6309 |
|---|---|---|---|---|---|---|---|---|---|---|---|---|---|---|---|
| Ala | Ser | Ala | Gly | Ala | Ala | Pro | Ala | Val | Lys | Ile | Asp | Ser | Val | His | |
| 2090 | | | | | 2095 | | | | | 2100 | | | | | |

| ggc | gct | gac | tgt | gat | gat | ctt | tcc | ctg | atg | cac | gcc | aag | gtg | gtt | 6354 |
|---|---|---|---|---|---|---|---|---|---|---|---|---|---|---|---|
| Gly | Ala | Asp | Cys | Asp | Asp | Leu | Ser | Leu | Met | His | Ala | Lys | Val | Val | |
| 2105 | | | | | 2110 | | | | | 2115 | | | | | |

| gac | atc | cgc | cgc | ccg | gac | gag | ctc | atc | ctg | gag | cgc | ccc | gag | aac | 6399 |
|---|---|---|---|---|---|---|---|---|---|---|---|---|---|---|---|
| Asp | Ile | Arg | Arg | Pro | Asp | Glu | Leu | Ile | Leu | Glu | Arg | Pro | Glu | Asn | |
| 2120 | | | | | 2125 | | | | | 2130 | | | | | |

| cgc | ccc | gtt | ctc | gtt | gtc | gat | gac | ggc | agc | gag | ctc | acc | ctc | gcc | 6444 |
|---|---|---|---|---|---|---|---|---|---|---|---|---|---|---|---|
| Arg | Pro | Val | Leu | Val | Val | Asp | Asp | Gly | Ser | Glu | Leu | Thr | Leu | Ala | |
| 2135 | | | | | 2140 | | | | | 2145 | | | | | |

| ctg | gtc | cgc | gtc | ctc | ggc | gcc | tgc | gcc | gtt | gtc | ctg | acc | ttt | gag | 6489 |
|---|---|---|---|---|---|---|---|---|---|---|---|---|---|---|---|
| Leu | Val | Arg | Val | Leu | Gly | Ala | Cys | Ala | Val | Val | Leu | Thr | Phe | Glu | |
| 2150 | | | | | 2155 | | | | | 2160 | | | | | |

| ggt | ctc | cag | ctc | gct | cag | cgc | gct | ggt | gcc | gct | gcc | atc | cgc | cac | 6534 |
|---|---|---|---|---|---|---|---|---|---|---|---|---|---|---|---|
| Gly | Leu | Gln | Leu | Ala | Gln | Arg | Ala | Gly | Ala | Ala | Ala | Ile | Arg | His | |
| 2165 | | | | | 2170 | | | | | 2175 | | | | | |

| gtg | ctc | gcc | aag | gat | ctt | tcc | gcg | gag | agc | gcc | gag | aag | gcc | atc | 6579 |
|---|---|---|---|---|---|---|---|---|---|---|---|---|---|---|---|
| Val | Leu | Ala | Lys | Asp | Leu | Ser | Ala | Glu | Ser | Ala | Glu | Lys | Ala | Ile | |
| 2180 | | | | | 2185 | | | | | 2190 | | | | | |

| aag | gag | gcc | gag | cag | cgc | ttt | ggc | gct | ctc | ggc | ggc | ttc | atc | tcg | 6624 |
|---|---|---|---|---|---|---|---|---|---|---|---|---|---|---|---|
| Lys | Glu | Ala | Glu | Gln | Arg | Phe | Gly | Ala | Leu | Gly | Gly | Phe | Ile | Ser | |
| 2195 | | | | | 2200 | | | | | 2205 | | | | | |

| cag | cag | gcg | gag | cgc | ttc | gag | ccc | gcc | gaa | atc | ctc | ggc | ttc | acg | 6669 |
|---|---|---|---|---|---|---|---|---|---|---|---|---|---|---|---|
| Gln | Gln | Ala | Glu | Arg | Phe | Glu | Pro | Ala | Glu | Ile | Leu | Gly | Phe | Thr | |
| 2210 | | | | | 2215 | | | | | 2220 | | | | | |

| ctc | atg | tgc | gcc | aag | ttc | gcc | aag | gct | tcc | ctc | tgc | acg | gct | gtg | 6714 |
|---|---|---|---|---|---|---|---|---|---|---|---|---|---|---|---|
| Leu | Met | Cys | Ala | Lys | Phe | Ala | Lys | Ala | Ser | Leu | Cys | Thr | Ala | Val | |
| 2225 | | | | | 2230 | | | | | 2235 | | | | | |

| gct | ggc | ggc | cgc | ccg | gcc | ttt | atc | ggt | gtg | gcg | cgc | ctt | gac | ggc | 6759 |
|---|---|---|---|---|---|---|---|---|---|---|---|---|---|---|---|
| Ala | Gly | Gly | Arg | Pro | Ala | Phe | Ile | Gly | Val | Ala | Arg | Leu | Asp | Gly | |
| 2240 | | | | | 2245 | | | | | 2250 | | | | | |

| cgc | ctc | gga | ttc | act | tcg | cag | ggc | act | tct | gac | gcg | ctc | aag | cgt | 6804 |
|---|---|---|---|---|---|---|---|---|---|---|---|---|---|---|---|
| Arg | Leu | Gly | Phe | Thr | Ser | Gln | Gly | Thr | Ser | Asp | Ala | Leu | Lys | Arg | |
| 2255 | | | | | 2260 | | | | | 2265 | | | | | |

| gcc | cag | cgt | ggt | gcc | atc | ttt | ggc | ctc | tgc | aag | acc | atc | ggc | ctc | 6849 |
|---|---|---|---|---|---|---|---|---|---|---|---|---|---|---|---|
| Ala | Gln | Arg | Gly | Ala | Ile | Phe | Gly | Leu | Cys | Lys | Thr | Ile | Gly | Leu | |
| 2270 | | | | | 2275 | | | | | 2280 | | | | | |

-continued

| | | | | | | | | | | | | | | |
|---|---|---|---|---|---|---|---|---|---|---|---|---|---|---|
| gag | tgg | tcc | gag | tct | gac | gtc | ttt | tcc | cgc | ggc | gtg | gac | att | gct | 6894 |
| Glu | Trp | Ser | Glu | Ser | Asp | Val | Phe | Ser | Arg | Gly | Val | Asp | Ile | Ala | |
| | 2285 | | | | 2290 | | | | | 2295 | | | | | |

| cag | ggc | atg | cac | ccc | gag | gat | gcc | gcc | gtg | gcg | att | gtg | cgc | gag | 6939 |
| Gln | Gly | Met | His | Pro | Glu | Asp | Ala | Ala | Val | Ala | Ile | Val | Arg | Glu | |
| 2300 | | | | | 2305 | | | | | 2310 | | | | | |

| atg | gcg | tgc | gct | gac | att | cgc | att | cgc | gag | gtc | ggc | att | ggc | gca | 6984 |
| Met | Ala | Cys | Ala | Asp | Ile | Arg | Ile | Arg | Glu | Val | Gly | Ile | Gly | Ala | |
| 2315 | | | | | 2320 | | | | | 2325 | | | | | |

| aac | cag | cag | cgc | tgc | acg | atc | cgt | gcc | gcc | aag | ctc | gag | acc | ggc | 7029 |
| Asn | Gln | Gln | Arg | Cys | Thr | Ile | Arg | Ala | Ala | Lys | Leu | Glu | Thr | Gly | |
| 2330 | | | | | 2335 | | | | | 2340 | | | | | |

| aac | ccg | cag | cgc | cag | atc | gcc | aag | gac | gac | gtg | ctg | ctc | gtt | tct | 7074 |
| Asn | Pro | Gln | Arg | Gln | Ile | Ala | Lys | Asp | Asp | Val | Leu | Leu | Val | Ser | |
| 2345 | | | | | 2350 | | | | | 2355 | | | | | |

| ggc | ggc | gct | cgc | ggc | atc | acg | cct | ctt | tgc | atc | cgg | gag | atc | acg | 7119 |
| Gly | Gly | Ala | Arg | Gly | Ile | Thr | Pro | Leu | Cys | Ile | Arg | Glu | Ile | Thr | |
| 2360 | | | | | 2365 | | | | | 2370 | | | | | |

| cgc | cag | atc | gcg | ggc | ggc | aag | tac | att | ctg | ctt | ggc | cgc | agc | aag | 7164 |
| Arg | Gln | Ile | Ala | Gly | Gly | Lys | Tyr | Ile | Leu | Leu | Gly | Arg | Ser | Lys | |
| 2375 | | | | | 2380 | | | | | 2385 | | | | | |

| gtc | tct | gcg | agc | gaa | ccg | gca | tgg | tgc | gct | ggc | atc | act | gac | gag | 7209 |
| Val | Ser | Ala | Ser | Glu | Pro | Ala | Trp | Cys | Ala | Gly | Ile | Thr | Asp | Glu | |
| 2390 | | | | | 2395 | | | | | 2400 | | | | | |

| aag | gct | gtg | caa | aag | gct | gct | acc | cag | gag | ctc | aag | cgc | gcc | ttt | 7254 |
| Lys | Ala | Val | Gln | Lys | Ala | Ala | Thr | Gln | Glu | Leu | Lys | Arg | Ala | Phe | |
| 2405 | | | | | 2410 | | | | | 2415 | | | | | |

| agc | gct | ggc | gag | ggc | ccc | aag | ccc | acg | ccc | cgc | gct | gtc | act | aag | 7299 |
| Ser | Ala | Gly | Glu | Gly | Pro | Lys | Pro | Thr | Pro | Arg | Ala | Val | Thr | Lys | |
| 2420 | | | | | 2425 | | | | | 2430 | | | | | |

| ctt | gtg | ggc | tct | gtt | ctt | ggc | gct | cgc | gag | gtg | cgc | agc | tct | att | 7344 |
| Leu | Val | Gly | Ser | Val | Leu | Gly | Ala | Arg | Glu | Val | Arg | Ser | Ser | Ile | |
| 2435 | | | | | 2440 | | | | | 2445 | | | | | |

| gct | gcg | att | gaa | gcg | ctc | ggc | ggc | aag | gcc | atc | tac | tcg | tcg | tgc | 7389 |
| Ala | Ala | Ile | Glu | Ala | Leu | Gly | Gly | Lys | Ala | Ile | Tyr | Ser | Ser | Cys | |
| 2450 | | | | | 2455 | | | | | 2460 | | | | | |

| gac | gtg | aac | tct | gcc | gcc | gac | gtg | gcc | aag | gcc | gtg | cgc | gat | gcc | 7434 |
| Asp | Val | Asn | Ser | Ala | Ala | Asp | Val | Ala | Lys | Ala | Val | Arg | Asp | Ala | |
| 2465 | | | | | 2470 | | | | | 2475 | | | | | |

| gag | tcc | cag | ctc | ggt | gcc | cgc | gtc | tcg | ggc | atc | gtt | cat | gcc | tcg | 7479 |
| Glu | Ser | Gln | Leu | Gly | Ala | Arg | Val | Ser | Gly | Ile | Val | His | Ala | Ser | |
| 2480 | | | | | 2485 | | | | | 2490 | | | | | |

| ggc | gtg | ctc | cgc | gac | cgt | ctc | atc | gag | aag | aag | ctc | ccc | gac | gag | 7524 |
| Gly | Val | Leu | Arg | Asp | Arg | Leu | Ile | Glu | Lys | Lys | Leu | Pro | Asp | Glu | |
| 2495 | | | | | 2500 | | | | | 2505 | | | | | |

| ttc | gac | gcc | gtc | ttt | ggc | acc | aag | gtc | acc | ggt | ctc | gag | aac | ctc | 7569 |
| Phe | Asp | Ala | Val | Phe | Gly | Thr | Lys | Val | Thr | Gly | Leu | Glu | Asn | Leu | |
| 2510 | | | | | 2515 | | | | | 2520 | | | | | |

| ctc | gcc | gcc | gtc | gac | cgc | gcc | aac | ctc | aag | cac | atg | gtc | ctc | ttc | 7614 |
| Leu | Ala | Ala | Val | Asp | Arg | Ala | Asn | Leu | Lys | His | Met | Val | Leu | Phe | |
| 2525 | | | | | 2530 | | | | | 2535 | | | | | |

| agc | tcg | ctc | gcc | ggc | ttc | cac | ggc | aac | gtc | ggc | cag | tct | gac | tac | 7659 |
| Ser | Ser | Leu | Ala | Gly | Phe | His | Gly | Asn | Val | Gly | Gln | Ser | Asp | Tyr | |
| 2540 | | | | | 2545 | | | | | 2550 | | | | | |

| gcc | atg | gcc | aac | gag | gcc | ctt | aac | aag | atg | ggc | ctc | gag | ctc | gcc | 7704 |
| Ala | Met | Ala | Asn | Glu | Ala | Leu | Asn | Lys | Met | Gly | Leu | Glu | Leu | Ala | |
| 2555 | | | | | 2560 | | | | | 2565 | | | | | |

| aag | gac | gtc | tcg | gtc | aag | tcg | atc | tgc | ttc | ggt | ccc | tgg | gac | ggt | 7749 |
| Lys | Asp | Val | Ser | Val | Lys | Ser | Ile | Cys | Phe | Gly | Pro | Trp | Asp | Gly | |
| 2570 | | | | | 2575 | | | | | 2580 | | | | | |

```
ggc atg gtg acg ccg cag ctc aag aag cag ttc cag gag atg ggc      7794
Gly Met Val Thr Pro Gln Leu Lys Lys Gln Phe Gln Glu Met Gly
        2585                2590                2595 gtg cag atc atc ccc cgc gag ggc ggc gct gat acc gtg gcg cgc      7839
Val Gln Ile Ile Pro Arg Glu Gly Gly Ala Asp Thr Val Ala Arg
    2600                2605                2610 atc gtg ctc ggc tcc tcg ccg gct gag atc ctt gtc ggc aac tgg      7884
Ile Val Leu Gly Ser Ser Pro Ala Glu Ile Leu Val Gly Asn Trp
        2615                2620                2625 cgc acc ccg tcc aag aag gtc ggc tcg gac acc atc acc ctg cac      7929
Arg Thr Pro Ser Lys Lys Val Gly Ser Asp Thr Ile Thr Leu His
        2630                2635                2640 cgc aag att tcc gcc aag tcc aac ccc ttc ctc gag gac cac gtc      7974
Arg Lys Ile Ser Ala Lys Ser Asn Pro Phe Leu Glu Asp His Val
        2645                2650                2655 atc cag ggc cgc cgc gtg ctg ccc atg acg ctg gcc att ggc tcg      8019
Ile Gln Gly Arg Arg Val Leu Pro Met Thr Leu Ala Ile Gly Ser
        2660                2665                2670 ctc gcg gag acc tgc ctc ggc ctc ttc ccc ggc tac tcg ctc tgg      8064
Leu Ala Glu Thr Cys Leu Gly Leu Phe Pro Gly Tyr Ser Leu Trp
        2675                2680                2685 gcc att gac gac gcc cag ctc ttc aag ggt gtc act gtc gac ggc      8109
Ala Ile Asp Asp Ala Gln Leu Phe Lys Gly Val Thr Val Asp Gly
        2690                2695                2700 gac gtc aac tgc gag gtg acc ctc acc ccg tcg acg gcg ccc tcg      8154
Asp Val Asn Cys Glu Val Thr Leu Thr Pro Ser Thr Ala Pro Ser
        2705                2710                2715 ggc cgc gtc aac gtc cag gcc acg ctc aag acc ttt tcc agc ggc      8199
Gly Arg Val Asn Val Gln Ala Thr Leu Lys Thr Phe Ser Ser Gly
        2720                2725                2730 aag ctg gtc ccg gcc tac cgc gcc gtc atc gtg ctc tcc aac cag      8244
Lys Leu Val Pro Ala Tyr Arg Ala Val Ile Val Leu Ser Asn Gln
        2735                2740                2745 ggc gcg ccc ccg gcc aac gcc acc atg cag ccg ccc tcg ctc gat      8289
Gly Ala Pro Pro Ala Asn Ala Thr Met Gln Pro Pro Ser Leu Asp
        2750                2755                2760 gcc gat ccg gcg ctc cag ggc tcc gtc tac gac ggc aag acc ctc      8334
Ala Asp Pro Ala Leu Gln Gly Ser Val Tyr Asp Gly Lys Thr Leu
        2765                2770                2775 ttc cac ggc ccg gcc ttc cgc ggc atc gat gac gtg ctc tcg tgc      8379
Phe His Gly Pro Ala Phe Arg Gly Ile Asp Asp Val Leu Ser Cys
        2780                2785                2790 acc aag agc cag ctt gtg gcc aag tgc agc gct gtc ccc ggc tcc      8424
Thr Lys Ser Gln Leu Val Ala Lys Cys Ser Ala Val Pro Gly Ser
        2795                2800                2805 gac gcc gct cgc ggc gag ttt gcc acg gac act gac gcc cat gac      8469
Asp Ala Ala Arg Gly Glu Phe Ala Thr Asp Thr Asp Ala His Asp
        2810                2815                2820 ccc ttc gtg aac gac ctg gcc ttt cag gcc atg ctc gtc tgg gtg      8514
Pro Phe Val Asn Asp Leu Ala Phe Gln Ala Met Leu Val Trp Val
        2825                2830                2835 cgc cgc acg ctc ggc cag gct gcg ctc ccc aac tcg atc cag cgc      8559
Arg Arg Thr Leu Gly Gln Ala Ala Leu Pro Asn Ser Ile Gln Arg
        2840                2845                2850 atc gtc cag cac cgc ccg gtc ccg cag gac aag ccc ttc tac att      8604
Ile Val Gln His Arg Pro Val Pro Gln Asp Lys Pro Phe Tyr Ile
        2855                2860                2865 acc ctc cgc tcc aac cag tcg ggc ggt cac tcc cag cac aag cac      8649
Thr Leu Arg Ser Asn Gln Ser Gly Gly His Ser Gln His Lys His
```

```
gcc ctt cag ttc cac aac gag cag ggc gat ctc ttc att gat gtc    8694
Ala Leu Gln Phe His Asn Glu Gln Gly Asp Leu Phe Ile Asp Val
    2885                2890                2895 cag gct tcg gtc atc gcc acg gac agc ctt gcc ttc taa             8733
Gln Ala Ser Val Ile Ala Thr Asp Ser Leu Ala Phe
2900                2905                2910

<210> SEQ ID NO 5
<211> LENGTH: 714
<212> TYPE: DNA
<213> ORGANISM: Nostoc sp. PCC7120
<220> FEATURE:
<221> NAME/KEY: CDS
<222> LOCATION: (1)..(714)

<400> SEQUENCE: 5 atg ctg caa cat acc tgg ctg ccg aaa ccg cct aat ctg acc ctg ctg    48
Met Leu Gln His Thr Trp Leu Pro Lys Pro Pro Asn Leu Thr Leu Leu
1               5                   10                  15 agt gat gaa gtt cat ctg tgg cgt att ccg ctg gat cag ccg gaa agc    96
Ser Asp Glu Val His Leu Trp Arg Ile Pro Leu Asp Gln Pro Glu Ser
            20                  25                  30 cag ctg caa gac ctg gca gca acc ctg agc agt gat gaa ctg gca cgt    144
Gln Leu Gln Asp Leu Ala Ala Thr Leu Ser Ser Asp Glu Leu Ala Arg
        35                  40                  45 gca aat cgt ttc tat ttt ccg gaa cat cgt cgt cgt ttt acc gca ggt    192
Ala Asn Arg Phe Tyr Phe Pro Glu His Arg Arg Arg Phe Thr Ala Gly
    50                  55                  60 cgt ggt att ctg cgt agc att ctg ggt ggt tat ctg ggt gtt gaa ccg    240
Arg Gly Ile Leu Arg Ser Ile Leu Gly Gly Tyr Leu Gly Val Glu Pro
65                  70                  75                  80 ggt cag gtt aaa ttt gat tat gaa agc cgt ggt aaa ccg att ctg ggc    288
Gly Gln Val Lys Phe Asp Tyr Glu Ser Arg Gly Lys Pro Ile Leu Gly
                85                  90                  95 gat cgt ttt gca gaa agc ggt ctg ctg ttt aat ctg agc cat agc cag    336
Asp Arg Phe Ala Glu Ser Gly Leu Leu Phe Asn Leu Ser His Ser Gln
            100                 105                 110 aat ctg gca ctg tgt gca gtg aat tat acc cgt cag att ggt atc gat    384
Asn Leu Ala Leu Cys Ala Val Asn Tyr Thr Arg Gln Ile Gly Ile Asp
        115                 120                 125 ctg gaa tat ctg cgt ccg acc agt gat ctg gaa agc ctg gcc aaa cgt    432
Leu Glu Tyr Leu Arg Pro Thr Ser Asp Leu Glu Ser Leu Ala Lys Arg
    130                 135                 140 ttt ttt ctg cct cgt gaa tat gaa ctg ctg cgt agc ctg ccg gat gaa    480
Phe Phe Leu Pro Arg Glu Tyr Glu Leu Leu Arg Ser Leu Pro Asp Glu
145                 150                 155                 160 cag aaa cag aaa atc ttt ttt cgt tat tgg acc tgc aaa gaa gcc tat    528
Gln Lys Gln Lys Ile Phe Phe Arg Tyr Trp Thr Cys Lys Glu Ala Tyr
                165                 170                 175 ctg aaa gca acc ggt gat ggt att gca aaa ctg gaa gaa att gaa att    576
Leu Lys Ala Thr Gly Asp Gly Ile Ala Lys Leu Glu Glu Ile Glu Ile
            180                 185                 190 gca ctg acc ccg acc gaa ccg gca aaa ctg caa acc gca ccg gca tgg    624
Ala Leu Thr Pro Thr Glu Pro Ala Lys Leu Gln Thr Ala Pro Ala Trp
        195                 200                 205 tca ctg ctg gaa ctg gtt ccg gat gat aat tgt gtt gca gcc gtt gca    672
Ser Leu Leu Glu Leu Val Pro Asp Asp Asn Cys Val Ala Ala Val Ala
    210                 215                 220 gtt gca ggt ttt ggt tgg cag ccg aaa ttt tgg cat tat taa            714
Val Ala Gly Phe Gly Trp Gln Pro Lys Phe Trp His Tyr
```

<210> SEQ ID NO 6
<211> LENGTH: 814
<212> TYPE: PRT
<213> ORGANISM: Escherichia coli

<400> SEQUENCE: 6

Met Met Ile Leu Ser Ile Leu Ala Thr Val Leu Leu Gly Ala Leu
1               5                   10                  15

Phe Tyr His Arg Val Ser Leu Phe Ile Ser Ser Leu Ile Leu Leu Ala
            20                  25                  30

Trp Thr Ala Ala Leu Gly Val Ala Gly Leu Trp Ser Ala Trp Val Leu
        35                  40                  45

Val Pro Leu Ala Ile Ile Leu Val Pro Phe Asn Phe Ala Pro Met Arg
    50                  55                  60

Lys Ser Met Ile Ser Ala Pro Val Phe Arg Gly Phe Arg Lys Val Met
65                  70                  75                  80

Pro Pro Met Ser Arg Thr Glu Lys Glu Ala Ile Asn Ala Gly Thr Thr
                85                  90                  95

Trp Trp Glu Gly Asp Leu Phe Gln Gly Lys Pro Asp Trp Lys Lys Leu
            100                 105                 110

His Asn Tyr Pro Gln Pro Arg Leu Thr Ala Glu Glu Ala Phe Leu
        115                 120                 125

Asp Gly Pro Val Glu Glu Ala Cys Arg Met Ala Asn Asp Phe Gln Ile
    130                 135                 140

Thr His Glu Leu Ala Asp Leu Pro Pro Glu Leu Trp Ala Tyr Leu Lys
145                 150                 155                 160

Glu His Arg Phe Phe Ala Met Ile Ile Lys Lys Glu Tyr Gly Gly Leu
                165                 170                 175

Glu Phe Ser Ala Tyr Ala Gln Ser Arg Val Leu Gln Lys Leu Ser Gly
            180                 185                 190

Val Ser Gly Ile Leu Ala Ile Thr Val Gly Val Pro Asn Ser Leu Gly
        195                 200                 205

Pro Gly Glu Leu Leu Gln His Tyr Gly Thr Asp Glu Gln Lys Asp His
    210                 215                 220

Tyr Leu Pro Arg Leu Ala Arg Gly Gln Glu Ile Pro Cys Phe Ala Leu
225                 230                 235                 240

Thr Ser Pro Glu Ala Gly Ser Asp Ala Gly Ala Ile Pro Asp Thr Gly
                245                 250                 255

Ile Val Cys Met Gly Glu Trp Gln Gly Gln Val Leu Gly Met Arg
            260                 265                 270

Leu Thr Trp Asn Lys Arg Tyr Ile Thr Leu Ala Pro Ile Ala Thr Val
        275                 280                 285

Leu Gly Leu Ala Phe Lys Leu Ser Asp Pro Glu Lys Leu Leu Gly Gly
    290                 295                 300

Ala Glu Asp Leu Gly Ile Thr Cys Ala Leu Ile Pro Thr Thr Thr Pro
305                 310                 315                 320

Gly Val Glu Ile Gly Arg Arg His Phe Pro Leu Asn Val Pro Phe Gln
                325                 330                 335

Asn Gly Pro Thr Arg Gly Lys Asp Val Phe Val Pro Ile Asp Tyr Ile
            340                 345                 350

Ile Gly Gly Pro Lys Met Ala Gly Gln Gly Trp Arg Met Leu Val Glu
        355                 360                 365

```
Cys Leu Ser Val Gly Arg Gly Ile Thr Leu Pro Ser Asn Ser Thr Gly
370                 375                 380

Gly Val Lys Ser Val Ala Leu Ala Thr Gly Ala Tyr Ala His Ile Arg
385                 390                 395                 400

Arg Gln Phe Lys Ile Ser Ile Gly Lys Met Glu Gly Ile Glu Glu Pro
                405                 410                 415

Leu Ala Arg Ile Ala Gly Asn Ala Tyr Val Met Asp Ala Ala Ala Ser
            420                 425                 430

Leu Ile Thr Tyr Gly Ile Met Leu Gly Glu Lys Pro Ala Val Leu Ser
        435                 440                 445

Ala Ile Val Lys Tyr His Cys Thr His Arg Gly Gln Gln Ser Ile Ile
450                 455                 460

Asp Ala Met Asp Ile Thr Gly Gly Lys Gly Ile Met Leu Gly Gln Ser
465                 470                 475                 480

Asn Phe Leu Ala Arg Ala Tyr Gln Gly Ala Pro Ile Ala Ile Thr Val
                485                 490                 495

Glu Gly Ala Asn Ile Leu Thr Arg Ser Met Met Ile Phe Gly Gln Gly
            500                 505                 510

Ala Ile Arg Cys His Pro Tyr Val Leu Glu Glu Met Glu Ala Ala Lys
        515                 520                 525

Asn Asn Asp Val Asn Ala Phe Asp Lys Leu Leu Phe Lys His Ile Gly
530                 535                 540

His Val Gly Ser Asn Lys Val Arg Ser Phe Trp Leu Gly Leu Thr Arg
545                 550                 555                 560

Gly Leu Thr Ser Ser Thr Pro Thr Gly Asp Ala Thr Lys Arg Tyr Tyr
                565                 570                 575

Gln His Leu Asn Arg Leu Ser Ala Asn Leu Ala Leu Leu Ser Asp Val
            580                 585                 590

Ser Met Ala Val Leu Gly Gly Ser Leu Lys Arg Arg Glu Arg Ile Ser
        595                 600                 605

Ala Arg Leu Gly Asp Ile Leu Ser Gln Leu Tyr Leu Ala Ser Ala Val
610                 615                 620

Leu Lys Arg Tyr Asp Asp Glu Gly Arg Asn Glu Ala Asp Leu Pro Leu
625                 630                 635                 640

Val His Trp Gly Val Gln Asp Ala Leu Tyr Gln Ala Glu Gln Ala Met
                645                 650                 655

Asp Asp Leu Leu Gln Asn Phe Pro Asn Arg Val Val Ala Gly Leu Leu
            660                 665                 670

Asn Val Val Ile Phe Pro Thr Gly Arg His Tyr Leu Ala Pro Ser Asp
        675                 680                 685

Lys Leu Asp His Lys Val Ala Lys Ile Leu Gln Val Pro Asn Ala Thr
690                 695                 700

Arg Ser Arg Ile Gly Arg Gly Gln Tyr Leu Thr Pro Ser Glu His Asn
705                 710                 715                 720

Pro Val Gly Leu Leu Glu Glu Ala Leu Val Asp Val Ile Ala Ala Asp
                725                 730                 735

Pro Ile His Gln Arg Ile Cys Lys Glu Leu Gly Lys Asn Leu Pro Phe
            740                 745                 750

Thr Arg Leu Asp Glu Leu Ala His Asn Ala Leu Val Lys Gly Leu Ile
        755                 760                 765

Asp Lys Asp Glu Ala Ala Ile Leu Val Lys Ala Glu Glu Ser Arg Leu
770                 775                 780

Arg Ser Ile Asn Val Asp Asp Phe Asp Pro Glu Glu Leu Ala Thr Lys
```

```
                  785                 790                 795                 800
Pro Val Lys Leu Pro Glu Lys Val Arg Lys Val Glu Ala Ala
                805                 810
```

<210> SEQ ID NO 7
<211> LENGTH: 40
<212> TYPE: DNA
<213> ORGANISM: Artificial Sequence
<220> FEATURE:
<223> OTHER INFORMATION: Synthetic DNA

<400> SEQUENCE: 7
aaaaaacata tggccactcg cgtgaagacc aacaagaaac                              40

<210> SEQ ID NO 8
<211> LENGTH: 44
<212> TYPE: DNA
<213> ORGANISM: Artificial Sequence
<220> FEATURE:
<223> OTHER INFORMATION: Synthetic DNA

<400> SEQUENCE: 8
aaacaattgt tagagggcgt tggtgggctc gtagacgaac tcag                        44

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA

<400> SEQUENCE: 9
aaaaaacata tggcctctcg caagaatgtg agcgctgc                              38

<210> SEQ ID NO 10
<211> LENGTH: 39
<212> TYPE: DNA
<213> ORGANISM: Artificial Sequence
<220> FEATURE:
<223> OTHER INFORMATION: Synthetic DNA

<400> SEQUENCE: 10
aaagaattct tacaggcgct cagtgggcac gtagatgtc                             39

<210> SEQ ID NO 11
<211> LENGTH: 41
<212> TYPE: DNA
<213> ORGANISM: Artificial Sequence
<220> FEATURE:
<223> OTHER INFORMATION: Synthetic DNA

<400> SEQUENCE: 11
gccttcatgg agacttatgg tgtatccgcc cccatgtaca c                          41

<210> SEQ ID NO 12
<211> LENGTH: 28
<212> TYPE: DNA
<213> ORGANISM: Artificial Sequence
<220> FEATURE:
<223> OTHER INFORMATION: Synthetic DNA

<400> SEQUENCE: 12
acaccataag tctccatgaa ggcacggc                                         28

<210> SEQ ID NO 13

<211> LENGTH: 37
<212> TYPE: DNA
<213> ORGANISM: Artificial Sequence
<220> FEATURE:
<223> OTHER INFORMATION: Synthetic DNA

<400> SEQUENCE: 13
gtctctgtac gcatgccagt cctcgcgggc ctggttg                    37

<210> SEQ ID NO 14
<211> LENGTH: 39
<212> TYPE: DNA
<213> ORGANISM: Artificial Sequence
<220> FEATURE:
<223> OTHER INFORMATION: Synthetic DNA

<400> SEQUENCE: 14
gaggactggc atgcgtacag agacttgccc cactgtgtc                  39

<210> SEQ ID NO 15
<211> LENGTH: 29
<212> TYPE: DNA
<213> ORGANISM: Artificial Sequence
<220> FEATURE:
<223> OTHER INFORMATION: Synthetic DNA

<400> SEQUENCE: 15
ctctcttccg ggcgctatca tgccatacc                             29

<210> SEQ ID NO 16
<211> LENGTH: 29
<212> TYPE: DNA
<213> ORGANISM: Artificial Sequence
<220> FEATURE:
<223> OTHER INFORMATION: Synthetic DNA

<400> SEQUENCE: 16
gcacagcacc atgttggcca ttgtagatg                             29

<210> SEQ ID NO 17
<211> LENGTH: 24
<212> TYPE: DNA
<213> ORGANISM: Artificial Sequence
<220> FEATURE:
<223> OTHER INFORMATION: Synthetic DNA

<400> SEQUENCE: 17
aaagggctcc gggaagcaag ttgc                                  24

<210> SEQ ID NO 18
<211> LENGTH: 51
<212> TYPE: DNA
<213> ORGANISM: Artificial Sequence
<220> FEATURE:
<223> OTHER INFORMATION: Synthetic DNA

<400> SEQUENCE: 18
gcaacttgct tcccggagcc cttttggatt ctctccggat tctccacttt c    51

<210> SEQ ID NO 19
<211> LENGTH: 51
<212> TYPE: DNA
<213> ORGANISM: Artificial Sequence
<220> FEATURE:
<223> OTHER INFORMATION: Synthetic DNA

<400> SEQUENCE: 19
gcaacttgct tcccggagcc ctttaatatt ctctccggat tctccacttt c    51

<210> SEQ ID NO 20
<211> LENGTH: 51
<212> TYPE: DNA
<213> ORGANISM: Artificial Sequence
<220> FEATURE:
<223> OTHER INFORMATION: Synthetic DNA

<400> SEQUENCE: 20
gcaacttgct tcccggagcc ctttgggatt ctctccggat tctccacttt c    51

<210> SEQ ID NO 21
<211> LENGTH: 51
<212> TYPE: DNA
<213> ORGANISM: Artificial Sequence
<220> FEATURE:
<223> OTHER INFORMATION: Synthetic DNA

<400> SEQUENCE: 21
gcaacttgct tcccggagcc ctttgacatt ctctccggat tctccacttt c    51

<210> SEQ ID NO 22
<211> LENGTH: 51
<212> TYPE: DNA
<213> ORGANISM: Artificial Sequence
<220> FEATURE:
<223> OTHER INFORMATION: Synthetic DNA

<400> SEQUENCE: 22
gcaacttgct tcccggagcc ctttgctatt ctctccggat tctccacttt c    51

<210> SEQ ID NO 23
<211> LENGTH: 48
<212> TYPE: DNA
<213> ORGANISM: Artificial Sequence
<220> FEATURE:
<223> OTHER INFORMATION: Synthetic DNA

<400> SEQUENCE: 23
gatatacata tggcctctcg caagagtgtg agcgctgctc acgaaatg    48

<210> SEQ ID NO 24
<211> LENGTH: 29
<212> TYPE: DNA
<213> ORGANISM: Artificial Sequence
<220> FEATURE:
<223> OTHER INFORMATION: Synthetic DNA

<400> SEQUENCE: 24
ctctcttccg ggcgctatca tgccatacc    29

<210> SEQ ID NO 25
<211> LENGTH: 24
<212> TYPE: DNA
<213> ORGANISM: Artificial Sequence
<220> FEATURE:
<223> OTHER INFORMATION: Synthetic DNA

<400> SEQUENCE: 25
ttgaggtgct cggctcgctt gttg    24

<210> SEQ ID NO 26
<211> LENGTH: 37
<212> TYPE: DNA

```
<213> ORGANISM: Artificial Sequence
<220> FEATURE:
<223> OTHER INFORMATION: Synthetic DNA

<400> SEQUENCE: 26
cgagccgagc acctcaaagc agagcgtagc aaatttg                          37

<210> SEQ ID NO 27
<211> LENGTH: 2006
<212> TYPE: PRT
<213> ORGANISM: Photobacterium profundum

<400> SEQUENCE: 27
```

Met His Cys Pro Val Asn Tyr Ala Pro Asn Thr Ala Val Thr Phe Ser
1               5                   10                  15

Pro Ala Ser Arg Val Arg Arg Thr Ser Glu Cys Thr Glu Ile Thr Gln
            20                  25                  30

Cys Ile Val Ser Glu Tyr His Thr Glu His Tyr Thr Arg Arg Ala Ser
        35                  40                  45

Val Ser Ser Gln His Ser Thr Ala Ser Gln Ser Asn Lys Ile Ala Ile
    50                  55                  60

Val Gly Leu Ala Asn Gln Tyr Pro Asp Ala Asp Thr Pro Lys Asp Phe
65                  70                  75                  80

Trp Gln Asn Leu Leu Ala Lys Lys Asp Ser Arg Thr Thr Leu Ser Pro
                85                  90                  95

Asp Lys Leu Gly Ala Asn Pro Asp Ala Tyr Gln Gly Ile Gln Gly Glu
            100                 105                 110

Ser Asp Arg Phe Tyr Cys Asp Lys Gly Tyr Ile Gln Asn Phe Ser
            115                 120                 125

Phe Asp Ser Asn Gly Tyr Arg Leu Pro Ala Glu Thr Phe Glu Gly Leu
    130                 135                 140

Asp Glu Ser Phe Leu Trp Ala Leu Asp Thr Ser Arg Lys Ala Leu Ala
145                 150                 155                 160

Asp Ala Gly Ile Pro Leu Asp Ala Val Leu Glu Arg Thr Gly Val
                165                 170                 175

Ile Met Gly Ala Leu Ser Phe Pro Thr Lys Arg Ser Asn Asp Leu Phe
            180                 185                 190

Leu Pro Ile Tyr His Ser Ala Val Glu Lys Ala Leu Gln Thr Lys Leu
        195                 200                 205

Gly Asn Glu His Phe Thr Leu Thr Pro Ser Asn Ala Asn Ile Thr Ser
    210                 215                 220

Leu Asn Pro Ala Asn Gly Ser Ala Ala His Asn Ala Ser Arg Leu Val
225                 230                 235                 240

Ala Asp Ala Leu Gly Leu Gly Ser Val Gln Leu Ser Leu Asp Ala Ala
                245                 250                 255

Cys Ala Ser Ser Val Tyr Ser Leu Lys Leu Ala Cys Asp Tyr Leu Asn
            260                 265                 270

Thr Gly Lys Ala Asp Met Met Leu Ala Gly Ala Val Ser Gly Ala Asp
        275                 280                 285

Pro Phe Phe Ile Asn Met Gly Phe Ser Ile Phe His Ala Tyr Pro Asp
    290                 295                 300

His Gly Val Ser Val Pro Phe Asp Thr Asn Ser Lys Gly Leu Phe Ala
305                 310                 315                 320

Gly Glu Gly Ala Gly Val Leu Ile Leu Lys Arg Leu Glu Asp Ala Glu
                325                 330                 335

-continued

Arg Asp Gly Asp Asn Ile Tyr Ala Val Val Ser Gly Ile Gly Leu Ser
            340                 345                 350

Asn Asp Gly Arg Gly Gln Phe Val Leu Ser Pro Asn Ser Lys Gly Gln
        355                 360                 365

Val Gln Ala Phe Glu Arg Ala Tyr Glu Ala Thr Asp Leu Ser Pro Glu
    370                 375                 380

Ser Ile Glu Val Ile Glu Cys His Ala Thr Gly Thr Pro Leu Gly Asp
385                 390                 395                 400

Lys Val Glu Met Thr Ser Met Glu Arg Phe Phe Ala Asp Lys Leu Asn
                405                 410                 415

Gly Ser Gln Ala Pro Leu Ile Gly Ser Ala Lys Ser Asn Leu Gly His
            420                 425                 430

Leu Leu Thr Ala Ala Gly Met Pro Gly Ile Met Lys Met Ile Phe Ala
        435                 440                 445

Met Lys Glu Gly Val Leu Pro Pro Ser Ile Asn Leu Ser Thr Pro Leu
    450                 455                 460

Ser Ser Pro Glu Gly Leu Phe Gly Ser His Thr Leu Pro Thr Gln Val
465                 470                 475                 480

Gln Ala Trp Pro Asp Lys Ala Gly Asn Thr Glu Arg Cys Ala Gly Val
                485                 490                 495

Ser Val Phe Gly Phe Gly Gly Cys Asn Ala His Leu Leu Glu Ala
            500                 505                 510

His Ser Ala Asn Ser Ala Arg Asn Ser Pro Ala Ala Asn Ser Pro Ala
        515                 520                 525

Lys Pro Ala Val Ser Ala Pro Leu Lys Val Thr Gly Leu Ala Ser His
530                 535                 540

Phe Gly Ser Leu Lys Thr Ile Asn Ala Leu His Asn Ala Ile Thr Thr
545                 550                 555                 560

Gly Ala Asp Ala Phe Val Ala Leu Pro Lys Lys Arg Trp Lys Gly Leu
                565                 570                 575

Asp Gln His Pro Glu Leu Leu Ser Gln Phe Gly Leu Asp Ala Ile Pro
            580                 585                 590

His Gly Ala Tyr Ile Asp Gln Phe Glu Leu Asp Phe Leu Arg Phe Lys
        595                 600                 605

Val Pro Pro Asn Glu Asp Asp Arg Leu Ile Ser Gln Gln Leu Leu Leu
    610                 615                 620

Met Lys Val Ala Asp Glu Ala Ile Arg Asp Ala Lys Leu Glu Val Gly
625                 630                 635                 640

Gln Lys Val Ala Val Leu Val Ala Met Glu Thr Glu Leu Glu Met His
                645                 650                 655

Gln Phe Arg Gly Arg Val Asn Leu His Thr Gln Leu Ala Asp Ser Leu
            660                 665                 670

Glu Asn Met Gly Val Gln Leu Thr Asp Ser Glu Tyr Gln Ala Leu Glu
        675                 680                 685

Ala Ile Ala Met Asp Ser Val Leu Asp Ala Ala Lys Leu Asn Gln Tyr
    690                 695                 700

Thr Ser Phe Ile Gly Asn Ile Met Ala Ser Arg Ile Ala Ser Leu Trp
705                 710                 715                 720

Asp Phe Asn Gly Pro Ala Phe Thr Ile Ser Ala Ala Glu Gln Ser Val
                725                 730                 735

Ala Arg Cys Ile Asp Val Ala Gln Asn Leu Met Ser Gln Glu Ser Leu
            740                 745                 750

Asp Ala Val Val Ile Ala Ala Val Asp Leu Ser Gly Ser Val Glu Gln

```
                755                 760                 765
Ile Ile Leu Lys Asn Ser Val Thr Pro Val Ala Leu His Pro Gln Asp
770                 775                 780

Ser Gly Trp Asn Val Gly Glu Gly Ala Gly Ala Ile Val Leu Val Asp
785                 790                 795                 800

Thr Asp Asn Ala Ser Thr Lys Asn Ser Tyr Gly Glu Ile Thr Ala Leu
                805                 810                 815

Asp Phe Gly Ser Val Ala Gln Ser Asn Ile Thr Ser Asp Arg Leu Leu
                820                 825                 830

Thr Thr Ala Gly Ile Thr Ala Asn Asn Val Ser Leu Leu Glu Leu Asn
                835                 840                 845

Gln Ala Pro Glu Ser Val Glu Thr Val Gln Phe Pro Leu Pro Ser Ala
850                 855                 860

Thr His Ile Gln Ala Asn Gln Arg Leu Gly His Cys Tyr Ala Ala Ser
865                 870                 875                 880

Gly Met Ala Ser Ile Leu His Gly Leu Ser Leu Asn Ala Ile Pro
                885                 890                 895

Lys Gln Thr Thr Ile Pro Ser Leu Asn Thr Ser Val Thr Ala Ala Val
                900                 905                 910

Thr Lys Ala Ala Ile Val Ala Asn Val Ser Glu Asn Gln Cys Ser Gln
                915                 920                 925

Leu Leu Leu Thr Gln Thr Ser Thr Glu Thr Gln Ser Leu Thr Ala Arg
930                 935                 940

Leu Asn Ser Glu Leu Ala Asn Asp Ser Lys Arg Gln Leu Ile Lys Gln
945                 950                 955                 960

Val Thr Leu Gly Gly Arg Asp Ile Tyr Gln His Ile Val Thr Ala Glu
                965                 970                 975

Leu Ser Asp Ile Gln His Ile Gln Gln Lys Val Ala Asn Thr Lys Pro
                980                 985                 990

Leu Val Gln Lys Gln Asn Ile Lys  Gln Pro Arg Ile Gln  Ala Ile Ala
                995                 1000                1005

Lys Pro  Val Ala Gln Pro  Gln Ser Ile Ala Gln Pro  Thr Ala Ile
        1010                1015                1020

Pro Ser  Val Ser Pro Ile  Leu Thr Thr Pro Arg Gln  Thr Pro Ile
        1025                1030                1035

Thr Gly  Ile Gln Ser Asn Met  Thr Asn Val Leu Ser  Ala Lys Asn
        1040                1045                1050

Lys His  Asp Leu Thr Ala Phe  Gln Ser Ser Ala Phe  Val Glu Asn
        1055                1060                1065

Gln Gln  Leu Ala Gln Gln Val  His Gln Ala Phe Leu  Gln Asn Arg
        1070                1075                1080

Glu Gln  Gly Leu Lys Met Ala  Asp Ala Leu Leu Lys  Ala Gln Leu
        1085                1090                1095

Asn Glu  Val Thr Ala Gln Met  Asn Ala Ala Thr Gly  Gln Val Phe
        1100                1105                1110

Asp His  Gln Leu Ala Pro Ser  Pro Ala Leu Thr Glu  Ala Ser Thr
        1115                1120                1125

Ser Val  Pro Val Asn Val Ala  Ala Thr Pro Ala Ile  Val Asn Pro
        1130                1135                1140

Ile Arg  Lys Pro Cys Ile Trp  Asp Tyr Glu Asp Leu  Val Glu Tyr
        1145                1150                1155

Ala Glu  Gly Asp Ile Ala Asn  Val Phe Gly Pro Asp  Tyr Ala Val
        1160                1165                1170
```

-continued

```
Ile Asp Asn Tyr Ser Arg Arg Val Arg Leu Pro Thr Thr Asp Tyr
1175                1180                1185

Leu Leu Val Ser Arg Val Thr Lys Leu Asp Ala Thr Met Leu Glu
1190                1195                1200

Tyr Lys Pro Ser Thr Met Thr Thr Glu Tyr Asp Ile Pro Val Asp
1205                1210                1215

Ala Pro Tyr Leu Val Asp Gly Gln Ile Pro Trp Ala Val Ala Val
1220                1225                1230

Glu Ser Gly Gln Cys Asp Leu Met Leu Ile Ser Tyr Leu Gly Ile
1235                1240                1245

Asp Phe Glu Asn Lys Gly Glu Arg Val Tyr Arg Leu Leu Asp Cys
1250                1255                1260

Thr Leu Thr Phe Leu Gly Asp Leu Pro Arg Gly Gly Asp Thr Leu
1265                1270                1275

Arg Tyr Asp Ile Ser Ile Asn Asn Phe Ala Arg Asn Gly Asp Thr
1280                1285                1290

Leu Leu Phe Phe Phe Ser Tyr Glu Cys Phe Val Gly Asp Lys Met
1295                1300                1305

Val Leu Lys Met Asp Asn Gly Cys Ala Gly Phe Phe Thr Asp Glu
1310                1315                1320

Glu Leu Ser Asp Gly Lys Gly Val Ile Arg Thr Glu Asp Glu Ile
1325                1330                1335

Lys Ser Arg Asn Leu Ala Val Lys Gln Arg Phe Asn Pro Leu Leu
1340                1345                1350

His Cys Gln Lys Thr Gln Phe Asp Tyr Gln Thr Leu His Asn Leu
1355                1360                1365

Leu Asp Ala Asn Ile Ala Gly Cys Phe Gly Glu Ser His Ile Ser
1370                1375                1380

Asp Arg His Gln Pro Ser Leu Cys Phe Ser Ser Asp Lys Phe Met
1385                1390                1395

Met Ile Glu Gln Ile Ser His Val Asp Pro Gln Gly Gly Thr Trp
1400                1405                1410

Gly Leu Gly Leu Ile Glu Gly His Lys Gln Leu Glu Ala Asp His
1415                1420                1425

Trp Tyr Phe Pro Cys His Phe Lys Asp Asp Ser Val Met Ala Gly
1430                1435                1440

Ser Leu Met Ala Glu Gly Cys Gly Gln Leu Leu Gln Phe Phe Met
1445                1450                1455

Met Tyr Leu Gly Met His Thr Gln Val Glu Asn Gly Arg Phe Gln
1460                1465                1470

Pro Leu Glu Asn Ala Pro Gln Gln Val Arg Cys Arg Gly Gln Val
1475                1480                1485

Leu Pro Gln Ser Ala Val Leu Thr Tyr Arg Met Glu Val Thr Glu
1490                1495                1500

Ile Gly Leu Ser Pro Arg Pro Tyr Ala Lys Ala Asn Ile Asp Ile
1505                1510                1515

Leu Leu Asp Gly Lys Val Val Val Asp Phe Gln Asn Leu Gly Val
1520                1525                1530

Met Ile Lys Glu Glu Ser Glu Cys Thr Arg Tyr Leu Gly Ser Ser
1535                1540                1545

Asp Phe Asp Ser Ala Ser Leu Ala Ser Ser Tyr Val Ala Glu
1550                1555                1560
```

```
Ser Ala Pro Ala Gln Ala Asp Val Ile Thr Pro Val Glu Ala Pro
        1565                1570                1575

Ile Ser Gln Gln Ala Ser Ala Asn Ala Pro Leu Met Ala Gln Ile
1580                1585                1590

Pro Asp Leu Asn Thr Ala Pro Asn Lys Gly Val Ile Pro Leu Gln
1595                1600                1605

His Ile Glu Ala Pro Ile Val Pro Asp Tyr Gln Asn Arg Thr Pro
1610                1615                1620

Asp Thr Val Pro Phe Thr Pro Tyr His Met Phe Glu Phe Ala Thr
1625                1630                1635

Gly Asp Ile Glu Lys Cys Phe Gly Pro Asp Phe Ser Ile Tyr Arg
1640                1645                1650

Gly Met Ile Pro Pro Arg Thr Pro Cys Gly Asp Leu Gln Leu Thr
1655                1660                1665

Thr Arg Val Ile Glu Val Asn Gly Thr Arg Gly Asp Phe Lys Thr
1670                1675                1680

Pro Ser Ser Cys Ile Ala Glu Tyr Glu Val Pro Glu Asn Ala Trp
1685                1690                1695

Tyr Phe Asp Glu Asn Ser His Ser Ser Leu Met Pro Tyr Ser Val
1700                1705                1710

Leu Met Glu Ile Ser Leu Gln Pro Asn Gly Phe Ile Ser Gly Tyr
1715                1720                1725

Met Gly Thr Thr Leu Gly Phe Pro Gly Leu Glu Leu Phe Phe Arg
1730                1735                1740

Asn Leu Asp Gly Ser Gly Lys Met Leu Arg Asn Val Asp Leu Arg
1745                1750                1755

Gly Lys Thr Ile Val Asn Asp Ser Arg Leu Leu Ser Thr Val Met
1760                1765                1770

Met Gly Thr Asn Ile Val Gln Ser Phe Ser Phe Glu Leu Ser Thr
1775                1780                1785

Asp Gly Val Pro Phe Tyr Glu Gly Thr Ala Val Phe Gly Tyr Phe
1790                1795                1800

Lys Gly Ala Ala Leu Lys Asp Gln Leu Gly Leu Asp Asn Gly Gln
1805                1810                1815

Val Thr Tyr Pro Trp His Val Asn Asn Asn Arg Thr Pro Asp Val
1820                1825                1830

Ser Ile Asn Leu Leu Asp Lys Glu Ser Arg Tyr Phe Asn Ala Pro
1835                1840                1845

Leu Ser Ala Thr Gly Glu Ala Gln Pro His Tyr Gln Leu Ala Gly
1850                1855                1860

Gly Arg Leu Asn Phe Ile Asp Lys Val Asp Ile Thr Ser Asp Gly
1865                1870                1875

Gly Lys Ala Gly Leu Gly Tyr Leu Tyr Ala Glu Arg Thr Ile Asp
1880                1885                1890

Pro Ser Asp Trp Phe Phe Gln Phe His Phe His Gln Asp Pro Val
1895                1900                1905

Met Pro Gly Ser Leu Gly Val Glu Ala Ile Ile Glu Leu Met Gln
1910                1915                1920

Thr Tyr Ala Leu Asn Lys Asp Leu Gly Ala Gly Phe Arg Ser Pro
1925                1930                1935

Lys Phe Gly Gln Ile Gln Ser Glu Val Lys Trp Lys Tyr Arg Gly
1940                1945                1950

Gln Ile Asn Pro Leu Asn Lys Gln Met Ser Leu Asp Val His Ile
```

```
              1955               1960              1965

Thr  Ala  Ile  Lys  Asp  Glu  Asp  Gly  Lys  Arg  Ile  Ile  Val  Gly  Asp
          1970               1975              1980

Ala  Asn  Leu  Ser  Lys  Asp  Gly  Leu  Arg  Ile  Tyr  Glu  Val  Lys  Asp
          1985               1990              1995

Ile  Ala  Ile  Cys  Ile  Glu  Glu  Ala
          2000               2005

<210> SEQ ID NO 28
<211> LENGTH: 1963
<212> TYPE: PRT
<213> ORGANISM: Shewanella oneidensis

<400> SEQUENCE: 28

Met  Ser  Ser  Gln  Met  His  Thr  His  Pro  Thr  Leu  Gln  Asp  Ser  Ala  Ala
1                   5                   10                  15

Val  Pro  Asn  Asp  Gln  Arg  Gln  Thr  Leu  Lys  Ala  Met  Pro  Lys  Ile  Ala
                20                  25                  30

Ile  Val  Gly  Leu  Ala  Val  Gln  Tyr  Pro  Asp  Ala  Asp  Thr  Pro  Glu  Gln
            35                  40                  45

Phe  Trp  Gln  Asn  Leu  Leu  Asp  Lys  Lys  Asp  Ser  Arg  Ser  Gln  Ile  Asp
    50                  55                  60

Ala  Ala  Lys  Leu  Asn  Ala  Asn  Pro  Ala  Asp  Tyr  Gln  Gly  Ile  Gln  Gly
65                  70                  75                              80

Gln  Ala  Asp  Arg  Phe  Tyr  Cys  Asp  Lys  Gly  Gly  Tyr  Ile  Arg  Asn  Phe
                85                  90                  95

Arg  Phe  Asp  Pro  Gln  Gly  Tyr  Gln  Leu  Leu  Pro  Ala  Thr  Phe  Ala  Gly
            100                 105                 110

Leu  Asp  Glu  Ser  Phe  Leu  Trp  Ala  Leu  Asp  Cys  Ser  Lys  Lys  Ala  Leu
        115                 120                 125

Leu  Asn  Ala  Gly  Val  Asp  Leu  Thr  Ala  Pro  Leu  Leu  Glu  Arg  Thr  Gly
130                 135                 140

Ile  Val  Met  Gly  Thr  Leu  Ser  Phe  Pro  Thr  Ala  Arg  Ser  Asn  Glu  Leu
145                 150                 155                 160

Phe  Leu  Pro  Ile  Tyr  His  Gln  Ala  Val  Glu  Lys  Ala  Leu  Lys  Thr  Lys
                165                 170                 175

Leu  Asn  Gln  Pro  Gln  Phe  Ala  Leu  Ala  Pro  Phe  Ala  Asn  Ala  Ser  Ile
            180                 185                 190

Ala  Gly  Ser  Gln  Leu  Ala  Ala  Asn  Gly  Val  Ile  Ala  His  Thr  Ala  Ser
        195                 200                 205

Lys  Leu  Leu  Ser  Asp  Ala  Leu  Gly  Leu  Gly  Ala  Gln  Leu  Ser  Leu
210                 215                 220

Asp  Ala  Ala  Cys  Ala  Ser  Ser  Val  Tyr  Ala  Leu  Lys  Leu  Ala  Cys  Asp
225                 230                 235                 240

Tyr  Leu  Thr  Thr  Gly  Lys  Ala  Asp  Met  Met  Leu  Ala  Gly  Ala  Val  Ser
                245                 250                 255

Gly  Ala  Asp  Pro  Phe  Phe  Ile  Asn  Met  Gly  Phe  Ser  Ile  Phe  His  Ala
            260                 265                 270

Tyr  Pro  Asp  His  Gly  Ile  Ser  Ala  Pro  Phe  Asp  Ser  Asn  Ser  Lys  Gly
        275                 280                 285

Leu  Phe  Ala  Gly  Glu  Gly  Ala  Gly  Val  Leu  Val  Leu  Lys  Arg  Leu  Glu
        290                 295                 300

Asp  Ala  Glu  Arg  Asp  Gly  Asp  Asn  Ile  Tyr  Ala  Val  Val  Ser  Gly  Ile
305                 310                 315                 320
```

```
Gly Leu Ser Asn Asp Gly Lys Gly Gln Phe Val Leu Ser Pro Asn Ser
            325                 330                 335

Lys Gly Gln Val Gln Ala Phe Glu Arg Ala Tyr Ala Ala Ala Asn Thr
        340                 345                 350

His Pro Ser Asn Ile Glu Val Ile Glu Cys His Ala Thr Gly Thr Pro
    355                 360                 365

Leu Gly Asp Lys Val Glu Leu Thr Ser Met Glu Arg Phe Phe Glu Asp
370                 375                 380

Lys Leu Asp Gly Thr Lys Ala Pro Leu Ile Gly Ser Ala Lys Ser Asn
385                 390                 395                 400

Leu Gly His Leu Leu Thr Ala Ala Gly Met Pro Gly Ile Met Lys Met
                405                 410                 415

Ile Phe Ala Met Arg Ser Gly His Leu Pro Pro Ser Ile Asn Leu Thr
            420                 425                 430

Ala Pro Ile Ser Ser Pro Lys Gly Leu Phe Ser Val Asn Asn Leu Pro
        435                 440                 445

Thr Gln Arg Gln Ala Trp Pro Asp Lys Ala Gly Asn Asp Arg Arg His
    450                 455                 460

Ala Gly Val Ser Val Phe Gly Phe Gly Gly Cys Asn Ala His Leu Leu
465                 470                 475                 480

Leu Glu Ser Tyr Gln Pro Thr Ala His Ser Ala Glu Lys Gln Ala Asn
                485                 490                 495

Lys Pro Val Tyr Gln Gln Ala Leu Thr Val Ile Gly Met Ala Ser
            500                 505                 510

His Phe Gly Pro Leu Ala Ser Ile Asn Ala Leu Asp Lys Ala Leu Ile
        515                 520                 525

Ala Gln Thr Asp Ala Phe Ile Pro Leu Pro Pro Lys Arg Trp Lys Gly
    530                 535                 540

Leu Asp Lys His Pro Asp Ile Leu Gln Gln Phe Gly Leu Asn Arg Ala
545                 550                 555                 560

Pro Lys Gly Ala Tyr Ile Glu Gln Phe Asp Phe Asp Phe Leu Arg Phe
                565                 570                 575

Lys Val Pro Pro Asn Glu Asp Asp Arg Leu Ile Ser Gln Gln Leu Leu
            580                 585                 590

Leu Ile Lys Val Ala Asp Glu Ala Ile Arg Asp Ala Lys Leu Thr Ala
        595                 600                 605

Gly Ser Lys Val Ala Val Leu Val Ala Met Glu Thr Glu Leu Glu Leu
    610                 615                 620

His Gln Phe Arg Gly Arg Val Asn Leu His Thr Gln Leu Ala Asp Ser
625                 630                 635                 640

Leu Lys Lys Gln Gly Val His Leu Ser Asn Asp Glu Tyr Leu Ala Leu
                645                 650                 655

Glu Ala Ile Ala Met Asp Ser Val Leu Asp Ala Ala Lys Leu Asn Gln
            660                 665                 670

Tyr Thr Ser Phe Ile Gly Asn Ile Met Ala Ser Arg Ile Ala Ser Leu
        675                 680                 685

Trp Asp Phe Asn Gly Pro Ala Phe Thr Ile Ser Ala Ala Glu Gln Ser
    690                 695                 700

Val Ala Arg Cys Ile Asp Val Ala Gln Asn Leu Leu Ser Lys Glu Ala
705                 710                 715                 720

Leu Asp Gly Val Val Ile Ala Ala Val Asp Leu Ser Gly Ser Val Glu
                725                 730                 735

Gln Val Ile Leu Lys Asn Ala Gln Val Ala Val Asp Leu Asp Ala Asn
```

```
              740             745             750
Ser Ala Asn Pro Gln Trp Lys Val Gly Glu Gly Ala Gly Ile Val
            755             760             765
Leu Thr Asn Gln Gln Ala Ser Asn Ser Gln Gln Ala Gly Tyr Gly Gln
        770             775             780
Ile Arg Gly Gln Ala Phe Gly Thr Asn His Gln Leu Pro Lys Leu Leu
785             790             795             800
Asp Ser Leu Ile Thr Glu Thr Ala Ile Ala Asn Pro Ser Met Pro Thr
                805             810             815
Ala Ile His Met Ile Glu Gln Cys Ile Ala Pro Glu Glu Gln Leu Pro
            820             825             830
Ala Glu His Leu Leu Ala Gln Leu Asn Leu Leu Gly Thr Ser Cys Asn
            835             840             845
Arg Val Ala Asn Thr Leu Gly His Asn Phe Ala Ala Gly Met Ala
            850             855             860
Ser Leu Leu Ser Ala Leu Leu Ser Leu Lys Asn Arg Ser Ala Asn Ser
865             870             875             880
Asp Lys Asn Ala Glu Lys Gln Ala Leu Val Ser Thr Gln Ser Gln Gly
                885             890             895
Val Ser Ser Leu Leu Leu Ser Gln Thr Ala Thr Gln Ala Ala Gln
            900             905             910
Leu Glu Leu Arg Leu Ala Gln Asp Leu Thr Leu Ser Glu Gln Lys His
            915             920             925
Leu Ile Lys Pro Val Thr Leu Gly Gly Arg Asp Ile Tyr Gln His Ile
            930             935             940
Val Asp Thr Pro Leu Pro Ala Leu Ala Ala Ile Gln Gly Lys Met Arg
945             950             955             960
Gln Leu Gln Pro Leu Ala Ser Gln Ala Thr Gln Thr Lys Pro Ala Val
                965             970             975
Gly Ala Ala Leu Asp Ile Thr Ala Glu Asn Ala Thr Pro Leu Ala Ala
                980             985             990
Glu Ser Gly Met Ser Ser Asn Ala  Pro Leu Gln Phe Glu  Thr Thr Ala
            995             1000            1005
Ser Ala  Gln Asp Ser Ala Ala  Leu Leu Gln Asn Gln  Gln Leu Ala
    1010            1015            1020
Arg Glu  Ala His Leu Ala Phe  Leu Gln Ser Arg Glu  Gln Gly Leu
    1025            1030            1035
Lys Leu  Ala Asp Ala Leu Leu  Lys Ala Gln Leu Ser  Gln Thr Thr
    1040            1045            1050
Gln Met  Gly Ala Val Ala Ala  His Val Ala Thr Ser  Ala Asn Val
    1055            1060            1065
Ala Glu  Thr Lys Ala Gln Gln  Ala Val Ser Ile Pro  Glu Leu Met
    1070            1075            1080
Pro Asn  His Ala Pro Asn His  Ala Arg Val Pro Pro  Tyr Thr Pro
    1085            1090            1095
Pro Ile  Pro Ala Ala Lys Pro  Cys Ile Trp Asn Tyr  Gln Asp Leu
    1100            1105            1110
Val Glu  Tyr Ala Glu Gly Asp  Ile Ala Lys Val Phe  Gly Ala Asp
    1115            1120            1125
Tyr Ala  Ile Ile Asp Ser Tyr  Ala Arg Arg Val Arg  Leu Pro Thr
    1130            1135            1140
Ser Asp  Tyr Leu Leu Val Ser  Arg Val Thr Lys Leu  Asn Ala Gln
    1145            1150            1155
```

-continued

```
Met Asn Arg Tyr Gln Pro Ser Ser Met Thr Thr Glu Tyr Asp Ile
    1160                1165                1170

Pro Val Asp Ala Pro Phe Leu Val Asp Gly Gln Ile Pro Trp Ala
    1175                1180                1185

Val Ala Val Glu Ser Gly Gln Cys Asp Leu Met Leu Ile Ser Tyr
    1190                1195                1200

Leu Gly Ile Asp Phe Glu Asn Lys Gly Glu Arg Val Tyr Arg Leu
    1205                1210                1215

Leu Asp Cys Thr Leu Thr Phe Leu Gly Asp Leu Pro Arg Gly Gly
    1220                1225                1230

Asp Thr Leu Arg Tyr Asp Ile Ser Ile Asn His Phe Ala Arg Asn
    1235                1240                1245

Gly Asp Thr Leu Leu Phe Phe Ser Tyr Glu Cys Phe Val Gly
    1250                1255                1260

Asp Lys Leu Ile Leu Lys Met Asp Gly Gly Cys Ala Gly Phe Phe
    1265                1270                1275

Thr Asp Lys Glu Leu Ala Asp Gly Lys Gly Val Ile Arg Thr Glu
    1280                1285                1290

Val Glu Ile Lys Val Arg Glu Gln Ala Gln Ile Ala Leu Ala Asn
    1295                1300                1305

Glu Tyr Thr Arg Asn Gly Asn Lys Pro Arg Phe Thr Pro Leu Leu
    1310                1315                1320

Asn Cys Ala Gln Thr Ala Phe Ser Tyr Gly Gln Ile His Arg Leu
    1325                1330                1335

Leu Ser Ala Asp Ile Gly Gly Cys Phe Gly Gly Glu His Ala Ala
    1340                1345                1350

His Gln Ala Lys Phe Gly Leu Gln Pro Ser Leu Cys Phe Ala Ser
    1355                1360                1365

Glu Lys Phe Leu Met Ile Glu Gln Val Ser Lys Leu Glu Val His
    1370                1375                1380

Gly Gly Ala Trp Gly Leu Gly Leu Ile Glu Gly His Lys Gln Leu
    1385                1390                1395

Ala Pro Asp His Trp Tyr Phe Pro Cys His Phe Lys Gly Asp Gln
    1400                1405                1410

Val Met Ala Gly Ser Leu Met Ala Glu Gly Cys Gly Gln Leu Leu
    1415                1420                1425

Gln Phe Phe Met Leu His Ile Gly Met His Ala Asn Thr Gln Ala
    1430                1435                1440

Gly Gly Val Thr Asn Gly Arg Phe Gln Pro Leu Glu Asn Ala Ser
    1445                1450                1455

Gln Lys Val Arg Cys Arg Gly Gln Val Leu Pro Gln Ser Gly Thr
    1460                1465                1470

Leu Thr Tyr Arg Met Glu Val Thr Glu Ile Gly Met Ser Pro Arg
    1475                1480                1485

Pro Tyr Ala Lys Ala Asn Ile Asp Ile Leu Leu Asn Gly Lys Val
    1490                1495                1500

Val Val Asp Phe Gln Asn Leu Gly Val Met Ile Lys Glu Glu Ala
    1505                1510                1515

Asp Cys Thr Arg Tyr Ser Gln Ser His Ser Ser Gln Gly Asn His
    1520                1525                1530

Thr Gln Ala Ala Asn Ile Glu Ser Leu Ala Glu Gln Ala Pro Leu
    1535                1540                1545
```

```
Met Ala Gln Ile Pro Asp Val Ala Ala Pro Val Asn Lys Gly Val
1550                1555                1560

Val Pro Leu Lys His Val Ser Ala Pro Ile Ala Pro Ala Gly Ser
1565                1570                1575

Lys Tyr Ala Asn Arg Val Pro Asp Thr Leu Pro Phe Thr Pro Tyr
1580                1585                1590

His Leu Phe Glu Phe Ala Thr Gly Asp Ile Glu Asn Cys Phe Gly
1595                1600                1605

Pro Asp Phe Ser Ile Tyr Arg Gly Leu Ile Pro Pro Arg Thr Pro
1610                1615                1620

Cys Gly Asp Leu Gln Leu Thr Thr Arg Val Val Ala Ile Glu Gly
1625                1630                1635

Lys Arg Gly Glu Leu Lys Lys Pro Ser Thr Cys Ile Ala Glu Tyr
1640                1645                1650

Glu Val Pro Ser Asn Ala Trp Tyr Tyr Arg Lys Thr Ser His Pro
1655                1660                1665

Ser Val Met Pro Tyr Ser Val Leu Met Glu Ile Ser Leu Gln Pro
1670                1675                1680

Asn Gly Phe Ile Ser Gly Tyr Met Gly Thr Thr Leu Gly Phe Pro
1685                1690                1695

Gly Gln Glu Leu Phe Phe Arg Asn Leu Asp Gly Ser Gly Lys Leu
1700                1705                1710

Leu Arg Glu Val Asp Leu Arg Gly Lys Thr Ile Val Asn Asp Ser
1715                1720                1725

Arg Leu Leu Ser Thr Val Ile Ala Gly Ser Asn Ile Ile Gln Asn
1730                1735                1740

Phe Ser Phe Glu Leu Ser Cys Asp Gly Glu Pro Phe Tyr Arg Gly
1745                1750                1755

Asn Ala Val Phe Gly Tyr Phe Lys Ala Asp Ala Leu Lys Asn Gln
1760                1765                1770

Leu Gly Ile Asp Asn Gly Lys Ile Thr Gln Ala Trp His Leu Glu
1775                1780                1785

Arg Gly Ile Lys Ala Asp Cys Gln Ile Asn Leu Leu Asp Lys Asn
1790                1795                1800

Gly Arg Ser Phe Val Ala Pro Leu Gly Lys Pro His Tyr Arg Leu
1805                1810                1815

Ala Gly Gly Gln Leu Asn Phe Ile Asp Lys Ala Glu Ile Val Lys
1820                1825                1830

Thr Gly Gly Lys Lys Gly Leu Gly Tyr Leu Tyr Ala Glu Arg Thr
1835                1840                1845

Ile Asp Pro Ser Asp Trp Phe Phe Gln Phe His Phe His Gln Asp
1850                1855                1860

Pro Val Met Pro Gly Ser Leu Gly Val Glu Ala Ile Ile Glu Leu
1865                1870                1875

Leu Gln Thr Tyr Ala Ile Asp Gln Asp Leu Gly Ala Gly Phe Asn
1880                1885                1890

Asn Pro Lys Phe Gly Gln Ile Leu Ser Glu Ile Lys Trp Lys Tyr
1895                1900                1905

Arg Gly Gln Ile Asn Pro Leu Asn Lys Gln Met Ser Leu Asp Val
1910                1915                1920

His Ile Thr Ser Ile Glu Asp Lys Asp Gly Lys Arg Ile Ile Lys
1925                1930                1935

Gly Asp Ala Asn Leu Ser Lys Asp Gly Leu Arg Ile Tyr Glu Val
```

-continued

```
                1940                1945                1950
        Thr Asp Ile Ala Ile Cys Ile Glu Glu Ala
            1955                1960

<210> SEQ ID NO 29
<211> LENGTH: 2011
<212> TYPE: PRT
<213> ORGANISM: Moritella marina

<400> SEQUENCE: 29

Met Glu Asn Ile Ala Val Val Gly Ile Ala Asn Leu Phe Pro Gly Ser
1               5                   10                  15

Gln Ala Pro Asp Gln Phe Trp Gln Gln Leu Leu Glu Gln Gln Asp Cys
            20                  25                  30

Arg Ser Lys Ala Thr Ala Val Gln Met Gly Val Asp Pro Ala Lys Tyr
        35                  40                  45

Thr Ala Asn Lys Gly Asp Thr Asp Lys Phe Tyr Cys Val His Gly Gly
    50                  55                  60

Tyr Ile Ser Asp Phe Asn Phe Asp Ala Ser Gly Tyr Gln Leu Asp Asn
65                  70                  75                  80

Asp Tyr Leu Ala Gly Leu Asp Asp Leu Asn Gln Trp Gly Leu Tyr Val
                85                  90                  95

Thr Lys Gln Ala Leu Thr Asp Ala Gly Tyr Trp Gly Ser Thr Ala Leu
            100                 105                 110

Glu Asn Cys Gly Val Ile Leu Gly Asn Leu Ser Phe Pro Thr Lys Ser
        115                 120                 125

Ser Asn Gln Leu Phe Met Pro Leu Tyr His Gln Val Val Asp Asn Ala
    130                 135                 140

Leu Lys Ala Val Leu His Pro Asp Phe Gln Leu Thr His Tyr Thr Ala
145                 150                 155                 160

Pro Lys Lys Thr His Ala Asp Asn Ala Leu Val Ala Gly Tyr Pro Ala
                165                 170                 175

Ala Leu Ile Ala Gln Ala Ala Gly Leu Gly Gly Ser His Phe Ala Leu
            180                 185                 190

Asp Ala Ala Cys Ala Ser Ser Cys Tyr Ser Val Lys Leu Ala Cys Asp
        195                 200                 205

Tyr Leu His Thr Gly Lys Ala Asn Met Met Leu Ala Gly Ala Val Ser
    210                 215                 220

Ala Ala Asp Pro Met Phe Val Asn Met Gly Phe Ser Ile Phe Gln Ala
225                 230                 235                 240

Tyr Pro Ala Asn Asn Val His Ala Pro Phe Asp Gln Asn Ser Gln Gly
                245                 250                 255

Leu Phe Ala Gly Glu Gly Ala Gly Met Met Val Leu Lys Arg Gln Ser
            260                 265                 270

Asp Ala Val Arg Asp Gly Asp His Ile Tyr Ala Ile Ile Lys Gly Gly
        275                 280                 285

Ala Leu Ser Asn Asp Gly Lys Gly Glu Phe Val Leu Ser Pro Asn Thr
    290                 295                 300

Lys Gly Gln Val Leu Val Tyr Glu Arg Ala Tyr Ala Asp Ala Asp Val
305                 310                 315                 320

Asp Pro Ser Thr Val Asp Tyr Ile Glu Cys His Ala Thr Gly Thr Pro
                325                 330                 335

Lys Gly Asp Asn Val Glu Leu Arg Ser Met Glu Thr Phe Phe Ser Arg
            340                 345                 350
```

-continued

Val Asn Asn Lys Pro Leu Leu Gly Ser Val Lys Ser Asn Leu Gly His
      355                 360                 365

Leu Leu Thr Ala Ala Gly Met Pro Gly Met Thr Lys Ala Met Leu Ala
370                 375                 380

Leu Gly Lys Gly Leu Ile Pro Ala Thr Ile Asn Leu Lys Gln Pro Leu
385                 390                 395                 400

Gln Ser Lys Asn Gly Tyr Phe Thr Gly Glu Gln Met Pro Thr Thr Thr
              405                 410                 415

Val Ser Trp Pro Thr Thr Pro Gly Ala Lys Ala Asp Lys Pro Arg Thr
          420                 425                 430

Ala Gly Val Ser Val Phe Gly Phe Gly Gly Ser Asn Ala His Leu Val
      435                 440                 445

Leu Gln Gln Pro Thr Gln Thr Leu Glu Thr Asn Phe Ser Val Ala Lys
  450                 455                 460

Pro Arg Glu Pro Leu Ala Ile Ile Gly Met Asp Ser His Phe Gly Ser
465                 470                 475                 480

Ala Ser Asn Leu Ala Gln Phe Lys Thr Leu Asn Asn Asn Gln Asn
              485                 490                 495

Thr Phe Arg Glu Leu Pro Glu Gln Arg Trp Lys Gly Met Glu Ser Asn
          500                 505                 510

Ala Asn Val Met Gln Ser Leu Gln Leu Arg Lys Ala Pro Lys Gly Ser
      515                 520                 525

Tyr Val Glu Gln Leu Asp Ile Asp Phe Leu Arg Phe Lys Val Pro Pro
  530                 535                 540

Asn Glu Lys Asp Cys Leu Ile Pro Gln Gln Leu Met Met Met Gln Val
545                 550                 555                 560

Ala Asp Asn Ala Ala Lys Asp Gly Gly Leu Val Glu Gly Arg Asn Val
              565                 570                 575

Ala Val Leu Val Ala Met Gly Met Glu Leu Glu Leu His Gln Tyr Arg
          580                 585                 590

Gly Arg Val Asn Leu Thr Thr Gln Ile Glu Asp Ser Leu Leu Gln Gln
      595                 600                 605

Gly Ile Asn Leu Thr Val Glu Gln Arg Glu Glu Leu Thr Asn Ile Ala
  610                 615                 620

Lys Asp Gly Val Ala Ser Ala Ala Gln Leu Asn Gln Tyr Thr Ser Phe
625                 630                 635                 640

Ile Gly Asn Ile Met Ala Ser Arg Ile Ser Ala Leu Trp Asp Phe Ser
              645                 650                 655

Gly Pro Ala Ile Thr Val Ser Ala Glu Glu Asn Ser Val Tyr Arg Cys
          660                 665                 670

Val Glu Leu Ala Glu Asn Leu Phe Gln Thr Ser Asp Val Glu Ala Val
      675                 680                 685

Ile Ile Ala Ala Val Asp Leu Ser Gly Ser Ile Glu Asn Ile Thr Leu
  690                 695                 700

Arg Gln His Tyr Gly Pro Val Asn Glu Lys Gly Ser Val Ser Glu Cys
705                 710                 715                 720

Gly Pro Val Asn Glu Ser Ser Val Thr Asn Asn Ile Leu Asp Gln
              725                 730                 735

Gln Gln Trp Leu Val Gly Glu Gly Ala Ala Ile Val Val Lys Pro
          740                 745                 750

Ser Ser Gln Val Thr Ala Glu Gln Val Tyr Ala Arg Ile Asp Ala Val
      755                 760                 765

Ser Phe Ala Pro Gly Ser Asn Ala Lys Ala Ile Thr Ile Ala Ala Asp

```
                770             775              780
Lys Ala Leu Thr Leu Ala Gly Ile Ser Ala Ala Asp Val Ala Ser Val
785              790              795              800
Glu Ala His Ala Ser Gly Phe Ser Ala Glu Asn Asn Ala Glu Lys Thr
                805              810              815
Ala Leu Pro Thr Leu Tyr Pro Ser Ala Ser Ile Ser Ser Val Lys Ala
                820              825              830
Asn Ile Gly His Thr Phe Asn Ala Ser Gly Met Ala Ser Ile Ile Lys
                835              840              845
Thr Ala Leu Leu Leu Asp Gln Asn Thr Ser Gln Asp Gln Lys Ser Lys
850              855              860
His Ile Ala Ile Asn Gly Leu Gly Arg Asp Asn Ser Cys Ala His Leu
865              870              875              880
Ile Leu Ser Ser Ser Ala Gln Ala His Gln Val Ala Pro Ala Pro Val
                885              890              895
Ser Gly Met Ala Lys Gln Arg Pro Gln Leu Val Lys Thr Ile Lys Leu
                900              905              910
Gly Gly Gln Leu Ile Ser Asn Ala Ile Val Asn Ser Ala Ser Ser Ser
                915              920              925
Leu His Ala Ile Lys Ala Gln Phe Ala Gly Lys His Leu Asn Lys Val
                930              935              940
Asn Gln Pro Val Met Met Asp Asn Leu Lys Pro Gln Gly Ile Ser Ala
945              950              955              960
His Ala Thr Asn Glu Tyr Val Val Thr Gly Ala Ala Asn Thr Gln Ala
                965              970              975
Ser Asn Ile Gln Ala Ser His Val Gln Ala Ser Ser His Ala Gln Glu
                980              985              990
Ile Ala Pro Asn Gln Val Gln Asn Met Gln Ala Thr Ala Ala Ala Val
                995              1000             1005
Ser Ser Pro Leu Ser Gln His Gln His Thr Ala Gln Pro Val Ala
    1010             1015             1020
Ala Pro Ser Val Val Gly Val Thr Val Lys His Lys Ala Ser Asn
    1025             1030             1035
Gln Ile His Gln Gln Ala Ser Thr His Lys Ala Phe Leu Glu Ser
    1040             1045             1050
Arg Leu Ala Ala Gln Lys Asn Leu Ser Gln Leu Val Glu Leu Gln
    1055             1060             1065
Thr Lys Leu Ser Ile Gln Thr Gly Ser Asp Asn Thr Ser Asn Asn
    1070             1075             1080
Thr Ala Ser Thr Ser Asn Thr Val Leu Thr Asn Pro Val Ser Ala
    1085             1090             1095
Thr Pro Leu Thr Leu Val Ser Asn Ala Pro Val Val Ala Thr Asn
    1100             1105             1110
Leu Thr Ser Thr Glu Ala Lys Ala Gln Ala Ala Thr Gln Ala
    1115             1120             1125
Gly Phe Gln Ile Lys Gly Pro Val Gly Tyr Asn Tyr Pro Pro Leu
    1130             1135             1140
Gln Leu Ile Glu Arg Tyr Asn Lys Pro Glu Asn Val Ile Tyr Asp
    1145             1150             1155
Gln Ala Asp Leu Val Glu Phe Ala Glu Gly Asp Ile Gly Lys Val
    1160             1165             1170
Phe Gly Ala Glu Tyr Asn Ile Ile Asp Gly Tyr Ser Arg Arg Val
    1175             1180             1185
```

-continued

Arg Leu Pro Thr Ser Asp Tyr Leu Leu Val Thr Arg Val Thr Glu
    1190            1195              1200

Leu Asp Ala Lys Val His Glu Tyr Lys Lys Ser Tyr Met Cys Thr
    1205            1210              1215

Glu Tyr Asp Val Pro Val Asp Ala Pro Phe Leu Ile Asp Gly Gln
    1220            1225              1230

Ile Pro Trp Ser Val Ala Val Glu Ser Gly Gln Cys Asp Leu Met
    1235            1240              1245

Leu Ile Ser Tyr Ile Gly Ile Asp Phe Gln Ala Lys Gly Glu Arg
    1250            1255              1260

Val Tyr Arg Leu Leu Asp Cys Glu Leu Thr Phe Leu Glu Glu Met
    1265            1270              1275

Ala Phe Gly Gly Asp Thr Leu Arg Tyr Glu Ile His Ile Asp Ser
    1280            1285              1290

Tyr Ala Arg Asn Gly Glu Gln Leu Leu Phe Phe His Tyr Asp
    1295            1300              1305

Cys Tyr Val Gly Asp Lys Lys Val Leu Ile Met Arg Asn Gly Cys
    1310            1315              1320

Ala Gly Phe Phe Thr Asp Glu Glu Leu Ser Asp Gly Lys Gly Val
    1325            1330              1335

Ile His Asn Asp Lys Asp Lys Ala Glu Phe Ser Asn Ala Val Lys
    1340            1345              1350

Ser Ser Phe Thr Pro Leu Leu Gln His Asn Arg Gly Gln Tyr Asp
    1355            1360              1365

Tyr Asn Asp Met Met Lys Leu Val Asn Gly Asp Val Ala Ser Cys
    1370            1375              1380

Phe Gly Pro Gln Tyr Asp Gln Gly Gly Arg Asn Pro Ser Leu Lys
    1385            1390              1395

Phe Ser Ser Glu Lys Phe Leu Met Ile Glu Arg Ile Thr Lys Ile
    1400            1405              1410

Asp Pro Thr Gly Gly His Trp Gly Leu Gly Leu Leu Glu Gly Gln
    1415            1420              1425

Lys Asp Leu Asp Pro Glu His Trp Tyr Phe Pro Cys His Phe Lys
    1430            1435              1440

Gly Asp Gln Val Met Ala Gly Ser Leu Met Ser Glu Gly Cys Gly
    1445            1450              1455

Gln Met Ala Met Phe Phe Met Leu Ser Leu Gly Met His Thr Asn
    1460            1465              1470

Val Asn Asn Ala Arg Phe Gln Pro Leu Pro Gly Glu Ser Gln Thr
    1475            1480              1485

Val Arg Cys Arg Gly Gln Val Leu Pro Gln Arg Asn Thr Leu Thr
    1490            1495              1500

Tyr Arg Met Glu Val Thr Ala Met Gly Met His Pro Gln Pro Phe
    1505            1510              1515

Met Lys Ala Asn Ile Asp Ile Leu Leu Asp Gly Lys Val Val Val
    1520            1525              1530

Asp Phe Lys Asn Leu Ser Val Met Ile Ser Glu Gln Asp Glu His
    1535            1540              1545

Ser Asp Tyr Pro Val Thr Leu Pro Ser Asn Val Ala Leu Lys Ala
    1550            1555              1560

Ile Thr Ala Pro Val Ala Ser Val Ala Pro Ala Ser Ser Pro Ala
    1565            1570              1575

```
Asn Ser Ala Asp Leu Asp Glu Arg Gly Val Glu Pro Phe Lys Phe
    1580            1585                1590

Pro Glu Arg Pro Leu Met Arg Val Glu Ser Asp Leu Ser Ala Pro
    1595            1600                1605

Lys Ser Lys Gly Val Thr Pro Ile Lys His Phe Glu Ala Pro Ala
    1610            1615                1620

Val Ala Gly His His Arg Val Pro Asn Gln Ala Pro Phe Thr Pro
    1625            1630                1635

Trp His Met Phe Glu Phe Ala Thr Gly Asn Ile Ser Asn Cys Phe
    1640            1645                1650

Gly Pro Asp Phe Asp Val Tyr Glu Gly Arg Ile Pro Pro Arg Thr
    1655            1660                1665

Pro Cys Gly Asp Leu Gln Val Val Thr Gln Val Val Glu Val Gln
    1670            1675                1680

Gly Glu Arg Leu Asp Leu Lys Asn Pro Ser Ser Cys Val Ala Glu
    1685            1690                1695

Tyr Tyr Val Pro Glu Asp Ala Trp Tyr Phe Thr Lys Asn Ser His
    1700            1705                1710

Glu Asn Trp Met Pro Tyr Ser Leu Ile Met Glu Ile Ala Leu Gln
    1715            1720                1725

Pro Asn Gly Phe Ile Ser Gly Tyr Met Gly Thr Thr Leu Lys Tyr
    1730            1735                1740

Pro Glu Lys Asp Leu Phe Phe Arg Asn Leu Asp Gly Ser Gly Thr
    1745            1750                1755

Leu Leu Lys Gln Ile Asp Leu Arg Gly Lys Thr Ile Val Asn Lys
    1760            1765                1770

Ser Val Leu Val Ser Thr Ala Ile Ala Gly Gly Ala Ile Ile Gln
    1775            1780                1785

Ser Phe Thr Phe Asp Met Ser Val Asp Gly Glu Leu Phe Tyr Thr
    1790            1795                1800

Gly Lys Ala Val Phe Gly Tyr Phe Ser Gly Glu Ser Leu Thr Asn
    1805            1810                1815

Gln Leu Gly Ile Asp Asn Gly Lys Thr Thr Asn Ala Trp Phe Val
    1820            1825                1830

Asp Asn Asn Thr Pro Ala Ala Asn Ile Asp Val Phe Asp Leu Thr
    1835            1840                1845

Asn Gln Ser Leu Ala Leu Tyr Lys Ala Pro Val Asp Lys Pro His
    1850            1855                1860

Tyr Lys Leu Ala Gly Gly Gln Met Asn Phe Ile Asp Thr Val Ser
    1865            1870                1875

Val Val Glu Gly Gly Lys Ala Gly Val Ala Tyr Val Tyr Gly
    1880            1885                1890

Glu Arg Thr Ile Asp Ala Asp Trp Phe Phe Arg Tyr His Phe
    1895            1900                1905

His Gln Asp Pro Val Met Pro Gly Ser Leu Gly Val Glu Ala Ile
    1910            1915                1920

Ile Glu Leu Met Gln Thr Tyr Ala Leu Lys Asn Asp Leu Gly Gly
    1925            1930                1935

Lys Phe Ala Asn Pro Arg Phe Ile Ala Pro Met Thr Gln Val Asp
    1940            1945                1950

Trp Lys Tyr Arg Gly Gln Ile Thr Pro Leu Asn Lys Gln Met Ser
    1955            1960                1965

Leu Asp Val His Ile Thr Glu Ile Val Asn Asp Ala Gly Glu Val
```

```
                1970                1975                1980
Arg Ile Val Gly Asp Ala Asn Leu Ser Lys Asp Gly Leu Arg Ile
        1985                1990                1995
Tyr Glu Val Lys Asn Ile Val Leu Ser Ile Val Glu Ala
        2000                2005                2010
```

<210> SEQ ID NO 30
<211> LENGTH: 2241
<212> TYPE: PRT
<213> ORGANISM: Aureispira marina

<400> SEQUENCE: 30

```
Met Lys Ile Ala Ile Ile Gly Leu Ser Gly Leu Phe Pro Gly Ser Ser
1               5                   10                  15

Thr Asn Glu Glu Phe Trp Gln Asn Leu Leu Asp Glu Lys Asp Leu Thr
                20                  25                  30

Asn Leu Ala Asn Leu Glu Asp Phe Gly Ala Asp Pro Ala Leu Phe Tyr
            35                  40                  45

Glu Asp Lys Lys Gly Ala Val Asp Arg Cys Tyr Ser Leu Arg Gly Gly
        50                  55                  60

Tyr Ile Arg Asp Phe Asp Phe Asp Pro Thr Gly Tyr Gln Leu Ser Ala
65                  70                  75                  80

Asp Phe Leu Ala Gln Gln Asp Lys Leu Tyr Gln Trp Ser Leu Tyr Val
                85                  90                  95

Ala Lys Thr Ala Leu Glu Glu Ser Gly Tyr Ala His Asn Lys Glu Val
            100                 105                 110

Leu Ala Lys Cys Gly Leu Ile Leu Gly Asn Leu Ser Phe Pro Thr Gly
        115                 120                 125

Ser Ser His Lys Leu Leu Ala Asp Leu Tyr Thr Lys Thr Thr Glu Lys
130                 135                 140

Ala Leu Gln Glu Leu Leu Glu Asp Lys Asn Phe Lys Ile Pro Ala Ser
145                 150                 155                 160

Gln Leu Pro Ile Pro Asn Asn Glu Val Leu Ala Asp Thr Pro Ser Gln
                165                 170                 175

Met Val Ala Lys Gly Leu Gly Leu Gly Gly His Tyr Ala Leu Asp
            180                 185                 190

Ala Ala Cys Ala Thr Ser Leu Tyr Ala Ile Lys Leu Ala Cys Asp Glu
        195                 200                 205

Leu Ile Thr Gly Lys Ala Asp Leu Met Leu Ala Gly Ala Val Cys Gly
        210                 215                 220

Ser Asp Gln Leu Phe Ile His Met Gly Phe Ser Ile Phe His Ala Tyr
225                 230                 235                 240

Ala Pro His Gly Glu Lys Phe Ala Pro Leu Asp Lys Ala Ser Gly Gly
                245                 250                 255

Leu Val Ser Ala Glu Gly Ala Gly Met Val Val Leu Lys Arg Leu Glu
            260                 265                 270

Asp Ala Glu Arg Asp Gly Asp Asn Ile Leu Gly Leu Ile Gly Gly Ile
        275                 280                 285

Gly Leu Ser Asn Asp Gly Ser Gly Lys Phe Leu Leu Ser Pro Asn Pro
    290                 295                 300

Lys Gly Gln Arg Leu Ala Phe Glu Arg Ala Tyr Asp Leu Glu Glu Val
305                 310                 315                 320

Leu Pro Gln Asn Thr Ser Tyr Leu Glu Cys His Ala Thr Gly Thr Pro
                325                 330                 335
```

```
Leu Gly Asp Val Thr Glu Met Asn Ser Ile Ser Asp Phe Phe Ala Gln
                340                 345                 350

His Gln Thr Lys Pro Leu Leu Gly Ser Val Lys Ser Asn Met Gly His
            355                 360                 365

Leu Leu Thr Ala Ala Gly Met Ser Gly Leu Phe Lys Val Leu Leu Ser
        370                 375                 380

Met Gln Lys Gly Ile Ile Pro Pro Asn Ile Asn Leu Glu Ser Ala Val
385                 390                 395                 400

Gln Ala Asn Asn Gln Trp Ile Gln Asp Glu Gln Ile Ile Lys Lys Thr
                405                 410                 415

Thr Pro Trp Lys Gly Asp Gln Ala Gly Ile Asn Ser Phe Gly Phe Gly
            420                 425                 430

Gly Thr Asn Ala His Met Val Val Gln Lys Pro Thr Ser Ser Thr Leu
        435                 440                 445

Lys Glu Lys Lys Ala Tyr Gln Ala Gln Glu Leu Leu Pro Leu Ala Ile
            450                 455                 460

Val Gly Met Asp Ala His Phe Gly Ser Cys Glu Asn Leu Glu Asp Phe
465                 470                 475                 480

Tyr Ala Ala Ile Tyr Asn Gly Asn Gln Asp Phe Lys Pro Leu Pro Pro
                485                 490                 495

Lys Arg Trp Lys Gly Phe Asp Ala Asp Gln Asp Leu Leu Lys Arg Tyr
            500                 505                 510

Gly Phe Lys Asp Gly Leu Ala Pro Lys Gly Ala Tyr Ile Asp Gln Phe
        515                 520                 525

Asp Ile Asp Leu Leu Arg Tyr Lys Ile Gln Pro Lys Glu Ala Glu Thr
530                 535                 540

Leu Glu Pro Gln Gln Ala Leu Ile Leu Lys Val Ala Asp Lys Ala Leu
545                 550                 555                 560

Gln Asp Ala Gln Ile Ser Pro Ser Gln Asn Ile Ala Val Leu Ile Ala
                565                 570                 575

Met Glu Ser Glu Leu Ala Ile His His Tyr Leu Ala Arg Trp Asp Ser
            580                 585                 590

Val Trp Gln Leu Asp Lys Ala Leu Glu Gln Ser Gly Leu Ser Leu Ser
        595                 600                 605

Glu Glu Lys Lys Thr Ala Leu Lys Glu Tyr Ser Lys Asn Ala Leu Tyr
610                 615                 620

Phe Arg Glu Gly Ser Gln Thr Pro Ser Gln His Thr Ser Phe Val Gly
625                 630                 635                 640

Asn Ile Met Ala Ser Arg Ile Ala Ala Leu Trp Asp Phe Ser Gly Pro
                645                 650                 655

Ala Phe Thr Val Ser Cys Gly Asp Asn Ala Val Phe Lys Ala Leu Glu
            660                 665                 670

Val Ala Gln Asn Ile Leu Ser Leu Gly Glu Val Asp Ala Val Val Val
        675                 680                 685

Gly Gly Val Asp Phe Cys Gly Gly Leu Glu Asn Val Leu Leu Arg Gln
690                 695                 700

Glu Lys Glu Ala Ser Ser Gln Asn Ile Ala Pro Ser Leu Ser Leu Asn
705                 710                 715                 720

Gln Gly Gln Lys Gly Trp Leu Val Gly Glu Gly Ala Gly Ala Val Val
                725                 730                 735

Leu Lys Arg Gln Ile Asp Leu Gln Lys Gln Asp Asn Val Tyr Ala Val
            740                 745                 750

Leu Glu His Ile Gly Gln Ala Ser Glu Gln Leu Asn Val Gly Tyr Gln
```

-continued

```
            755                 760                 765
Glu Leu Val Ser Ser Gly Tyr Ala Ala Gln Asp His Gln Glu Leu Lys
770                 775                 780
Gln Leu Leu Ala Thr Gln Leu Glu Gln Lys Thr Ala Leu Gly Ser Val
785                 790                 795                 800
Lys Thr Ser Phe Gly His Thr Gly Ala Ala Ser Gly Ile Ala Ala Leu
                805                 810                 815
Ile Lys Thr Ala Leu Cys Leu His His Lys Phe Ile Pro Gly Ile Pro
                820                 825                 830
Asn Trp Glu Ala Pro Gln Glu Ala Thr Ala Phe Ala Lys Thr Lys Tyr
                835                 840                 845
Tyr Phe Pro Met Ala Ser Arg Pro Trp Leu Leu Asn Ala Gly Glu Lys
850                 855                 860
Arg Lys Ala Ala Ile Asn Gly Leu Glu Gly Leu Gln Ile His Leu Ser
865                 870                 875                 880
Glu Gly Val Arg Ser Ser Pro Ala Pro Ser Pro Leu Leu Gln Gly Arg
                885                 890                 895
Val Gly Ser Leu Phe Val Leu Lys Gly Asn Thr Glu Thr Ala Leu Arg
                900                 905                 910
Glu Ala Leu Ala Leu Leu Leu Glu Asp Leu Ala Gly Lys Ser Ser Leu
                915                 920                 925
Pro Glu Leu Ala Ala Arg Leu Tyr Tyr Asn His Gln Ala Lys Pro Ser
930                 935                 940
Ser Tyr Thr Ile Val Leu Leu Ala Asn Ser Lys Lys Asn Leu Gln Gln
945                 950                 955                 960
Glu Ile Arg Phe Met Gln Val Gly Leu Glu Ala Ala Leu Thr Glu Asn
                965                 970                 975
Lys Val Leu Lys Thr Pro Arg Gly Ser Tyr Phe Thr Ala Lys Pro Leu
                980                 985                 990
Gly Lys Thr Gly Lys Ile Ala Phe Ser Tyr Pro Gly Ser Ala Thr Ala
                995                 1000                1005
Tyr Arg Gly Leu Gly Gln Asp Ile Phe Gln Leu Phe Pro Ser Leu
    1010                1015                1020
His Glu His Phe Gly Gln Lys Leu Glu Asp Ile Ala Asp Phe Val
    1025                1030                1035
Gly Ser Ser Tyr Leu His Pro Lys Leu Gln Ser Arg Gln Glu Glu
    1040                1045                1050
Ala Pro Ser Ile Gln Thr Asp Ala Val Ser Met Met Cys Ala Gly
    1055                1060                1065
Val Phe Ser Ser Ala Ile Tyr Thr His Leu Leu Lys Asp Lys Phe
    1070                1075                1080
Gly Leu Lys Pro Asp Leu Ala Phe Gly Tyr Ser Met Gly Glu Ser
    1085                1090                1095
Ala Gly Met Trp Tyr Ser Phe Asp Val Trp Asn Pro Asp Asn Thr
    1100                1105                1110
Ala Val Phe Arg Asn Ser Asp Leu Phe Ala Asn Gln Leu Ser Gly
    1115                1120                1125
Asp Leu Arg Leu Leu Ala Glu Thr Trp Gly Ile Ser Ser Glu Glu
    1130                1135                1140
Ala Lys Ala Arg Trp Ile Ser Leu Ile Leu Leu Ala Asp Lys Glu
    1145                1150                1155
Ala Val Gln Asn Leu Val Ala Gln Glu Asp Arg Cys Tyr Leu Ser
    1160                1165                1170
```

```
Phe Ile Asn Thr Pro Gln Glu Val Ile Ile Ser Gly Asp Lys Glu
1175                 1180                1185

Ala Cys Asn Arg Val Val Gln Gln Leu Gly Cys Pro Ala Val Glu
1190                 1195                1200

Val Pro Phe Gln Asn Val Ile His His Asp Phe Cys Lys Lys Val
1205                 1210                1215

Gln Glu Glu Leu Tyr Asp Met His His Phe Pro Leu Glu Thr Gln
1220                 1225                1230

Pro Asn Ile Asp Phe Tyr Ser Ser Leu Ser Leu Ala Pro Leu Pro
1235                 1240                1245

Met Asp Ser Gly Val Ile Ala Gln Asn Ser Thr Gln Val Cys Phe
1250                 1255                1260

Gln Pro Val Asp Tyr Pro Thr Thr Ile Gln Gln Leu Tyr Asn Asp
1265                 1270                1275

Gly Ala Arg Ile Phe Ile Glu Leu Gly Ala Gly Asn Thr Cys Thr
1280                 1285                1290

Gln Trp Thr Ser Ser Ile Leu Gly Gln Gln Ala His Leu Ala Val
1295                 1300                1305

Ser Cys Thr Gln Lys Gly Lys Pro Glu Gly Thr Ala Leu Leu Gln
1310                 1315                1320

Ala Leu Ala Gln Leu Leu Ser His Gly Val Ala Leu Asp Leu Gln
1325                 1330                1335

Pro Leu Phe Ala Ala Asp Leu Leu Ala Pro Ser Pro Arg Ala Phe
1340                 1345                1350

Tyr Lys Ala Ile Val Ser Gly Gly Ala Arg Ile Phe Asp Tyr Leu
1355                 1360                1365

Leu Gln Pro Gln Thr Lys Lys Gln Phe Ala Gly Val Thr Lys Thr
1370                 1375                1380

Ala Leu Val Gln Gln Leu Glu Pro Ala Leu Ala Ser Asn Ser Arg
1385                 1390                1395

Glu Tyr Ser Phe Thr Ser Thr Lys Thr Thr Thr Val Asp Thr Thr
1400                 1405                1410

Gln Ser Ile Pro Ser Pro Ser Gln Lys Val Leu Leu Gly Glu Asn
1415                 1420                1425

Gly Leu Lys Leu Gln Asp Phe Asn Asp Pro Asn His Leu Gln Gly
1430                 1435                1440

Lys Thr Ile Ile Phe Ser Gln Glu Asp Leu Glu Glu Phe Ala Thr
1445                 1450                1455

Gly Lys Ile Ala Lys Val Phe Gly Glu Glu Tyr Ser Ile Ile Asp
1460                 1465                1470

Thr Tyr Lys Arg Arg Val Met Leu Pro Met Ala Pro Tyr Leu Leu
1475                 1480                1485

Val Ser Arg Val Thr Gly Leu Asp Ala Lys Arg Gly Glu Phe Lys
1490                 1495                1500

Pro Ser Thr Met Gln Thr Glu Tyr Asp Ile Pro Tyr Asn Ala Trp
1505                 1510                1515

Phe Thr Thr Asp Gly Gln Ile Pro Trp Ala Val Ser Val Glu Ser
1520                 1525                1530

Gly Gln Cys Asp Leu Leu Leu Ile Ser Tyr Leu Gly Ile Asp Phe
1535                 1540                1545

Glu Asn Lys Gly Asp Leu Val Tyr Arg Leu Leu Asp Cys Thr Leu
1550                 1555                1560
```

```
Thr Phe Val Asp Asp Leu Pro Phe Glu Gly Gln Thr Leu Arg Tyr
1565                1570                1575

Asp Ile Ser Ile Asn Ser Phe Val Arg Asn Gly Asp Asn Leu Leu
1580                1585                1590

Phe Phe Phe Ser Tyr Asn Cys Tyr Val Glu Asp Arg Leu Val Leu
1595                1600                1605

Lys Met Arg Asn Gly Cys Ala Gly Phe Phe Thr Asp Glu Gln Leu
1610                1615                1620

Glu Glu Gly Leu Gly Val Val Tyr Ser Lys Glu Glu Leu Glu Ala
1625                1630                1635

Lys Thr Asn Ala Lys Lys Pro Ala Phe Thr Pro Leu Leu Asn Thr
1640                1645                1650

Lys Lys Thr Ser Phe Ser Lys Glu Asp Leu His His Leu Ile Glu
1655                1660                1665

Gly Asn Met Glu Leu Cys Phe Asp Ser Pro Ala Tyr Phe Ala Asn
1670                1675                1680

Gly Arg Asn Pro Ser Leu Arg Leu Pro Pro Glu Gln Ile Leu Met
1685                1690                1695

Ile Asp Arg Ile Val Ser Val Asp Leu Lys Gly Gly Ala Tyr Gly
1700                1705                1710

Leu Gly Tyr Val Ile Ala Glu Lys Asp Leu Ala Pro Glu Asp Trp
1715                1720                1725

Tyr Phe Pro Cys His Phe Arg Asp Asp Glu Val Leu Ala Gly Ser
1730                1735                1740

Leu Gln Ala Glu Gly Gly Asn Leu Leu Arg Phe Phe Met Leu
1745                1750                1755

Met Leu Gly Leu Gln Arg Leu Thr Lys Asp Ala Arg Tyr Gln Pro
1760                1765                1770

Ile Phe Asp Leu Pro Gln Lys Val Arg Cys Arg Lys Gln Val Thr
1775                1780                1785

Pro Ser Lys Asp Thr Lys Leu Val Tyr Lys Leu Glu Val Lys Glu
1790                1795                1800

Ile Gly Leu Val Pro Asn Pro Tyr Val Ile Ala Asp Leu Glu Ile
1805                1810                1815

Val Ser Asp Gly Val Ile Thr Val His Phe Glu Asn Leu Gly Leu
1820                1825                1830

Gln Leu Arg Glu Lys Asp Asn Pro Arg Tyr Leu Glu Gln Gln Lys
1835                1840                1845

Gly Val His Ile Ser Pro Arg Ser Lys Asp Ala Leu Leu Thr Glu
1850                1855                1860

Leu Asp Ile Thr Asn Phe Ala Leu Asn Asn Leu Ser Val Ala Phe
1865                1870                1875

Gly Pro Asp Phe Ala Cys Tyr Asp Gly Arg Thr Val Ser Arg Gln
1880                1885                1890

Pro Asn Thr Asp Leu Gln Leu Ile Ser Arg Val Leu Lys Ile Glu
1895                1900                1905

Gly Glu Arg Leu Asn Phe Lys Gln Pro Ser Thr Ile Tyr Ala Glu
1910                1915                1920

Tyr Asp Val Pro Glu Asp Ala Trp Tyr Gln Gln Asn Ala Ser
1925                1930                1935

Met Thr Met Pro Tyr Ser Val Leu Met Glu Ile Ala Leu Gln Pro
1940                1945                1950

Cys Gly Leu Leu Gly Ala Tyr Leu Gly Ser Thr Leu Pro Phe Ser
```

```
            1955                1960                1965

Asp Lys Asn Leu Phe Phe Arg Asn Leu Asp Gly Thr Gly Glu Met
    1970                1975                1980

Leu Glu Leu Pro Met Gly Thr Asp Trp Arg Gly Lys Thr Ile His
    1985                1990                1995

Asn Lys Ala Val Leu Ala Ser Ser Val Ala Leu Gly Gly Thr Val
    2000                2005                2010

Leu Gln Asn Tyr Thr Phe Glu Leu Ser Ile Asp Gly Gln Val Phe
    2015                2020                2025

Tyr Lys Gly Lys Ser Ser Phe Gly Phe Phe Pro Ala Glu Ala Leu
    2030                2035                2040

Ala Gln Gln Val Gly Leu Asp Asn Gly Thr Ala Val Ala Pro Trp
    2045                2050                2055

Tyr Gln Gln Gln Asn Leu Ala Gln Lys Asp Tyr Met Ser Ile Lys
    2060                2065                2070

Leu Asp Ser Leu Tyr Gly Lys Met Lys Leu Phe Lys Ala Pro Ala
    2075                2080                2085

Asn Lys Pro His Tyr His Leu Ser Gly Glu Gln Leu Ser Leu Leu
    2090                2095                2100

Asn Asn Leu Lys Ile Val Lys Asp Gly Gly Gln Tyr Gly Lys Gly
    2105                2110                2115

Tyr Ile Tyr Gly His Gln Ala Ile Asn Leu Tyr Asp Trp Phe Phe
    2120                2125                2130

Thr Cys His Phe Tyr Gln Asp Pro Val Met Pro Gly Ser Leu Gly
    2135                2140                2145

Val Glu Ala Ile Leu Gln Ala Met Gln Thr Phe Ala Leu Gln Gln
    2150                2155                2160

Asp Leu Gly Lys Asp Phe Lys Ser Pro Arg Phe Val Gln Val Pro
    2165                2170                2175

Gln His Thr Thr Val Trp Lys Tyr Arg Gly Gln Ile Leu Gln Gly
    2180                2185                2190

Val Glu Asn Met His Cys Glu Val His Phe Lys Ser Ile Glu Lys
    2195                2200                2205

Lys Gly Glu Gln Leu Val Ile Val Gly Asp Ala Tyr Leu Trp Asn
    2210                2215                2220

Glu Asp Thr Arg Ile Tyr Gln Ile Thr Asp Leu Ala Leu Gly Ile
    2225                2230                2235

Glu Glu Ala
    2240

<210> SEQ ID NO 31
<211> LENGTH: 2059
<212> TYPE: PRT
<213> ORGANISM: Schizochytrium sp

<400> SEQUENCE: 31

Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60
```

```
Lys Ala Glu Arg Ser Lys Tyr Ala Asp Thr Phe Cys Asn Glu Thr Tyr
 65                  70                  75                  80

Gly Thr Leu Asp Glu Asn Glu Ile Asp Asn Glu His Glu Leu Leu Leu
                 85                  90                  95

Asn Leu Ala Lys Gln Ala Leu Ala Glu Thr Ser Val Lys Asp Ser Thr
            100                 105                 110

Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
    130                 135                 140

Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
                165                 170                 175

Ser Phe Val Ala Glu Glu Leu Asn Leu Gly Ala Leu His Tyr Ser Val
            180                 185                 190

Asp Ala Ala Cys Ala Thr Ala Leu Tyr Val Leu Arg Leu Ala Gln Asp
        195                 200                 205

His Leu Val Ser Gly Ala Ala Asp Val Met Leu Cys Gly Ala Thr Cys
    210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
                245                 250                 255

Ser Gln Gly Leu Thr Pro Gly Glu Gly Gly Ser Ile Met Val Leu Lys
            260                 265                 270

Arg Leu Asp Asp Ala Ile Arg Asp Gly Asp His Ile Tyr Gly Thr Leu
        275                 280                 285

Leu Gly Ala Asn Val Ser Asn Ser Gly Thr Gly Leu Pro Leu Lys Pro
    290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
                325                 330                 335

Thr Pro Gln Gly Asp Arg Val Glu Ile Asp Ala Val Lys Ala Cys Phe
            340                 345                 350

Glu Gly Lys Val Pro Arg Phe Gly Thr Thr Lys Gly Asn Phe Gly His
        355                 360                 365

Thr Leu Val Ala Ala Gly Phe Ala Gly Met Cys Lys Val Leu Leu Ser
    370                 375                 380

Met Lys His Gly Ile Ile Pro Thr Pro Gly Ile Asp Asp Glu Thr
385                 390                 395                 400

Lys Met Asp Pro Leu Val Val Ser Gly Glu Ala Ile Pro Trp Pro Glu
                405                 410                 415

Thr Asn Gly Glu Pro Lys Arg Ala Gly Leu Ser Ala Phe Gly Phe Gly
            420                 425                 430

Gly Thr Asn Ala His Ala Val Phe Glu Glu His Asp Pro Ser Asn Ala
        435                 440                 445

Ala Cys Thr Gly His Asp Ser Ile Ser Ala Leu Ser Ala Arg Cys Gly
    450                 455                 460

Gly Glu Ser Asn Met Arg Ile Ala Ile Thr Gly Met Asp Ala Thr Phe
465                 470                 475                 480

Gly Ala Leu Lys Gly Leu Asp Ala Phe Glu Arg Ala Ile Tyr Thr Gly
```

```
                485             490             495
Ala His Gly Ala Ile Pro Leu Pro Glu Lys Arg Trp Arg Phe Leu Gly
                500             505             510
Lys Asp Lys Asp Phe Leu Asp Leu Cys Gly Val Lys Ala Thr Pro His
                515             520             525
Gly Cys Tyr Ile Glu Asp Val Glu Val Asp Phe Gln Arg Leu Arg Thr
                530             535             540
Pro Met Thr Pro Glu Asp Met Leu Leu Pro Gln Gln Leu Leu Ala Val
545             550             555             560
Thr Thr Ile Asp Arg Ala Ile Leu Asp Ser Gly Met Lys Lys Gly Gly
                565             570             575
Asn Val Ala Val Phe Val Gly Leu Gly Thr Asp Leu Glu Leu Tyr Arg
                580             585             590
His Arg Ala Arg Val Ala Leu Lys Glu Arg Val Arg Pro Glu Ala Ser
                595             600             605
Lys Lys Leu Asn Asp Met Met Gln Tyr Ile Asn Asp Cys Gly Thr Ser
                610             615             620
Thr Ser Tyr Thr Ser Tyr Ile Gly Asn Leu Val Ala Thr Arg Val Ser
625             630             635             640
Ser Gln Trp Gly Phe Thr Gly Pro Ser Phe Thr Ile Thr Glu Gly Asn
                645             650             655
Asn Ser Val Tyr Arg Cys Ala Glu Leu Gly Lys Tyr Leu Leu Glu Thr
                660             665             670
Gly Glu Val Asp Gly Val Val Ala Gly Val Asp Leu Cys Gly Ser
                675             680             685
Ala Glu Asn Leu Tyr Val Lys Ser Arg Arg Phe Lys Val Ser Thr Ser
                690             695             700
Asp Thr Pro Arg Ala Ser Phe Asp Ala Ala Asp Gly Tyr Phe Val
705             710             715             720
Gly Glu Gly Cys Gly Ala Phe Val Leu Lys Arg Glu Thr Ser Cys Thr
                725             730             735
Lys Asp Asp Arg Ile Tyr Ala Cys Met Asp Ala Ile Val Pro Gly Asn
                740             745             750
Val Pro Ser Ala Cys Leu Arg Glu Ala Leu Asp Gln Ala Arg Val Lys
                755             760             765
Pro Gly Asp Ile Glu Met Leu Glu Leu Ser Ala Asp Ser Ala Arg His
                770             775             780
Leu Lys Asp Pro Ser Val Leu Pro Lys Glu Leu Thr Ala Glu Glu
785             790             795             800
Ile Gly Gly Leu Gln Thr Ile Leu Arg Asp Asp Lys Leu Pro Arg
                805             810             815
Asn Val Ala Thr Gly Ser Val Lys Ala Thr Val Gly Asp Thr Gly Tyr
                820             825             830
Ala Ser Gly Ala Ala Ser Leu Ile Lys Ala Ala Leu Cys Ile Tyr Asn
                835             840             845
Arg Tyr Leu Pro Ser Asn Gly Asp Asp Trp Asp Glu Pro Ala Pro Glu
                850             855             860
Ala Pro Trp Asp Ser Thr Leu Phe Ala Cys Gln Thr Ser Arg Ala Trp
865             870             875             880
Leu Lys Asn Pro Gly Glu Arg Arg Tyr Ala Ala Val Ser Gly Val Ser
                885             890             895
Glu Thr Arg Ser Cys Tyr Ser Val Leu Leu Ser Glu Ala Glu Gly His
                900             905             910
```

```
Tyr Glu Arg Glu Asn Arg Ile Ser Leu Asp Glu Glu Ala Pro Lys Leu
            915                 920                 925

Ile Val Leu Arg Ala Asp Ser His Glu Glu Ile Leu Gly Arg Leu Asp
    930                 935                 940

Lys Ile Arg Glu Arg Phe Leu Gln Pro Thr Gly Ala Ala Pro Arg Glu
945                 950                 955                 960

Ser Glu Leu Lys Ala Gln Ala Arg Arg Ile Phe Leu Glu Leu Leu Gly
                965                 970                 975

Glu Thr Leu Ala Gln Asp Ala Ala Ser Ser Gly Ser Gln Lys Pro Leu
            980                 985                 990

Ala Leu Ser Leu Val Ser Thr Pro Ser Lys Leu Gln Arg Glu Val Glu
            995                 1000                1005

Leu Ala Ala Lys Gly Ile Pro Arg Cys Leu Lys Met Arg Arg Asp
    1010                1015                1020

Trp Ser Ser Pro Ala Gly Ser Arg Tyr Ala Pro Glu Pro Leu Ala
    1025                1030                1035

Ser Asp Arg Val Ala Phe Met Tyr Gly Glu Gly Arg Ser Pro Tyr
    1040                1045                1050

Tyr Gly Ile Thr Gln Asp Ile His Arg Ile Trp Pro Glu Leu His
    1055                1060                1065

Glu Val Ile Asn Glu Lys Thr Asn Arg Leu Trp Ala Glu Gly Asp
    1070                1075                1080

Arg Trp Val Met Pro Arg Ala Ser Phe Lys Ser Glu Leu Glu Ser
    1085                1090                1095

Gln Gln Gln Glu Phe Asp Arg Asn Met Ile Glu Met Phe Arg Leu
    1100                1105                1110

Gly Ile Leu Thr Ser Ile Ala Phe Thr Asn Leu Ala Arg Asp Val
    1115                1120                1125

Leu Asn Ile Thr Pro Lys Ala Ala Phe Gly Leu Ser Leu Gly Glu
    1130                1135                1140

Ile Ser Met Ile Phe Ala Phe Ser Lys Lys Asn Gly Leu Ile Ser
    1145                1150                1155

Asp Gln Leu Thr Lys Asp Leu Arg Glu Ser Asp Val Trp Asn Lys
    1160                1165                1170

Ala Leu Ala Val Glu Phe Asn Ala Leu Arg Glu Ala Trp Gly Ile
    1175                1180                1185

Pro Gln Ser Val Pro Lys Asp Glu Phe Trp Gln Gly Tyr Ile Val
    1190                1195                1200

Arg Gly Thr Lys Gln Asp Ile Glu Ala Ala Ile Ala Pro Asp Ser
    1205                1210                1215

Lys Tyr Val Arg Leu Thr Ile Ile Asn Asp Ala Asn Thr Ala Leu
    1220                1225                1230

Ile Ser Gly Lys Pro Asp Ala Cys Lys Ala Ala Ile Ala Arg Leu
    1235                1240                1245

Gly Gly Asn Ile Pro Ala Leu Pro Val Thr Gln Gly Met Cys Gly
    1250                1255                1260

His Cys Pro Glu Val Gly Pro Tyr Thr Lys Asp Ile Ala Lys Ile
    1265                1270                1275

His Ala Asn Leu Glu Phe Pro Val Val Asp Gly Leu Asp Leu Trp
    1280                1285                1290

Thr Thr Ile Asn Gln Lys Arg Leu Val Pro Arg Ala Thr Gly Ala
    1295                1300                1305
```

```
Lys Asp Glu Trp Ala Pro Ser Ser Phe Gly Glu Tyr Ala Gly Gln
1310                1315                1320

Leu Tyr Glu Lys Gln Ala Asn Phe Pro Gln Ile Val Glu Thr Ile
    1325                1330                1335

Tyr Lys Gln Asn Tyr Asp Val Phe Val Glu Val Gly Pro Asn Asn
1340                1345                1350

His Arg Ser Thr Ala Val Arg Thr Thr Leu Gly Pro Gln Arg Asn
    1355                1360                1365

His Leu Ala Gly Ala Ile Asp Lys Gln Asn Glu Asp Ala Trp Thr
1370                1375                1380

Thr Ile Val Lys Leu Val Ala Ser Leu Lys Ala His Leu Val Pro
    1385                1390                1395

Gly Val Thr Ile Ser Pro Leu Tyr His Ser Lys Leu Val Ala Glu
1400                1405                1410

Ala Glu Ala Cys Tyr Ala Ala Leu Cys Lys Gly Glu Lys Pro Lys
    1415                1420                1425

Lys Asn Lys Phe Val Arg Lys Ile Gln Leu Asn Gly Arg Phe Asn
1430                1435                1440

Ser Lys Ala Asp Pro Ile Ser Ser Ala Asp Leu Ala Ser Phe Pro
    1445                1450                1455

Pro Ala Asp Pro Ala Ile Glu Ala Ala Ile Ser Ser Arg Ile Met
1460                1465                1470

Lys Pro Val Ala Pro Lys Phe Tyr Ala Arg Leu Asn Ile Asp Glu
    1475                1480                1485

Gln Asp Glu Thr Arg Asp Pro Ile Leu Asn Lys Asp Asn Ala Pro
1490                1495                1500

Ser Ser Ser Ser Ser Ser Ser Ser Ser Ser Ser Ser Ser Ser Ser
    1505                1510                1515

Pro Ser Pro Ala Pro Ser Ala Pro Val Gln Lys Lys Ala Ala Pro
1520                1525                1530

Ala Ala Glu Thr Lys Ala Val Ala Ser Ala Asp Ala Leu Arg Ser
    1535                1540                1545

Ala Leu Leu Asp Leu Asp Ser Met Leu Ala Leu Ser Ser Ala Ser
1550                1555                1560

Ala Ser Gly Asn Leu Val Glu Thr Ala Pro Ser Asp Ala Ser Val
    1565                1570                1575

Ile Val Pro Pro Cys Asn Ile Ala Asp Leu Gly Ser Arg Ala Phe
1580                1585                1590

Met Lys Thr Tyr Gly Val Ser Ala Pro Leu Tyr Thr Gly Ala Met
    1595                1600                1605

Ala Lys Gly Ile Ala Ser Ala Asp Leu Val Ile Ala Ala Gly Arg
1610                1615                1620

Gln Gly Ile Leu Ala Ser Phe Gly Ala Gly Gly Leu Pro Met Gln
    1625                1630                1635

Val Val Arg Glu Ser Ile Glu Lys Ile Gln Ala Ala Leu Pro Asn
1640                1645                1650

Gly Pro Tyr Ala Val Asn Leu Ile His Ser Pro Phe Asp Ser Asn
    1655                1660                1665

Leu Glu Lys Gly Asn Val Asp Leu Phe Leu Glu Lys Gly Val Thr
1670                1675                1680

Phe Val Glu Ala Ser Ala Phe Met Thr Leu Thr Pro Gln Val Val
    1685                1690                1695
```

-continued

Arg Tyr Arg Ala Ala Gly Leu Thr Arg Asn Ala Asp Gly Ser Val
    1700            1705                1710

Asn Ile Arg Asn Arg Ile Ile Gly Lys Val Ser Arg Thr Glu Leu
    1715            1720                1725

Ala Glu Met Phe Met Arg Pro Ala Pro Glu His Leu Leu Gln Lys
    1730            1735                1740

Leu Ile Ala Ser Gly Glu Ile Asn Gln Glu Gln Ala Glu Leu Ala
    1745            1750                1755

Arg Arg Val Pro Val Ala Asp Asp Ile Ala Val Glu Ala Asp Ser
    1760            1765                1770

Gly Gly His Thr Asp Asn Arg Pro Ile His Val Ile Leu Pro Leu
    1775            1780                1785

Ile Ile Asn Leu Arg Asp Arg Leu His Arg Glu Cys Gly Tyr Pro
    1790            1795                1800

Ala Asn Leu Arg Val Arg Val Gly Ala Gly Gly Ile Gly Cys
    1805            1810                1815

Pro Gln Ala Ala Leu Ala Thr Phe Asn Met Gly Ala Ser Phe Ile
    1820            1825                1830

Val Thr Gly Thr Val Asn Gln Val Ala Lys Gln Ser Gly Thr Cys
    1835            1840                1845

Asp Asn Val Arg Lys Gln Leu Ala Lys Ala Thr Tyr Ser Asp Val
    1850            1855                1860

Cys Met Ala Pro Ala Ala Asp Met Phe Glu Glu Gly Val Lys Leu
    1865            1870                1875

Gln Val Leu Lys Lys Gly Thr Met Phe Pro Ser Arg Ala Asn Lys
    1880            1885                1890

Leu Tyr Glu Leu Phe Cys Lys Tyr Asp Ser Phe Glu Ser Met Pro
    1895            1900                1905

Pro Ala Glu Leu Ala Arg Val Glu Lys Arg Ile Phe Ser Arg Ala
    1910            1915                1920

Leu Glu Glu Val Trp Asp Glu Thr Lys Asn Phe Tyr Ile Asn Arg
    1925            1930                1935

Leu His Asn Pro Glu Lys Ile Gln Arg Ala Glu Arg Asp Pro Lys
    1940            1945                1950

Leu Lys Met Ser Leu Cys Phe Arg Trp Tyr Leu Ser Leu Ala Ser
    1955            1960                1965

Arg Trp Ala Asn Thr Gly Ala Ser Asp Arg Val Met Asp Tyr Gln
    1970            1975                1980

Val Trp Cys Gly Pro Ala Ile Gly Ser Phe Asn Asp Phe Ile Lys
    1985            1990                1995

Gly Thr Tyr Leu Asp Pro Ala Val Ala Asn Glu Tyr Pro Cys Val
    2000            2005                2010

Val Gln Ile Asn Lys Gln Ile Leu Arg Gly Ala Cys Phe Leu Arg
    2015            2020                2025

Arg Leu Glu Ile Leu Arg Asn Ala Arg Leu Ser Asp Gly Ala Ala
    2030            2035                2040

Ala Leu Val Ala Ser Ile Asp Asp Thr Tyr Val Pro Ala Glu Lys
    2045            2050                2055

Leu